US007635680B2

(12) United States Patent
Allison

(10) Patent No.: US 7,635,680 B2
(45) Date of Patent: Dec. 22, 2009

(54) ATTENUATION OF REPERFUSION INJURY

(75) Inventor: Anthony Allison, Belmont, CA (US)

(73) Assignee: Alavita Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 11/734,471

(22) Filed: Apr. 12, 2007

(65) Prior Publication Data

US 2008/0069823 A1    Mar. 20, 2008

Related U.S. Application Data

(63) Continuation-in-part of application No. 11/486,667, filed on Jul. 14, 2006, which is a continuation-in-part of application No. 11/267,837, filed on Nov. 3, 2005, which is a continuation-in-part of application No. 11/078,231, filed on Mar. 10, 2005, which is a continuation-in-part of application No. 10/080,370, filed on Feb. 21, 2002, now Pat. No. 6,962,903.

(60) Provisional application No. 60/579,589, filed on Jun. 14, 2004, provisional application No. 60/552,428, filed on Mar. 11, 2004, provisional application No. 60/332,582, filed on Nov. 21, 2001, provisional application No. 60/270,402, filed on Feb. 21, 2001.

(51) Int. Cl.
*A61K 38/17*    (2006.01)

(52) U.S. Cl. .............. 514/12; 514/2; 530/350; 530/300; 435/7.1

(58) Field of Classification Search ........................ None
See application file for complete search history.

(56) References Cited

U.S. PATENT DOCUMENTS

| | | | |
|---|---|---|---|
| 4,002,531 A | 1/1977 | Royer et al. |
| 4,179,337 A | 12/1979 | Davis et al. |
| 4,507,229 A | 3/1985 | Bohn et al. |
| 4,732,891 A | 3/1988 | Maki et al. |
| 4,736,018 A | 4/1988 | Reutelingsperger et al. |
| 4,897,355 A | 1/1990 | Eppstein et al. |
| 4,937,324 A | 6/1990 | Fujikawa et al. |
| 4,965,251 A | 10/1990 | Stamatoyannopoulos |
| 5,066,787 A | 11/1991 | Reutelingsperger et al. |
| 5,066,788 A | 11/1991 | Reutelingsperger et al. |
| 5,097,019 A | 3/1992 | Lobermann et al. |
| 5,225,537 A | 7/1993 | Foster et al. |
| 5,229,367 A | 7/1993 | Perretti et al. |
| 5,258,497 A | 11/1993 | Reutelingsperger et al. |
| 5,290,915 A | 3/1994 | Nakao et al. |
| 5,296,467 A | 3/1994 | Reutelingsperger |
| 5,360,789 A | 11/1994 | Nakao et al. |
| 5,484,711 A | 1/1996 | Wallner et al. |
| 5,589,395 A | 12/1996 | Romisch et al. |
| 5,591,633 A | 1/1997 | Saino et al. |
| 5,608,060 A | 3/1997 | Axworthy et al. |
| 5,612,460 A | 3/1997 | Zalipsky et al. |
| 5,632,986 A | 5/1997 | Tait et al. |
| 5,837,842 A | 11/1998 | Hauptmann et al. |
| 5,849,600 A | 12/1998 | Nixon et al. |
| 5,955,437 A | 9/1999 | Reutelingsperger |
| 5,968,477 A | 10/1999 | Kasina et al. |
| 6,169,078 B1 | 1/2001 | Hughes et al. |
| 6,171,577 B1 | 1/2001 | Kasina et al. |
| 6,194,214 B1 | 2/2001 | Kraus |
| 6,242,570 B1 | 6/2001 | Sytkowski et al. |
| 6,312,694 B1 | 11/2001 | Thorpe et al. |
| 6,323,313 B1 | 11/2001 | Tait et al. |
| 6,358,508 B1 | 3/2002 | Ni et al. |
| 6,387,366 B1 | 5/2002 | Hurwitz et al. |
| 2002/0082623 A1 | 6/2002 | Osther |
| 2002/0088015 A1 | 7/2002 | Shi |
| 2002/0132256 A1 | 9/2002 | Cavanaugh |
| 2003/0027763 A1 | 2/2003 | Bennett et al. |
| 2003/0113330 A1 | 6/2003 | Uhal |
| 2003/0152513 A1 | 8/2003 | Blankenberg et al. |
| 2003/0175831 A1 | 9/2003 | Canton et al. |
| 2003/0211548 A1 | 11/2003 | Packard et al. |
| 2004/0002056 A1 | 1/2004 | Lorens et al. |
| 2004/0018590 A1 | 1/2004 | Gerngross et al. |

(Continued)

FOREIGN PATENT DOCUMENTS

CN    1343777    4/2002

(Continued)

OTHER PUBLICATIONS

Seffernick et al. (J. Bacteriology, vol. 183, pp. 2405-2410, 2001).*

(Continued)

*Primary Examiner*—Hope A Robinson
(74) *Attorney, Agent, or Firm*—Swanson & Bratschun, L.L.C.

(57) ABSTRACT

Modified annexin proteins, including a homodimer of human annexin V, are provided. Methods for their use, such as to prevent thrombosis without increasing hemorrhage, enhancing the survivability of platelets during storage or transfusion and to attenuate ischemia-reperfusion injury (IPI), are also provided. The modified annexins bind phosphatidylserine (PS) on cell surfaces, thereby preventing the assembly of the prothrombinase complex. The modified annexin decreases the binding of leukocytes and platelets during post-ischemic reperfusion, thereby restoring microvascular blood flow and decreasing organ damage. In addition, the modified annexin prevents lipid loss from platelets during storage.

14 Claims, 6 Drawing Sheets

U.S. PATENT DOCUMENTS

| | | | |
|---|---|---|---|
| 2004/0029151 A1 | 2/2004 | Mahadevappa et al. |
| 2004/0042959 A1 | 3/2004 | Montalto et al. |
| 2004/0171629 A1 | 9/2004 | Zervos |
| 2005/0053637 A1 | 3/2005 | Ma'Or |
| 2005/0084547 A1 | 4/2005 | Subbiah |
| 2005/0130230 A1 | 6/2005 | Davalos et al. |
| 2005/0136455 A1 | 6/2005 | Lehmann et al. |
| 2005/0142657 A1 | 6/2005 | Grein et al. |
| 2005/0147692 A1 | 7/2005 | Roth |
| 2005/0208151 A1 | 9/2005 | Hurez et al. |
| 2005/0222030 A1 | 10/2005 | Allison |
| 2005/0244897 A1 | 11/2005 | Zeiher et al. |

FOREIGN PATENT DOCUMENTS

| | | |
|---|---|---|
| CN | 1401662 | 3/2003 |
| CN | 1404872 | 3/2003 |
| DE | 19541284 A1 | 5/1996 |
| EP | 0318703 | 7/1989 |
| JP | 04198195 A | 7/1992 |
| JP | 5001096 | 1/1993 |
| JP | 116286 | 4/1994 |
| JP | 7072147 | 3/1995 |
| JP | 7072149 | 3/1995 |
| WO | WO8807576 | 10/1988 |
| WO | WO9107187 | 5/1991 |
| WO | WO9116882 | 11/1991 |
| WO | WO9207870 | 5/1992 |
| WO | WO 92/19279 | 11/1992 |
| WO | WO9401554 | 1/1994 |
| WO | WO9534315 | 12/1995 |
| WO | WO9603655 | 2/1996 |
| WO | WO9717084 | 5/1997 |
| WO | WO 97/24440 | 7/1997 |
| WO | WO9801563 | 1/1998 |
| WO | WO 98/04294 | 2/1998 |
| WO | WO 98/31383 | 7/1998 |
| WO | WO9829442 | 7/1998 |
| WO | WO9902992 | 1/1999 |
| WO | WO9919470 | 4/1999 |
| WO | WO9924054 | 5/1999 |
| WO | WO9948916 | 9/1999 |
| WO | WO0002587 | 1/2000 |
| WO | WO0010673 | 3/2000 |
| WO | WO0011026 | 3/2000 |
| WO | WO0012547 | 3/2000 |
| WO | WO0038517 | 7/2000 |
| WO | WO0111372 | 2/2001 |
| WO | WO0123426 | 4/2001 |
| WO | WO0133228 | 5/2001 |
| WO | WO0220769 | 3/2002 |
| WO | WO02067767 | 9/2002 |
| WO | WO02080754 | 10/2002 |
| WO | WO02087497 | 11/2002 |
| WO | WO02087498 | 11/2002 |
| WO | WO02089657 | 11/2002 |
| WO | WO03103577 | 5/2003 |
| WO | WO03062264 | 7/2003 |
| WO | WO03079987 | 10/2003 |
| WO | WO03084333 | 10/2003 |
| WO | WO03093478 | 11/2003 |
| WO | WO03105814 | 12/2003 |
| WO | WO2004006963 | 1/2004 |
| WO | WO2004090554 | 10/2004 |
| WO | WO2004112717 | 12/2004 |
| WO | WO2004113561 | 12/2004 |
| WO | WO2005014801 | 2/2005 |
| WO | WO2005023096 | 3/2005 |
| WO | WO2005027965 | 3/2005 |
| WO | WO2005028490 | 3/2005 |
| WO | WO2005053744 | 6/2005 |
| WO | WO2005058351 | 6/2005 |
| WO | WO2005058352 | 6/2005 |
| WO | WO2005065418 | 7/2005 |
| WO | WO2005069000 | 7/2005 |
| WO | WO2005018436 | 8/2005 |
| WO | WO2005078124 | 8/2005 |
| WO | WO2005087275 | 9/2005 |
| WO | WO2005099744 | 10/2005 |
| WO | WO2005103720 | 11/2005 |
| WO | WO2005113006 | 12/2005 |
| WO | WO2005120166 | 12/2005 |
| WO | WO2006029525 | 3/2006 |
| WO | WO2006017578 | 5/2006 |
| WO | WO2006052924 | 5/2006 |
| WO | WO2006053725 | 5/2006 |
| WO | WO2006060898 | 6/2006 |
| WO | WO2006064451 | 6/2006 |
| WO | WO2006064453 | 6/2006 |

OTHER PUBLICATIONS

Wells, Biochemistry, vol. 29, pp. 8509-8517, 1990.*
Allan et al., Nature 295:612-613 (1982).
Bangham et al., J. Mol. Biol. 23:238-252 (1965).
Behr et al., Proc. Natl. Acad. Sci. USA 86:6982-6986 (1989).
Benz and A. Hofmann, Biol. Chem. 378:177-183 (1997).
Bernard et al., Am. Rev. Respir. Dis. 144:1095-1101 (1991).
Brittain et al., Blood 81:2137-2143 (1993).
Burger, FEBS Lett. 329:25 28 (1993).
Campos et al., Biochemistry 37:8004-8008 (1998).
Chap et al., Biochem Biophys Res Commun 1988, 150:972-978.
Chow et al., J. Lab. Clin. Med. 135:66-72 (2000).
D'Amico et al., FASEB J, Express Article 10.1096/99-0602FJE, 2000.
D'Amico et al., FASEB J. vol. 14, pp. 1867-1869, 2000.
Database WPI, Section CH, Weed 200036, Derwent Publications Ltd, London, Class B04, Shanghai Inst Biochem Chinese Acad (2000) Abstract.
Delgado et al. (1992) Critical Rev in Therapeutic Drug Carrier Systems 9(3/4):249-304.
Felgner et al., Proc. Natl. Acad. Sci. USA 84: 7413-7417 (1987).
Fritsma, in Hemostasis and Thrombosis in the Clinical Laboratory (Corriveau, D.M. and Fritsma, G.A. EDS) J.P. Lipincott Co., Philadelphia (1989), pp. 92-124, 1991.
Fukunaga et al., Endocrinol. 115:757 (1984).
Funakoshi et al., Biochemistry 1987, 26:5572-5578.
Funakoshi et al., Biochemistry 1987, 26:8087-8092.
Gerke et al., "Annexins:From Structure to Function", Physiol. Rev, Bol. 82, pp. 331-371, 2002.
Green et al., Am. J. Hematol. 23:317 (1986).
Grundmann et al., Behring Inst Mitt 1988, 82:59-67.
Grundmann et al., Proc Natl Acad Sci USA 1988, 85:3708-3712.
Haupt et al., Crit. Care Med. 19:1339-1347 (1991).
Haut et al., J. Lab. Clin. Med. 82:44-53 (1973).
Heathcote et al., N. Engl. J. Med. 343:1673-1680 (2000).
Hebbel et al., Abstract. Clin. Res. 41:762A (1993).
Hermanson, Bioconj Tech. New York, Acad. Press (1996), pp. 173-176.
Huber et al., EMBO Journal 9:3867 (1990).
Iwasaki et al., J Biochem (Tokyo) 1987, 102:1261-1273.
Kang et al., Trends Cardiovasc. Med. 9:92-102 (1999).
Kaplan et al., Blood 57:199-202 (1981).
Kaplan et al., J Biol Chem 1988, 263:8037-8043.
Kassam et al. (1998) J Biol Chem 273(8):4790-4799.
Kim et al., Biochim. Biophys. Acta 728:339 (1983).
Knauf et al., J. Biol. Chem. 263:15064-15070 (1988).
Kuypers et al., Blood 87:1179-1187 (1996).
Lubin et al., J. Clin. Invest. 67:1643-1649 (1981).
Maurer-Fogy et al., Eur J Biochem 1988, 174:585-592.
Mayhew et al., Biochim. Biophys. Acta 775:169 (1984).
Meinkoth et al., Anal. Biochem. 138:267-284 (1984).
Merten et al., Circulation 99:2577-2582 (1999).
Murata et al., Nature 388:678-682 (1997).

Nakao et al., Chem Pharm Bull (Tokyo) 1990, 38:1957-1960.
Olson et al., Biochim. Biophys. Acta 557:9 (1979).
Pepinsky et al. A Dimeric Form of Lipocortin-1 in Human Placenta. Biochemistry Journal. 1989, vol. 263, pp. 97-103.
Pepinsky et al. (1988) J Biol Chem 263(22):10799-10811.
Rand et al. Antiphospholipid Antibodies Accelerate Plasma Coagulation by Inhibiting Annexin-V Binding to Phospholipids. A Lupus Procoagulant Phenomenon. Blood. Sep. 1, 1998, vol. 92, No. 5, pp. 1652-1660.
Reutelingsperger et al., Eur J Biochem 1985, 151:625-629.
Reutelingsperger et al., Eur J Biochem 1988, 173:171-178.
Richardson et al., Br. J. Haematol. 41:95 (1979).
Robinson et al., "Optimizing the Stability of Single Chain Proteins by Linker Length and Composition Mutagenesis", Proc. Nat. Acad. Sci. USA, vol. 95, pp. 5929-5934, 1998.
Romisch et al., Biochem J 1990, 272:223-229.
Romisch et al., Thromb Res 1990, 60:355-366.
Romisch et al., Thrombosis Res 1991, 61:93.
Rothhut et al., Biochem J 1989, 263:929-935.
Schlaepfer et al., Proc Natl Acad Sci USA 1987, 84:6078-6082.
Seffernick et al. (2001) J. Bacteriology 183:2405-2410.
Setty et al., Blood 99:1564-1571 (2002).
Stratton et al., Circulation 92:3113-3121 (1995).
Strauss et al., J. Nucl. Med. 41 (5 Suppl.):149P (2000).
Stueber et al. (1995) Peptide Research 8(2):78-85.
Sugihara et al., Blood 80:2634-2642 (1992).
Sun et al., Thromb. Res. 69:289 296 (1993).
Sytkowski et al. (1998) Proc Natl Acad Sci USA 95:1184-1188.
Szoka, et al., Proc. Natl. Acad. Sci. 75:4194 (1978).
Tait et al., J. Biol. Chem. 264:7944-7949 (1989).
Tait, J. et al. Prourokinase-Annexin V Chimera. Journal of Biological Chemistry. Sep. 15, 1995, vol. 270, No. 27, pp. 21594-21599, Especially Abstract.
Thiagarajan and Benedict, Circulation 96:2339-2347 (1997).
Thiagarajan and Tait, J. Biol. Chem. 265:17420-17423 (1990).
Van Heerde et al., Arterioscler. Thromb. 14:824-830 (1994).
Van Ryn-McKenna et al., Thromb. Haemost. 69:227-230 (1993).
Veronese et al., Biomaterials 22:405 (2001).
Wells (1990) Biochemistry 29:8509-8517.
Zanma et al. (1991) J Biochem 110(6):868-872.
Peck-Radosavljevic et al. (2000) Thrombopoietin induces rapid resolution of thrombocytopenia after orthotopic liver transplantation through increased platelet production, Blood 95(3):795-801.
Allison, A-Geneseq, Direct Submission, Accession # AEH69391, May 18, 2006.

* cited by examiner

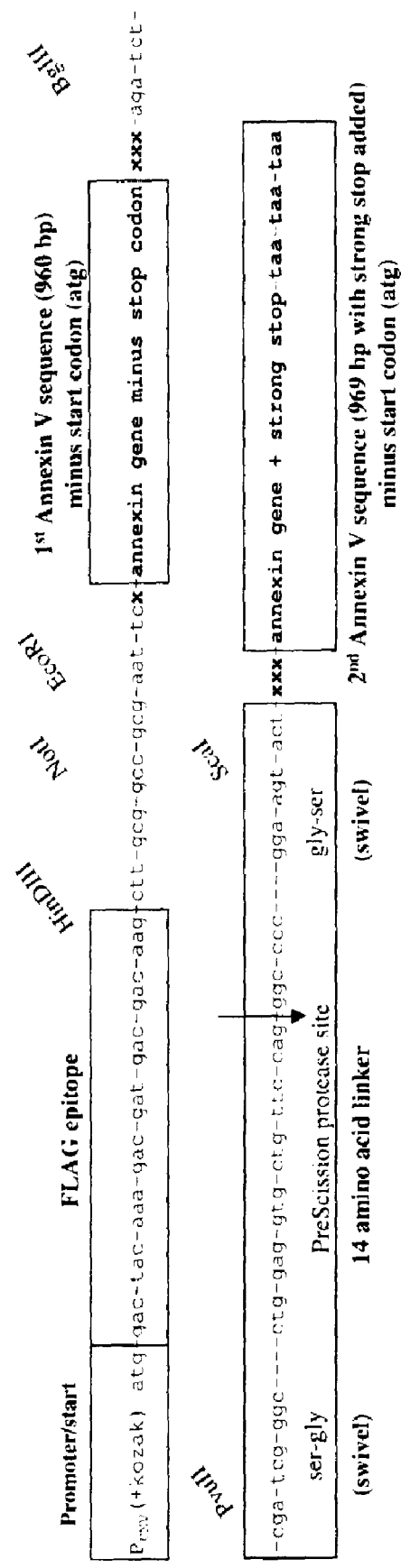

FIG. 4A
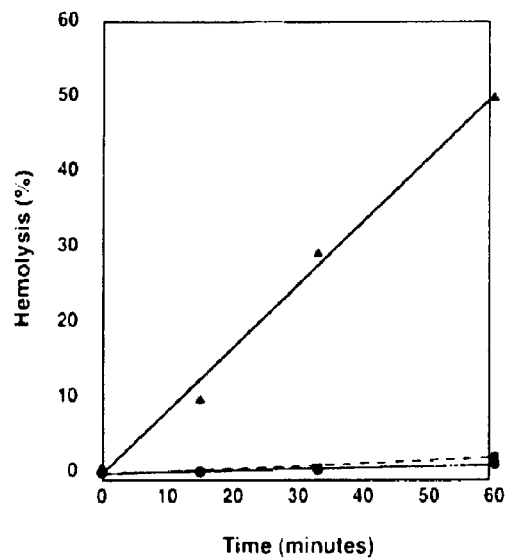
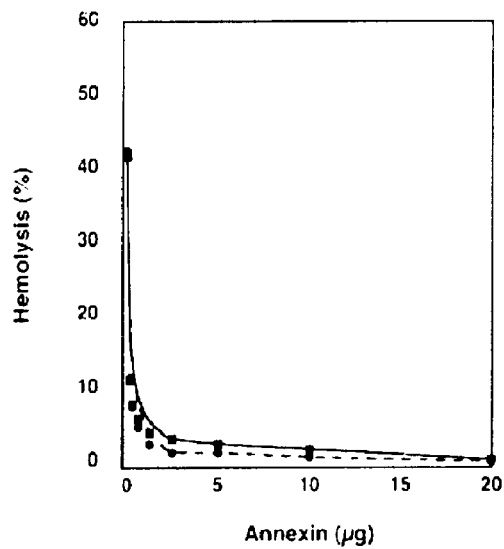
FIG. 4B
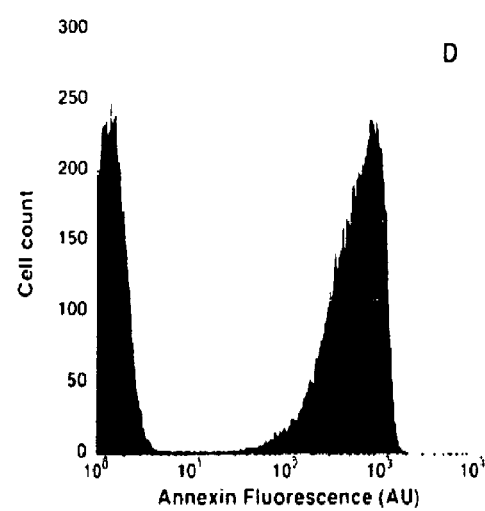
FIG. 4C

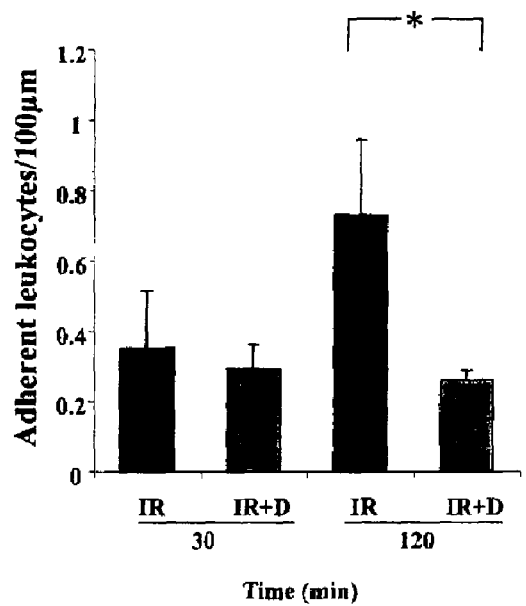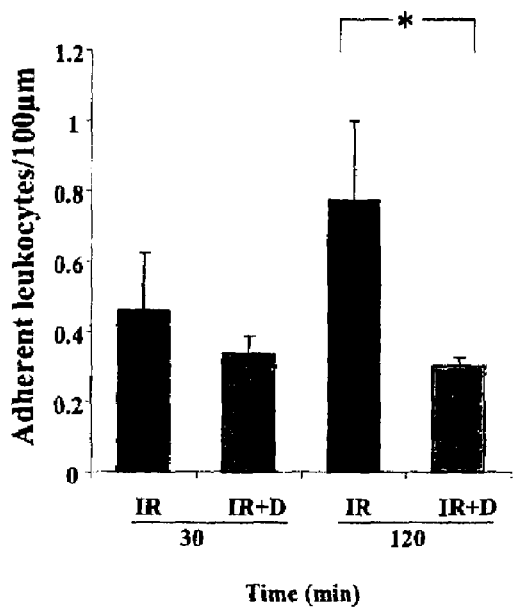
FIG. 6A  FIG. 6B
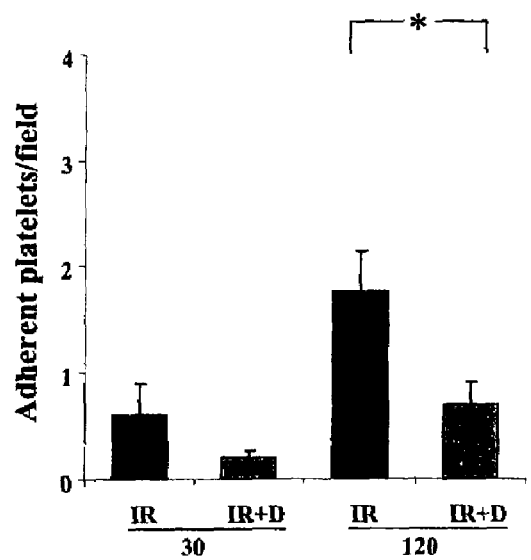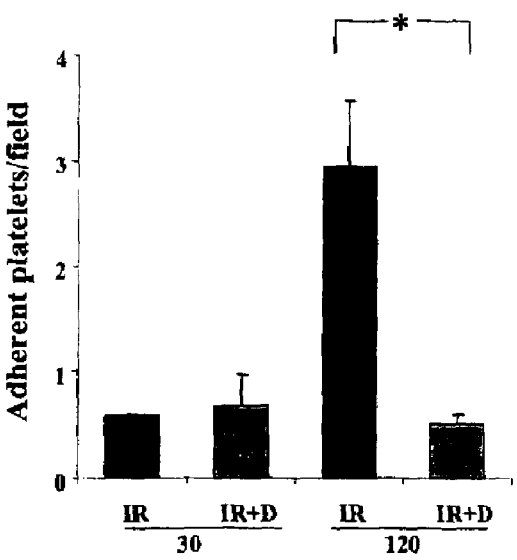
FIG. 7A  FIG. 7B

ATTENUATION OF REPERFUSION INJURY

RELATED APPLICATIONS

This application is a continuation in part of U.S. application Ser. No. 11/486,667, "Modified Annexin Proteins And Methods For Their Use In Platelet Storage And Transfusion," pending, filed Jul. 14, 2006, which application is a continuation in part of U.S. application Ser. No. 11/267,837, "Modified Annexin Proteins for their use in Organ Transplantation," pending, filed Nov. 3, 2005, which is a continuation in part of U.S. application Ser. No. 11/078,231, "Modified Annexin Proteins and Methods for Preventing Thrombosis," pending, filed Mar. 10, 2005, which is a continuation in part of U.S. application Ser. No. 10/080,370, "Modified Annexin Proteins and Methods for Preventing Thrombosis," filed Feb. 21, 2002, now U.S. Pat. No. 6,962,903, issued Nov. 8, 2005, which claims the benefit under 35 U.S.C. §119 of U.S. Provisional Application No. 60/270,402, "Optimizing the Annexin Molecule for Preventing Thrombosis," filed Feb. 21, 2001, now expired, and U.S. Provisional Application No. 60/332,582, "Modified Annexin Molecule for Preventing Thrombosis and Reperfusion Injury," filed Nov. 21, 2001, also expired. U.S. application Ser. No. 11/078,231 also claims the benefit, under 35 U.S.C. §119 of U.S. Provisional application No. 60/552, 428, "The Use Of Modified Annexin To Attenuate Reperfusion Injury," filed Mar. 11, 2004, now expired, and U.S. Provisional application No. 60/579,589 "Use of a Modified Annexin to Attenuate Reperfusion Injury," filed Jun. 14, 2004, also expired. The disclosure of each of the foregoing patent applications is hereby incorporated by reference herein in their entirety.

FIELD OF THE INVENTION

This invention relates generally to attenuation of post-ischemic reperfusion injury (IRI), and more particularly to compositions and methods useful in the attenuation of IRI.

BACKGROUND

Brief (transient) or prolonged restriction of blood flow to an organ or tissue results in ischemia, an insufficient supply of oxygenated blood to that organ or tissue. In a clinical sense, ischemia is typically caused by partial or complete obstruction of a blood vessel, such as by stroke, myocardial infarction, or surgery in which the blood supply to the organ is reduced or cut off. It occurs also when an organ or tissue subject to transplantation or grafting, respectively, becomes ischemic after removal from the body. Reperfusion is the process of restoring blood supply to an organ or tissue after an event that restricts or blocks blood flow, for example by removal or lysis of a thrombus. Reperfusion also occurs following organ transplantation when the circulation is re-established.

Transient ischemia produces reversible injury in many organs. However, re-establishment of the circulation is associated with pathological changes that exacerbate tissue damage, and is typically referred to as IRI. This type of injury significantly reduces the success of recovery from stroke, myocardial infarction, organ transplantation and other types of surgery.

IRI is a complex process and the underlying pathogenetic mechanisms are not fully understood. Several earlier experimental animal and clinical studies, however, provide insight on the subject. For example, myocardial infarctions in rabbit hearts (Farb et al. J. Am. Coll. Cardiol. 1993; 21: 1295) and human hearts (Nijmeier et al. Int. Immunopharmacol. 2001; 1: 403) provide a model of IRI: myocytes are viable before reperfusion then progress to irreversible injury during reperfusion. Apoptosis can contribute to myocardial cell death during reperfusion, demonstrated by the finding that caspase inhibition protects against lethal reperfusion injury (Mocanu et al., Br. J. Pharmacol. 2000; 130: 197). IRI is also lessened when leukocytes are depleted (references in Nijmeijer et al., 2001).

Phospholipids are asymmetrically distributed in the plasma membrane bilayer of normal cells. The acidic phospholipid phosphatidylserine (PS) is confined to the inner layer facing the cytoplasm (Devaux and Zachowski, Chem. Phys. Lipids 1994; 73: 107) and maintained in this orientation by an ATP-dependent phospholipid translocase. When ATP is depleted (for example, as a result of anoxia) some PS translocates to the outer layer and is accessible on the cell surface. This process has been assayed by flow cytometry using a fluorescently labeled protein that binds PS with high affinity, such as labeled annexin V (Bossy-Wetzel and Green, Methods Enzymol. 2000; 322: 15).

Even though many advances have been made in surgical technique, patient management, and immunosuppression, IRI remains an important clinical problem. IRI accounts for as much as 10% of early graft loss in the case of transplanted livers (Amersi et al., J. Clin. Invest. 1999; 104: 1631). In addition, preservation of livers longer than 12 hours is highly correlated with primary nonfunction after transplantation, as well as an increased incidence of both acute and chronic rejection (Fellstrom et al., Transplant Proc. 1998; 30: 4278).

In spite of extensive research, including that reviewed by Selzner et al. (Gastroenterology 2003; 125: 917), no method for decreasing IRI has become widely used in the treatment of stroke or myocardial infarction, or in organ transplantation or tissue grafting. It would be desirable to develop a therapeutic agent or procedure which attenuates or prevents IRI from stroke or myocardial infarction, following organ transplantation, and in other surgical procedures.

d'Amico et al. (FASEB J. 2000; 14: 1867) mention that annexin V did not inhibit RI in the rat heart whereas lipocortin I (annexin I) did.

Pelton et al. (J. Exp. Med. 1991; 174: 305) mention that a fragment of lipocortin I, injected into the cerebral ventricle of rats, decreased infarct size and cerebral edema after cerebral ischemia.

Against this background, the present disclosure is provided.

SUMMARY

The present invention provides compositions for and methods of attenuating and/or preventing IRI in a patient in need thereof, or in an organ or tissue in need thereof.

There is provided novel compositions for attenuating and/or preventing IRI in a patient in need thereof.

There is provided novel compositions for attenuating and/or preventing IRI in an organ or tissue in need thereof.

The above compositions comprise an agent that binds with high affinity to PS on cell surfaces. In some embodiments, the agent is a protein or other ligand to PS, such as an annexin or modified annexin, a monoclonal or polyclonal antibody to PS, an antibody fragment or construct binding PS, or another class of molecule found to have affinity for PS.

There is also provided a method of attenuating IRI comprising the administration of a PS binding agent to a patient in need thereof.

There is also provided a method of preventing or limiting IRI comprising administering to an organ transplant recipient a therapeutic composition that comprises a PS binding agent.

There is further provided a method of preventing IRI to isolated cells or groups of cells comprising adding PS binding agent to the isolated cells or groups of cells.

There is still further provided a method of protecting an organ or a tissue susceptible to IRI comprising contacting the organ or tissue with a PS binding agent.

Further features and benefits of the invention will be apparent to one skilled in the art from a reading of this specification.

BRIEF DESCRIPTION OF THE DRAWINGS

FIGS. 1A-C show the structural scheme of two modified annexin embodiments. FIG. 1A shows the structural scheme of human annexin V homodimer with a His-tag; FIG. 1B shows the structural scheme of the human annexin V homodimer without a His-tag. FIG. 1C shows a DNA construct for making a homodimer of annexin V.

FIG. 4 shows PLA$_2$-induced hemolysis of PS-exposing RBC. A mixture of normal ($1 \times 10^7$/ml) and PS exposing ($1 \times 10^7$/ml) RBCs was incubated with 100 ng/ml pancreatic PLA$_2$ (pPLA$_2$) or secretory PLA$_2$ (sPLA$_2$). Hemolysis was measured as a function of time and expressed relative to 100% hemolysis induced by osmotic shock. The percentage of PS-exposing cells was determined by flow cytometry of the cell suspension after labeling with biotinylated DAV and R-phycoerythrein-conjugated streptavidin. FIG. 4A shows hemolysis induced by 100 ng/ml pPLA$_2$ in absence (triangles) or presence of 2 µg/ml DAV (circles) or AV (squares). FIG. 4B shows hemolysis induced by 100 ng/ml pPLA$_2$ in the presence of various amounts of DAV (circles) or AV (squares). FIG. 4C shows PS-exposing cells in the cell suspension after 60 minutes incubation with 100 ng/ml pPLA$_2$ in the presence of 2 µg/ml DAV.

FIG. 6A shows attachment of leukocytes to endothelial cells during IRI with and without Diannexin for periportal sinusoids. FIG. 6B shows attachment of leukocytes to endothelial cells during IRI with and without Diannexin for centrilobular sinusoids.

FIG. 7A shows attachment of platelets to endothelial cells during ischemia-reperfusion injury with and without Diannexin for periportal sinusoids. FIG. 7B shows attachment of platelets to endothelial cells during ischemia-reperfusion injury with and without Diannexin for centrilobular sinusoids.

Figure 2A:
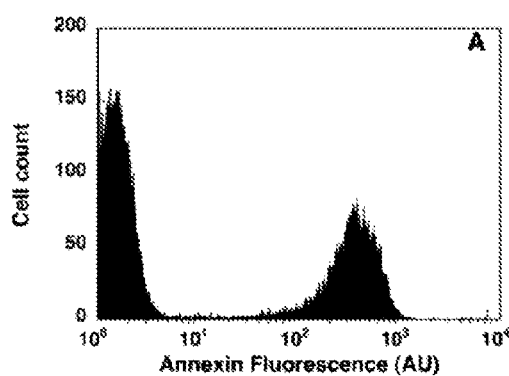
FIGS. 2A-D show the results of flowcytometric analysis of a mixture of normal ($1 \times 10^7$/ml) and PS exposing ($1 \times 10^7$/ml) RBCs incubated with 0.2 µg/ml biotinylated AV (FIG. 2A); 0.2 µg/ml nonbiotinylated DAV (FIG. 2B); 0.2 µg/ml biotinylated AV and 0.2 µg/ml nonbiotinylated DAV (FIG. 2C); and 0.2 µg/ml biotinylated DAV and 0.2 µg/ml nonbiotinylated AV (FIG. 2D), in each case, followed by R-phycoerythrein-conjugated streptavidin.
Figure 2B:
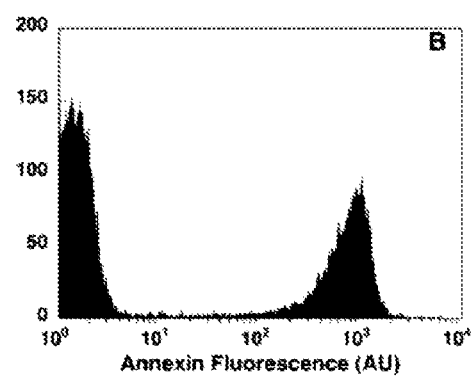
Figure 2C:
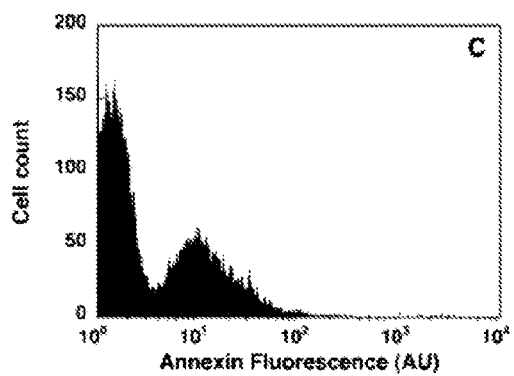
Figure 2D:
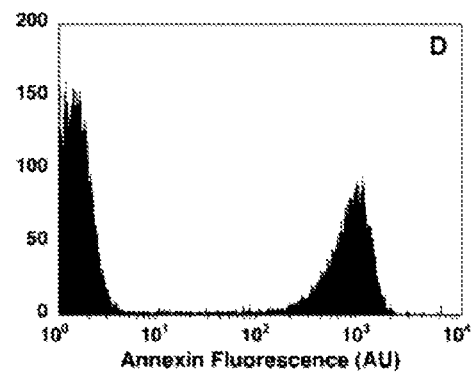

The Figures form part of the present specification and are included to further demonstrate certain aspects of the present invention. The invention may be better understood by reference to one or more of these drawings in combination with the detailed description of specific embodiments presented herein.

DETAILED DESCRIPTION

Embodiments of the present invention provide compositions for and methods of attenuating or preventing IRI in the context of stroke, myocardial infarction, organ transplantation, tissue grafting, and surgery which restricts or cuts off blood supply to an organ or tissue.

Compositions

Provided herein are pharmaceutical compositions comprising one or more agents that bind PS on cell surfaces (referred to herein as "PS binding agents"), and a pharmaceutically acceptable carrier. Such pharmaceutical compositions can be added to cells, groups of cells, tissues, or organs, and/or administered to patients. These compositions can be used according to the methods described herein, for example, to attenuate and/or prevent IRI in a patient in need thereof.

Methods of Treatment

Provided herein are methods of attenuating IRI comprising the administration of one or more PS binding agents to a patient in need thereof.

The word "attenuating" as used herein is defined as decreasing or otherwise reducing, and includes preventing and partially reversing. As applied herein, attenuating IRI has, in some instances, the effect of decreasing and/or reducing this type of injury. In other instances, attenuating IRI has the effect of partially reversing the injury. Partially reversing IRI can occur when administration of PS binding agent reverses damage already resulting from ischemia. Preventing IRI can occur when administration of a PS binding agent prevents any amount, for example, from about 1% to about 100% of possible IRI.

Also provided herein are methods of protecting an organ or a tissue susceptible to IRI comprising contacting the organ or tissue with a PS binding agent.

An organ or tissue susceptible to IRI includes, for example, an organ or tissue which is transplanted, an organ or tissue at risk of ischemia during surgery, brain tissue affected by stroke, and heart tissue affected by myocardial infarction.

Translocation of PS to Cell Surfaces

Hypoxia and subsequent reoxygenation of cultured endothelial cells (EC) results in an increase in the binding of labeled annexin V to a cell's surface (Ran et al., Cancer Res. 2002; 62: 6132). These findings show that PS is translocated to the surface of ECs during hypoxia. Translocation was augmented by the pro-inflammatory cytokines IL-1α and TNFα, and by acidity and oxidant stress, all of which are present under conditions when IRI occurs.

Translocation of PS to the cell surface has been identified as a marker for the early stages of apoptosis. Human studies indicate that apoptosis is implicated in the process of cardiomyocyte death, because apoptotic cells identified by labeled annexin V binding were present in the infarcted area of myocardial samples obtained from patients who died of an acute myocardial infarct (Krijnen et al., 2002, review). The sequence of events involved in reperfusion is proposed to occur as follows: exposure of PS on the surface of ECs that are still viable, and the binding to the ECs of leukocytes and platelets. These events block microvascular blood flow, prolong anoxia and augment the damage resulting from the preceding ischemia.

The contribution of leukocytes to IRI is apparent from studies on monocytes in this process. The chemokine MCP-1 (monocyte chemoattractant protein-1) plays a major part in the recruitment of monocytes. For example, soon after reperfusion begins, MCP-1 messenger RNA is induced in the blood vessels of canine hearts (Kumar et al., Circulation 1997; 95: 693). One hour after reperfusion, there is a substantial recruitment of monocytes into the canine heart (Birdsall et al., Circulation 1997; 97: 684). An antibody against MCP-1 significantly reduced the infarct size 24 hours after ischemia and reperfusion in the rat heart (Ono et al., Lab. Invest. 1999; 79: 195). Transfection with a dominant-negative inhibitor of MCP-1 was found to improve cardiac function after 6 hours of cold preservation (Kajihara et al., Circulation 2003; 108, supp. II: 213). Conversely, overexpression of MCP-1 in the mouse brain increased the recruitment of inflammatory cells and exacerbated ischemic brain injury (Chen et al., J. Cerebral Blood Flow Metab. 2003; 23: 748).

The early stages of apoptosis, including PS translocation to the cell surface, are reversible (Hammill et al., Exp. Cell Res. 1999, 251: 16; Jeangirard et al., J. Immunol. 1999, 162, 5712). Binding of monocytes or other phagocytic cells to such pre-apoptotic cells can initiate the later, irreversible stages of apoptosis. The role of phagocytic cells in apoptosis was revealed by genetic studies in *Caenorhabiditis elegans*. Programmed cell death in *C. elegans* requires an interaction of target cells with phagocytic cells. Although engulfment usually follows, changes characteristic of apoptosis, e.g., the generation of free DNA 3'-hydroxyl ends, can occur without phagocytosis (Wu et al., Genes Develop. 2000; 14: 536). Mutations in either target cells or phagocytic cells prevent apoptosis (Reddien et al., Nature 2001; 412: 198). Apoptosis in mammalian cells follows a similar sequence. Reddien et al. conclude that phagocytic cells promote the suicides of many (and perhaps all) cells triggered to initiate programmed cell death. This concept may be extended to postulate that recruited monocytes trigger the later stages of apoptosis in ECs and other cell types during IRI.

As discussed above, a distinguishing marker of cells in the early stages of apoptosis is the presence of PS on their surface. Activated monocytes and macrophages express surface receptors for PS (Fadok et al., Nature 2000; 405: 85), and these receptors mediate attachment to and phagocytosis of apoptotic cells. However, as in the case of *C. elegans*, the binding of recruited monocytes to ECs and other cells expressing PS may trigger the later stages of apoptosis, including TUNEL positivity and caspase 3 activation, without actual engulfment.

A group of enzymes with phospholipase $A_2$ ($PLA_2$) activity plays an important role in the generation of eicosanoid and other lipid mediators of inflammation, thrombosis, and reperfusion injury. Secretory $PLA_2$ ($sPLA_2$) is released from activated monocytes, as well as other cell types, and is detectable during IRI. Elevated levels of $sPLA_2$ in the circulation are associated with an increased risk for cardiovascular events (Kugiyama et al., Circulation 1999; 10: 1280). Significant elevations of $sPLA_2$ in peripheral blood have been shown in humans with acute myocardial infarction (Nijmeier et al., Int. Immunopharmacol. 2001; 1: 403). $sPLA_2$ acts on membranes or vesicles with externalized PS (Fourcade et al., Cell 1995; 80: 919) to generate lysophosphatidylcholine (LPC) and lysophosphatidic acid (LPA). LPC is chemotactic for monocytes (Lauber et al., Cell 2003; 113: 717) and could have synergistic effects with MCP-1 in the recruitment of these cells into sites undergoing IRI. LPA induces rounding of EC, which promotes extravasation of proteins and edema (Amerongen et al., Arterioscl. Thromb. Vasc. Biol. 2000; 20:127). LPC also induces $Ca^{2+}$ influx into cardiac myocytes, which may be important in the induction of ventricular arrhythmia following acute myocardial infarction (Hashizume et al., Jpn. Heart J. 1997; 38: 11). LPA binds to several high-affinity G protein (Edg) receptors. Selective blockade of LPA3 receptors reduces murine renal IRI (Okusa et al., Am. J. Physiol. 2003; 285: F565). Another product of $sPLA_2$ activity is arachidonic acid, which accumulates in rat hearts during IRI (van der Vusse et al., Ann. NY Acad. Sci. 1994; 723: 1). Arachidonic acid can itself induce apoptosis and is the precursor of prostaglandins and other lipid mediators, including, for example, thromboxane $A_2$ which can contribute to rethrombosis and vasoconstriction. If ECs are damaged, the effects of thromboxane would not be opposed by prostacyclin and nitric oxide.

Surgery, Stroke, and Myocardial Infarction

By administrating one or more PS binding agents to a patient undergoing surgery, IRI following the operation can be prevented and the organ to which blood supply was restricted or cut off can be protected. Postoperative critical care will decrease because organ or tissue dysfunction is ameliorated or completely avoided. Any type of surgery is contemplated herein, including surgery that involves restriction of blood supply to an organ or tissue. Illustrative surgical procedures that can benefit from the methods described herein include but are not limited to abdominal surgery, abdominoplasty, adenoidectomy, amputation, angioplasty, appendectomy, arthrodesis, arthroplasty, brain surgery, cesarean section, cholecystectomy, colon resection, colostomy, corneal transplantation, discectomy, endarterectomy, gastrectomy, grafting of skin or other tissues, heart transplantation, heart surgery hemicorporectomy, hemorrhoidectomy, hepatectomy, hernia repair, hysterectomy, kidney transplantation, laminectomy, laryngectomy, lumpectomy, lung transplantation, mammoplasty, mastectomy, mastoidectomy, myotomy, nephrectomy, nissen fundoplication, oophorectomy, orchidectomy, orthopedic surgery, parathyroidectomy, penectomy, phalloplasty, pneumonectomy, prostatectomy, radiosurgery, rotationplasty, splenectomy, stapedectomy, thoracotomy, thrombectomy, thymectomy, thyroidectomy, tonsillectomy, ulnar collateral ligament reconstruction, vaginectomy, and vasectomy.

In some instances, IRI is caused by surgery which restricts or cuts off blood supply to a tissue or organ. Here, a PS binding agent, for example, can be administered up to at least about 6 hours prior to surgery, during surgery, and/or up to at least 7 days after surgery.

In other instances, IRI is caused by stroke or myocardial infarction.

According to a World Health Organization estimate 15 million people experience a stroke every year (www-.who.int.). Of these, 5 million die and 5 million are left with permanent disability. Stroke is the third leading cause of death and the leading cause of adult disability in the United States and industrialized European nations, and a major cause of severe, long-term disability. Stroke is an acute neurological injury in which the blood supply to a part of the brain is interrupted, resulting in sudden loss of neuronal function due to disturbance in cerebral perfusion. This disturbance in perfusion is commonly arterial, but can be venous. The area of the brain of the brain where the stroke occurs becomes ischemic and affected tissue can die or be seriously damaged.

In an ischemic stroke, a blood vessel becomes occluded and the blood supply to part of the brain is totally or partially blocked.

Ischemic stroke is generally divided into three categories: thrombotic stroke, embolic stroke, and systemic hypoperfusion (Watershed or Border Zone stroke).

The great majority (nearly 80%) of strokes follow occlusion of a cerebral artery by a thrombus. Thrombotic stroke involves a thrombus build up, often around atherosclerotic plaques, gradually narrowing the lumen of the artery and impeding blood flow to distal tissue. Blockage of the artery is gradual, and the onset of a symptomatic thrombotic stroke may be slower than that of an embolic stroke. A thrombus, even if non-occluding, can lead to an embolic stroke if the thrombus breaks off, becoming an embolus. Cerebral thrombosis produces a central area in which vascular perfusion is severely impaired and results in rapid and irreversible brain damage. Surrounding this infarct is an area where vascular perfusion is reduced. Early restoration of blood flow (reperfusion) can salvage brain tissue in this area, thereby decreasing neurological disability.

Embolic stroke is the blockage of arterial access to a part of the brain by an embolus, a traveling particle or debris in the arterial bloodstream originating outside the brain. An embolus is most frequently a blood clot; however a plaque broken off from an atherosclerotic blood vessel, fat (e.g., from bone marrow in a broken bone), air, or cancerous cells can cause an embolic stroke.

Systemic hypoperfusion, another cause of ischemic stroke, is the reduction of blood flow to all parts of the body, and commonly the result of cardiac pump failure from cardiac arrest or arrhythmias, or from reduced cardiac output during myocardial infarction, pulmonary embolism, pericardial effusion, or bleeding. Because the reduction in blood flow is global, all parts of the brain may be affected, especially border zone regions or "watershed areas" supplied by the major cerebral arteries. Blood flow to the brain during systemic hypoperfusion does not necessarily stop, but may decrease to the point where brain damage occurs.

Two therapies are approved by regulatory authorities to promote reperfusion after stroke: intravenous administration of tissue plasminogen activator, which lyses thrombi, and a mechanical device that allows retrieval of thrombi from within cerebral vessels (Merci Concentric Retriever). A limitation of both these therapies is that during reperfusion vascular permeability can be increased, resulting in edema and consequent impairment of cerebral function (Maier et al. Ann. Neurol. 2006; 59:929-938). An even more serious complication of reperfusion is breakdown of blood vessel integrity, leading to hemorrhage. Post-reperfusion hemorrhage is associated with high morbidity and mortality. An additional complication is re-thrombosis after lysis or removal of the original thrombus.

An alternative method to treat stroke is contemplated herein and comprises the administration of a PS binding agent. In some embodiments, one or more PS-binding agents can, for example, be administered prior to surgery to remove the thrombus, during surgery, during reperfusion, after reperfusion, or any combination thereof. A PS-binding agent can also, for example, be administered to a patient suffering from systemic hypoperfusion, especially while the caregiver is assessing and/or treating the cause of the hypoperfusion.

The therapeutic strategy provided herein can also be used in combination with a thrombolytic agent or mechanical removal of the thrombus. Additional use of a neuroprotective agent, such as erythropoietin or an analog thereof, can further improve recovery following cerebral thrombosis.

Acute myocardial infarction (MI), commonly known as a heart attack, is a disease state that occurs when the blood supply to a part of the heart is interrupted. The resulting oxygen shortage (ischemia) causes damage and potential death of heart tissue. It is the leading cause of death for both men and women all over the world (www.who.int.). The most common triggering event is the disruption of an atherosclerotic plaque in an epicardial coronary artery, which leads to a clotting cascade, and sometimes results in total occlusion of the artery.

To treat MI, a PS binding agent can, for example, be administered in conjunction with thrombolytic drug therapy, or prior to any reperfusion related surgery, including percutaneous coronary intervention or coronary artery bypass surgery. A PS-binding agent can also, for example, be administered anytime after signs or symptoms of MI are apparent. In some instances, this is within at least about 12 hours of the MI event, for example, within at least about 10 hours, or within at least about 8 hours, or within at least about 6 hours of the MI event.

Organ Transplants and Tissue Grafting

In some instances, IRI is caused by organ transplantation. In other instances, IRI is caused by tissue grafting. In either situation, a PS binding agent can, for example, be administered to a transplant or graft recipient up to at least about 6 hours prior to reperfusion, up to at least about 3 hours prior to reperfusion, up to at least about 1 hour prior to reperfusion, during reperfusion, and/or up to at least about 1 hour after commencing reperfusion.

A transplanted organ is typically recovered from a donor and perfused with a saline solution or placed in such a solution. The University of Wisconsin solution originally introduced by Belzer et al. is one such solution (Transplantation 1988; 45: 673). The organ is then preserved on ice for several hours while being transported to the recipient patient. During this period the organ is anoxic, ATP is depleted, and phospholipid asymmetry in the plasma membrane of endiothelial cells (ECs) and other cell types is lost. Under normal conditions an ATP-dependent phospholipid translocase maintains this asymmetry, confining PS to the inner leaflet of the plasma membrane bilayer. Following anoxia, PS is translocated to the outer leaflet of the EC plasma membrane, as demonstrated by annexin V binding to the surface of anoxic cultured cells (Ran et al. Cancer Res. 2002; 62: 6132). We provide herein that the loss of phospholipid asymmetry in ECs and other cells is a major event in the pathogenesis of IRI. The PS exposed on the surfaces of ECs promotes the attachment to them of leukocytes and platelets, which obstructs microvascular blood flow. The binding to ECs of activated monocytes can then trigger the terminal sequence of apoptotic events in ECs. Impairment of blood flow to target organ cells, such as hepatocytes or cardiomyocytes, leads to their death by apoptosis and/or necrosis.

Generally, the methods provided herein comprise protecting an organ or tissue susceptible to reperfusion injury by contacting the organ with a PS binding agent. For example, an organ or tissue can be contacted with a PS binding agent, e.g., modified annexin protein, by intravenously administering about 10 to 1000 µg/kg of the PS binding agent to a patient who has an organ or tissue susceptible to IRI, even if the organ is a transplanted fatty liver.

Organ transplantation permits survival of patients who would otherwise die of heart, liver, or lung disease, and provides an improved quality of life for patients on renal dialysis.

Because there is a shortage of organs for transplantation, it would be advantageous if organs from non-ideal, extended-criteria donors could be transplanted successfully. Pretransplant correlates of diminished graft survival include advanced donor age, long-standing donor hypertension or diabetes mellitus, non-heartbeating cadaver donors and prolonged cold preservation time (A. O. Ojo et al. J. Am. Soc. Nephrol. 2001; 12: 589). The outcome of liver transplants is less successful if the donor organs are steatotic (Amersi et al., Proc. Natl. Acad. Sci. U.S.A. 2002; 99: 8915), a common occurrence especially among ageing donors.

The methods and compositions provided herein are therefore useful to increase the percentage of successful organ transplants and tissue grafts, to prolong graft and patient survival, and to increase the pool of candidate donor organs. As the number of patients who might benefit from organ transplantation greatly exceeds the number of organs available, an increased likelihood of a successful transplant would increase the quality of life, add years to a transplant patient's lifespan, and ultimately save lives. It will also reduce the need for hospital care, and consequent costs.

By administering a PS binding agent to a recipient of an organ transplant at time of transplantation or shortly afterwards, development of IRI in the transplanted organ can be attenuated or prevented. As a result, the function of the transplanted organ is more rapidly recovered, a prerequisite for the success of the organ transplantation. In kidney transplantation, the prevention of renal dysfunction after transplantation decreases dependence of the patient on hemodialysis. In liver, heart, and lung transplantations, the early proper function of the transplanted organ is critical to decreasing morbidity and mortality of the patients. By adding a PS binding agent to the artificial preservation solution used for organ perfusion and/or for cold storage, IRI in the transplanted organ can also be prevented, the organ protected, and functional recovery after transplantation promoted.

Agents Binding PS on Cell Surfaces

As used herein, a "PS binding agent" is any molecule that binds to PS externalized on cell surfaces and inhibits interaction thereby, for example, interaction between a receptor and PS. In some embodiments, inhibition can occur because the binding agent is bound to PS. In other embodiments, the binding agent is associated with PS. In some aspects, this inhibition restrains or retards physiologic, chemical, or enzymatic action between PS and PS interacting molecules. In other aspects, a binding agent blocks, restricts, or interferes with a particular chemical reaction or other biologic activity. In still other aspects, a binding agent prevents recognition of PS by cells such as leukocytes, monocytes and platelets, thereby preventing interaction between a cell expressing PS and the monocytes, leukocytes and platelets.

According to the compositions and methods herein, the binding agent is a protein or other agent that binds to PS exposed on cell surfaces. Such an agent can be any molecule that binds PS with high affinity or binds some structure on cell surfaces associated with PS, such as a component of lipid rafts. The PS-binding agent can bind PS translocated to the surface of ECs as a result of anoxia, or to PS externalized to the surface of platelets or other cells during their activation. By binding PS on cell surfaces, such an agent can inhibit the attachment to them of other cell types or of some enzymes. An example is the attachment of leukocytes and platelets to ECs during IRI. A second example is the docking and activity of secretory isoforms of $PLA_2$. A third example is the assembly and activity of the prothrombinase complex on PS translocated to the surface of platelets, ECs and other cell types.

Annexins as Agents Binding PS on Cell Surfaces

In some aspects, the PS binding agent is a modified annexin. As used herein, the phrase "modified annexin" refers to any annexin protein that has been modified in such a way that its half-life in a recipient is prolonged. Modified annexin refers to the subject matter disclosed in U.S. patent application Ser. No. 11/267,837, which is incorporated by reference in its entirety.

The clearance rate of proteins from circulation into the urine primarily depends on the molecular weight of the protein. When the clearance rate of a naturally occurring protein is compared with the clearance rate of the same protein conjugated with polyethylene glycols of different chain lengths, effectively increasing their molecular weight, a decrease in renal clearance is demonstrated at about 70 kD, the well-established renal threshold (Knauf et al., J. Biol. Chem. 1988; 263: 15064). For example, the half-life of annexin V (36 kDa) in the circulation of cynomolgus monkeys was found to be less than 15 minutes (Romisch et al. Thromb. Res. 1991; 61: 93). The protein passes rapidly from the circulation into the kidneys (Thiagarajan et al., Circulation 1997; 96: 2339). As shown below in Example 3, the terminal half-life of Diannexin (a modified annexin having two annexin proteins attached with a novel linker protein) in the rat was found to be about 5 hours by $^{125}$I labeling and 2.5 hours by ELISA. In cynomolgus monkeys the terminal half-life of Diannexin in circulation, assayed by ELISA, was about 5 hours. The use of annexin proteins as therapeutic agents can require in some instances an increase in the molecular weight of the protein to prolong its survival in the circulation and increase its therapeutic efficacy.

Annexins include proteins of the annexin family, such as Annexin I, Annexin II (lipocortin 2, calpactin 1, protein I, p36, chromobindin 8), Annexin III (lipocortin 3, PAP-III), Annexin IV (lipocortin 4, endonexin I, protein II, chromobindin 4), Annexin V (Lipocortin 5, Endonexin 2, VAC-alpha, Anchorin CII, PAP-I), Annexin VI (Lipocortin 6, Protein III, Chromobindin 20, p68, p70), Annexin VII (Synexin), Annexin VIII (VAC-beta), Annexin XI (CAP-50), and Annexin XIII (USA).

An annexin gene includes all nucleic acid sequences related to a natural annexin gene such as regulatory regions that control production of the annexin protein encoded by the gene (such as, but not limited to, transcription, translation, or post-translation control regions) as well as the coding region itself. An annexin gene in accordance to the disclosure herein includes allelic variants. An allelic variant is a gene that occurs at essentially the same locus in the genome, but which, due to natural variations caused by, for example, mutation or recombination, has a similar but not identical sequence. Allelic variants typically encode proteins having similar activity to that of the protein encoded by the gene to which they are being compared. Allelic variants are well known to those skilled in the art and would be expected to be found within a given human since the genome is diploid and/or among a population comprising two or more humans.

In more detail, Annexin I is a 37 kDa member of the annexin superfamily of proteins. The protein is predominantly expressed within gelatinase granules of neutrophils and is externalized onto the cell membrane after cell adhesion to endothelial cells.

Annexin III is also called "lipocortin 3" or "placental anticoagulant protein 3" and is a member of the lipocortin/annexin family. Annexin III binds to phospholipids and membranes in a $Ca^{2+}$ dependent manner and has been shown to have anticoagulant and anti-phospholipase $A_2$ properties.

Suppression of Annexin III expression has been shown to inhibit DNA synthesis in rat hepatocytes (Nimmi, et al., Biol. Pharm. Bull. 2005; 28:424).

Annexin IV (endonexin) is a 32 kDa, $Ca^{2+}$-dependent membrane-binding protein which shares many of the properties of Annexin V. The translated amino acid sequence of Annexin IV shows the four domain structure characteristic of proteins in this class. Annexin IV is a close structural homologue of Annexin V and has 45-59% identity with other members of its family, sharing a similar size and exon-intron organization. The sequence of Annexin IV is shown in Hamman et al., Biochem. Biophys. Res. Comm., 156:660-667. (1988). Isolated from human placenta, Annexin IV encodes a protein that has in vitro anticoagulant activity, binds acidic phospholipid membranes in the presence of calcium, and inhibits phospholipase $A_2$ activity. Annexin IV is almost exclusively expressed in epithelial cells.

Annexin V is a member of the $Ca^{2+}$-dependent phospholipid-binding proteins. It binds to PS with high affinity. The core domain is a concave discoid structure that can be closely apposed to phospholipid membranes. It contains 4 subdomains, each consisting of a 70 amino-acid annexin repeat made up of five alpha-helices. The sequence of annexin V is well known (See Funakoshi et al., 1987; 26:8087).

Annexin VIII belongs to the family of $Ca^{2+}$-dependent phospholipid binding proteins (annexins) having high sequence identity to Annexin V (56%) (Hauptmann, et al., Eur. J. Biochem. 1989; 185(1):63-71). Initially isolated as a 2.2 kb vascular anticoagulant-beta, annexin VIII is neither an extracellular protein nor associated with the cell surface, and may not play a role in coagulation. Annexin VIII is expressed at low levels in human placenta and shows restricted expression in lung, vascular ECs, skin, liver, and kidney.

In aspects of the invention, Annexin V homodimers have the capacity to bind externalized PS located on cell surfaces. Similar properties can be predicted for other annexin homodimers, annexin heterodimers, annexin heterotetramers, or annexins coupled to additional non-annexin proteins.

In some aspects, annexin proteins are modified to increase their half-life in humans or other mammals. In some embodiments, the annexin protein is annexin V, annexin IV or annexin VIII. One suitable modification of annexin is an increase in its effective size, which inhibits loss of the modified annexin, i.e., from the vascular compartment, into the extravascular compartment and urine, thereby prolonging the annexin activity in the vascular compartment. Any increase in effective size of the annexin protein that maintains a sufficient binding affinity with PS is contemplated herein.

In one embodiment, an annexin protein is coupled to one or more annexin proteins (homodimers, heterodimers, etc.) or to one or more non-annexin proteins. Modification can be accomplished through a fusion segment, or by the Fc portion of an immunoglobulin. An alternative method for increasing the effective size of proteins is coupling to polyethylene glycol (PEG) or another molecule. For example, coupling by pegylation is achieved by coupling one or more PEG chains to one or more annexin proteins. A PEG chain can have a molecular weight of at least about 10 kDa, or at least about 20 kDa, or at least about 35 kDa. The annexin is coupled to PEG in such a way that the modified annexin is capable of performing the function of annexin binding to PS on cell surfaces.

According to some embodiments, modified annexin proteins and mixtures thereof are used in methods for preparing pharmaceutical compositions intended for use in any of the therapeutic methods of treatments described above.

In one embodiment, a modified annexin contains a recombinant human annexin protein coupled to PEG in such a way that the modified annexin is capable of performing the function of annexin in a phosphatidylserine (PS)-binding assay. The activity of the intravenously administered annexin-PEG conjugate is prolonged as compared with that of the free or non-modified annexin. The recombinant annexin protein coupled to PEG can be annexin V protein or another annexin protein. In one embodiment, the annexin protein is annexin V, annexin IV or annexin VIII.

PEG consists of repeating units of ethylene oxide that terminate in hydroxyl groups on either end of a linear or, in some cases, branched chain. The size and molecular weight of the coupled PEG chain depend upon the number of ethylene oxide units it contains, which can be selected. Any size of PEG and number of PEG chains per annexin molecule can be used such that the half-life of the modified annexin is increased, relative to annexin, while preserving the function of binding of the modified molecule to PS. The optimal molecular weight of the conjugated PEG varies with the number of PEG chains. In one embodiment, two PEG molecules of molecular weight of at least about 15 kDa, are each coupled to an annexin molecule. The PEG molecules can be linear or branched. The $Ca^{2+}$-dependent binding of annexins to PS is affected not only by the size of the coupled PEG molecules, but also the sites on the protein to which PEG is bound. Optimal selection ensures that desirable properties are retained. Selection of PEG attachment sites is facilitated by knowledge of the three-dimensional structure of the molecule and by mutational and crystallographic analyses of the interaction of the molecule with phospholipid membranes (Campos et al., Biochemistry 37:8004-8008 (1998), incorporated herein by reference).

PEG derivatives have been widely used in covalent attachment (referred to as pegylation) to proteins to enhance solubility, as well as to reduce immunogenicity, proteolysis, and kidney clearance. The superior clinical efficacy of recombinant products coupled to PEG is well established. For example, PEG-interferon alpha-2a administered once weekly is significantly more effective against hepatitis C virus than three weekly doses of the free interferon (Heathcote et al., N. Engl. J. Med. 343:1673-1680 (2000), incorporated herein by reference). Coupling to PEG has been used to prolong the half-life of recombinant proteins in vivo (Knauf et al., J. Biol. Chem. 266:2796-2804 (1988), incorporated herein by reference), as well as to prevent the enzymatic degradation of recombinant proteins and to decrease the immunogenicity sometimes observed with homologous products (references in Hermanson, Bioconjugate techniques. New York, Academic Press (1996), pp. 173-176, incorporated herein by reference).

In another embodiment, the modified annexin protein is a polymer of annexin proteins that has an increased effective size. It is believed that the increase in effective size results in prolonged half-life in the vascular compartment and prolonged activity. One such modified annexin is a dimer of annexin proteins. In one embodiment, the dimer of annexin is a homodimer of annexin V, annexin IV or annexin VIII. In another embodiment, the dimer of annexin is a heterodimer of annexin V and other annexin protein (e.g., annexin IV or annexin VIII), annexin IV and another annexin protein (e.g., annexin V or annexin VIII) or annexin VIII and another annexin protein (e.g., annexin V or annexin IV). The annexin homopolymer or heteropolymer can be produced by bioconjugate methods or recombinant methods, and be administered by itself or in a PEG-conjugated form.

One or more fusion segments can be used to couple one or more annexin proteins, typically referred to as "fusion proteins". A "fusion protein" refers to a first protein having attached one or more additional proteins. The protein can be fused using recombinant DNA techniques, such that the first and second proteins are expressed in frame.

Inclusion of a fusion sequence as part of a modified annexin nucleic acid molecule can enhance stability during production, storage, and/or use of the protein encoded by the nucleic acid molecule. The fusion segment can be a domain of any size that has the desired function. Fusion segments can be constructed to contain restriction sites to enable cleavage for recovery of desired proteins.

In some embodiments, the modified annexins have increased affinity for PS. As described in Example 1, a homodimer of human annexin V (DAV) was prepared using well-established methods of recombinant DNA technology. The annexin molecules of the homodimer are joined through peptide bonds to a flexible linker (FIG. 1).

In other embodiments, the flexible linker contains a sequence of amino acids flanked by a glycine and a serine residue at either end to serve as swivels. Such swivels allow rotation of each annexin monomer around the long axis of the linker. The linker can comprise one or more such "swivels." In some aspects, the linker comprises 2 swivels which can be separated by at least 2 amino acids, at least 4 amino acids, at least 6 amino acids, at least 8 amino acids, or at least 10 amino acids. The overall length of the linker can be 5 to 30 amino acids, 5 to 20 amino acids, 5 to 10 amino acids, 10 to 15 amino acids, or 10 to 20 amino acids. The dimer can fold in such a way that the convex surfaces of the monomer, which bind $Ca^{2+}$ and PS, can both gain access to externalized PS. Flexible linkers are known in the art, for example, $(GGGGS)_{(n)}$ (SEQ ID NO: 24) (n=3-4), as well as helical linkers with less flexibility, $(EAAAK)_{(n)}$ (SEQ ID NO: 25) (n=2-5), described in Arai, et al., Proteins. 2004 Dec. 1; 57(4):829-38.

An illustrative linker represented by SEQ ID NO: 28 comprises 14 amino acids with a Gly-Ser sequence on both ends. The linker was designed to have no secondary structure and to allow flexibility and rotation around its length. The particular amino acids of the linker were also chosen for their low immunogenicity. Various linker amino acid sequences and lengths are described in U.S. patent application Ser. No. 11/613,125, filed Dec. 19, 2006 which is incorporated by reference herein in its entirety.

In another embodiment, recombinant annexin is expressed with, or chemically coupled to, another protein such as the Fc portion of immunoglobulin. Such expression or coupling increases the effective size of the molecule, preventing the loss of annexin from the vascular compartment and prolonging its anticoagulant action. Fc refers to both native and mutant forms of the Fc region of an antibody that contain one or more of the Fc region's CH domains, including truncated forms of Fc polypeptides containing the dimerization-promoting hinge region. Fc polypeptides derived from human IgG1 antibody are illustrative polypeptides for use in fusion proteins described herein.

In some aspects, an agent binding PS on cell surfaces is an isolated modified annexin protein. The modified annexin protein can contain annexin I, annexin II, annexin IV, annexin V, or annexin VIII. In some embodiments, the protein is modified human annexin. In some embodiments, the modified annexin contains recombinant human annexin. The terms "isolated" and "biologically pure" do not necessarily reflect the extent to which the protein has been purified. An isolated or biologically pure protein is a protein that has been removed from its natural environment. Typically, "isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature. An isolated modified annexin protein can be obtained from its natural source, can be produced using recombinant DNA technology, or can be produced by chemical synthesis. As used herein, an isolated modified annexin protein can be a full-length modified protein or any homologue of such a protein. It can also be (e.g., for a pegylated protein) a modified full-length protein or a modified homologue of such a protein.

The minimal size of a protein homologue is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protein homologue is from about 12 to about 18 nucleotides in length. There is no limit on the maximal size of such a nucleic acid molecule in that the nucleic acid molecule can include a portion of a gene, an entire gene, or multiple genes or portions thereof. Similarly, the minimal size of an annexin protein homologue or a modified annexin protein homologue is from about 4 to about 6 amino acids in length, with sizes depending on whether a full-length, multivalent (i.e., fusion protein having more than one domain, each of which has a function) protein, or functional portions of such proteins are desired. Annexin and modified annexin homologues as used herein typically have activity corresponding to the natural subunit, such as being able to attenuate or prevent reperfusion injury.

Annexin protein and modified annexin homologues can be the result of natural allelic variation or natural mutation. The protein homologues can also be produced using techniques known in the art, including, but not limited to, direct modifications to the protein or modifications to the gene encoding the protein using, for example, classic or recombinant DNA techniques to effect random or targeted mutagenesis.

Also included in embodiments of the invention are modified annexin protein containing an amino acid sequence that is between at least about 70% and about 100%, for example, at least about 75%, at least about 80%, at least about 85%, at least about 90%, at least about 95%, 96%, 97%, 98%, or at least about 99%, identical to amino acid sequence SEQ ID NO:3, SEQ ID NO:6, SEQ ID NO:12, SEQ ID NO:15, SEQ ID NO:19, SEQ ID NO:23 or a protein encoded by an allelic variant of a nucleic acid molecule encoding a protein containing any of these sequences. Also included is a modified annexin protein comprising more than one of SEQ ID NO:3, SEQ ID NO:6, SEQ ID NO:12, SEQ ID NO:15; SEQ ID NO:19, or SEQ ID NO:23; for example, a protein comprising SEQ ID NO:3 and SEQ ID NO:12 and separated by a linker. The term "identity" as used herein refers to a comparison between pairs of nucleic acid or amino acid molecules. Methods to determine percent identities between amino acid sequences and between nucleic acid sequences are known to those skilled in the art. Methods to determine percent identities between sequences include computer programs such as the GCG® WISCONSIN PACKAGE™ (available from Accelrys Corporation) which uses the algorithm of Smith and Waterman (Adv. Appl. Math. 1981, 2:482-489), the DNA-SIS™ program (available from Hitachi Software, San Bruno, Calif.), the VECTOR NTI® Suite (available from Informax, Inc., North Bethesda, Md.), or the BLAST software available on the NCBI website.

In another embodiment, a modified annexin protein includes an amino acid sequence of at least about 5 amino acids to about the full length protein or about 319 amino acids, for example, at least about 50 amino acids, at least about 100 amino acids, at least about 200 amino acids, at least about 250 amino acids, at least about 275 amino acids, at least about 300 amino acids, or at least about 319 amino acids or the full-length annexin protein, whichever is shorter. In another embodiment, annexin proteins contain full-length proteins, i.e., proteins encoded by full-length coding regions, or post-translationally modified proteins thereof, such as mature proteins from which initiating methionine and/or signal sequences or "pro" sequences have been removed.

A fragment of a modified annexin protein as used herein can contain at least about 5 amino acids to at least about 100 amino acids, for example, at least about 10 amino acids, at least about 15 amino acids, at least about 20 amino acids, at least about 25 amino acids, at least about 30 amino acids, at least about 35 amino acids, at least about 40 amino acids, at least about 45 amino acids, at least about 50 amino acids, at least about 55 amino acids, at least about 60 amino acids, at least about 65 amino acids, at least about 70 amino acids, at least about 75 amino acids, at least about 80 amino acids, at least about 85 amino acids, at least about 90 amino acids, at least about 95 amino acids, or at least about 100 amino acids in length.

In one embodiment, an isolated modified annexin protein contains a protein encoded by a nucleic acid molecule having the nucleic acid sequence SEQ ID NO:4, SEQ ID NO:17 or SEQ ID NO:21. Alternatively, the modified annexin protein contains a protein encoded by a nucleic acid molecule having the nucleic acid sequence SEQ ID NO:1 or by an allelic variant of a nucleic acid molecule having one of these sequences. Alternatively, the modified annexin protein contains more than one protein sequence encoded by a nucleic acid molecule having the nucleic acid sequence SEQ ID NO:1, SEQ ID NO:10, SEQ ID NO:13 or by an allelic variant of a nucleic acid molecule having this sequence.

In one embodiment, an isolated modified annexin protein contains a protein encoded by a nucleic acid molecule having the nucleic acid sequence SEQ ID NO:10 or by an allelic variant of a nucleic acid molecule having this sequence. Alternatively, the modified annexin protein contains more than one protein sequence encoded by a nucleic acid molecule having the nucleic acid sequence SEQ ID NO:10 or by an allelic variant of a nucleic acid molecule having this sequence (e.g., SEQ ID NO:12-linker-SEQ ID NO:12; SEQ ID NO:19).

In another embodiment, an isolated modified annexin protein is a modified protein encoded by a nucleic acid molecule having the nucleic acid sequence SEQ ID NO:13 or by an allelic variant of a nucleic acid molecule having this sequence. Alternatively, the modified annexin protein contains more than one protein sequence encoded by a nucleic acid molecule having the nucleic acid sequence SEQ ID NO:13 or by an allelic variant of a nucleic acid molecule having this sequence (e.g., SEQ ID NO:15-linker-SEQ ID NO:15; SEQ ID NO:23).

In another embodiment, an isolated modified annexin protein contains a protein encoded by a nucleic acid molecule having the nucleic acid sequence SEQ ID NO:1 and a protein encoded by a nucleic acid molecule having the nucleic acid sequence SEQ ID NO:10, or by allelic variants of these nucleic acid molecules (e.g., SEQ ID NO: 3-linker-SEQ ID NO:12 or SEQ ID NO:12-linker-SEQ ID NO:3).

In another embodiment, an isolated modified annexin protein contains a protein encoded by a nucleic acid molecule having the nucleic acid sequence SEQ ID NO:1 and a protein encoded by a nucleic acid molecule having the nucleic acid sequence SEQ ID NO:13, or by allelic variants of these nucleic acid molecules (e.g., SEQ ID NO:3-linker-SEQ ID NO:15 or SEQ ID NO:15-linker-SEQ ID NO:3).

In another embodiment, an isolated modified annexin protein contains a protein encoded by a nucleic acid molecule having the nucleic acid sequence SEQ ID NO:10 and a protein encoded by a nucleic acid molecule having the nucleic acid sequence SEQ ID NO:13, or by allelic variants of these nucleic acid molecules (e.g., SEQ ID NO:12-linker-SEQ ID NO:15 or SEQ ID NO:15-linker-SEQ ID NO:12).

One embodiment includes a non-native modified annexin protein encoded by a nucleic acid molecule that hybridizes under stringent hybridization conditions with an annexin gene. As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., Molecular Cloning: A Laboratory Manual, Cold Spring Harbor Labs Press (1989), incorporated herein by reference. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., Anal. Biochem. 138:267-284 (1984), incorporated herein by reference. In some embodiments, hybridization conditions will permit isolation of nucleic acid molecules having at least about 80% nucleic acid sequence identity with the nucleic acid molecule being used to probe. In other embodiments, hybridization conditions will permit isolation of nucleic acid molecules having at least about 90% nucleic acid sequence identity with the nucleic acid molecule being used to probe. In still other embodiments, hybridization conditions will permit isolation of nucleic acid molecules having at least about 95% nucleic acid sequence identity with the nucleic acid molecule being used to probe.

A modified annexin protein includes a protein encoded by a nucleic acid molecule that is at least about 50 nucleotides and that hybridizes under conditions that allow about 20% base pair mismatch, or under conditions that allow about 15% base pair mismatch, or under conditions that allow about 10% base pair mismatch, or under conditions that allow about 5% base pair mismatch, or under conditions that allow about 2% base pair mismatch with a nucleic acid molecule selected from the group consisting of SEQ ID NO:1, SEQ ID NO:4, SEQ ID NO:10, SEQ ID NO:13, SEQ ID NO:17, SEQ ID NO:21, or a complement of any of these nucleic acid molecules.

As used herein, an annexin gene includes all nucleic acid sequences related to a natural annexin gene such as regulatory regions that control production of the annexin protein encoded by that gene (such as, but not limited to, transcription, translation or post-translation control regions) as well as the coding region itself. In one embodiment, an annexin gene includes the nucleic acid sequence SEQ ID NO:1. In another embodiment, an annexin gene includes the nucleic acid sequence SEQ ID NO:10. In another embodiment, an annexin gene includes the nucleic acid sequence SEQ ID NO:13. In another embodiment, an annexin gene includes the nucleic acid sequence SEQ ID NO:17. In another embodiment, an annexin gene includes the nucleic acid sequence SEQ ID NO:21. It should be noted that since nucleic acid sequencing technology is not entirely error-free, SEQ ID NO:1 (as well as other sequences presented herein), at best, represents an apparent nucleic acid sequence of the nucleic acid molecule encoding an annexin protein.

In another embodiment, an annexin gene can be an allelic variant that includes a similar but not identical sequence to SEQ ID NO:1. In another embodiment, an annexin gene can be an allelic variant that includes a similar but not identical sequence to SEQ ID NO:10. In another embodiment, an annexin gene can be an allelic variant that includes a similar but not identical sequence to SEQ ID NO:13. In another embodiment, an annexin gene can be an allelic variant that includes a similar but not identical sequence to SEQ ID NO:17. In another embodiment, an annexin gene can be an allelic variant that includes a similar but not identical sequence to SEQ ID NO:21. An allelic variant of an annexin gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given human since the genome is diploid and/or among a population comprising two or more humans.

An isolated annexin protein (from which a modified annexin is prepared) can be obtained from its natural source, can be produced using recombinant DNA technology, or can be produced by chemical synthesis. As used herein, an isolated modified annexin protein can contain a full-length protein or any homologue of such a protein. Examples of annexin and modified annexin homologues include annexin and modified annexin proteins in which amino acids have been deleted (e.g., a truncated version of the protein, such as a peptide or by a protein splicing reaction when an intron has been removed or two exons are joined), inserted, inverted, substituted and/or derivatized (e.g., by glycosylation, phosphorylation, acetylation, methylation, myristylation, prenylation, palmitoylation, amidation and/or addition of glycerophosphatidyl inositol) such that the homologue includes at least one epitope capable of eliciting an immune response against an annexin protein. That is, when the homologue is administered to an animal as an immunogen, using techniques known to those skilled in the art, the animal will produce a humoral and/or cellular immune response against at least one epitope of an annexin protein. Annexin and modified annexin homologues can also be identified by their ability to selectively bind to immune serum. Methods to measure such activities are disclosed herein. Annexin and modified annexin homologues also include those proteins that are capable of performing the function of native annexin in a functional assay; that is, are capable of binding to phosphatidylserine or capable of inhibiting binding or interaction of other PS binding molecules with PS.

A modified annexin protein may be identified by its ability to perform the function of an annexin protein in a functional assay. The phrase "capable of performing the function of that in a functional assay" means that the protein or modified protein has at least about 10% of the activity of the natural protein in the functional assay. In other embodiments, it has at least about 20% of the activity of the natural protein in the functional assay. In other embodiments, it has at least about 30% of the activity of the natural protein in the functional assay. In other embodiments, it has at least about 40% of the activity of the natural protein in the functional assay. In other embodiments, it has at least about 50% of the activity of the natural protein in the functional assay. In other embodiments, the protein or modified protein has at least about 60% of the activity of the natural protein in the functional assay. In still other embodiments, the protein or modified protein has at least about 70% of the activity of the natural protein in the functional assay. In yet other embodiments, the protein or modified protein has at least about 80% of the activity of the natural protein in the functional assay. In other embodiments, the protein or modified protein has at least about 90% of the activity of the natural protein in the functional assay. Examples of functional assays are described herein.

An isolated protein can be produced in a variety of ways, including recombinant expression and recovery of annexin protein from a bacterium. One embodiment provides a method to produce an isolated modified annexin protein using recombinant DNA technology. Such a method includes the steps of (a) culturing a recombinant cell containing a nucleic acid molecule encoding a modified annexin protein to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins can be purified using a variety of standard protein purification techniques.

Isolated proteins can be retrieved in "substantially pure" form. As used herein, "substantially pure" refers to a purity that allows for the effective use of the protein in a functional assay.

Another embodiment provides an isolated nucleic acid molecule capable of hybridizing under stringent conditions with a gene encoding a modified annexin protein such as a homodimer of annexin V, a homodimer of annexin IV, a homodimer of annexin VIII, a heterodimer of annexin V and annexin VIII, a heterodimer of annexin V and annexin IV or a heterodimer of annexin IV and annexin VIII. Such a nucleic acid molecule is also referred to herein as a modified annexin nucleic acid molecule. Included is an isolated nucleic acid molecule that hybridizes under stringent conditions with a modified annexin gene. The characteristics of such genes are disclosed herein. As used herein, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a modified annexin gene includes all nucleic acid sequences related to a natural annexin gene, such as regulatory regions that control production of an annexin protein encoded by that gene (such as, but not limited to, transcriptional, translational, or post-translational control regions) as well as the coding region itself. A nucleic acid molecule can be an isolated modified annexin nucleic acid molecule or a homologue thereof. A nucleic acid molecule can include one or more regulatory regions, full-length or partial coding regions, or combinations thereof. The minimal size of a modified annexin nucleic acid molecule is the minimal size capable of forming a stable hybrid under stringent hybridization conditions with a corresponding natural gene. Annexin nucleic acid molecules can also include a nucleic acid molecule encoding a hybrid protein, a fusion protein, a multivalent protein or a truncation fragment.

An isolated nucleic acid molecule can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule can also be produced using recombinant DNA technology (e.g., polymerase chain reaction (PCR) amplification, cloning, etc.) or chemical synthesis. Isolated modified annexin nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the ability of the nucleic acid molecule to encode an annexin protein or to form stable hybrids under stringent conditions with natural nucleic acid molecule isolates.

A modified annexin nucleic acid molecule homologue can be produced using a number of methods known to those skilled in the art (see, e.g., Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures, and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against an annexin protein and/or to function in a clotting assay, or other functional assay), and/or by hybridization with isolated annexin-encoding nucleic acids under stringent conditions.

An isolated modified annexin nucleic acid molecule can include a nucleic acid sequence that encodes at least one modified annexin protein, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a modified annexin protein.

One embodiment provides a modified annexin nucleic acid molecule that is capable of hybridizing under stringent conditions to a nucleic acid strand that encodes at least a portion of a modified annexin protein or a homologue thereof or to the complement of such a nucleic acid strand. A nucleic acid sequence complement of any nucleic acid sequence refers to the nucleic acid sequence of the nucleic acid strand that is complementary to (i.e., can form a complete double helix with) the strand for which the sequence is cited. It is to be noted that a double-stranded nucleic acid molecule for which a nucleic acid sequence has been determined for one strand and represented by a SEQ ID NO, also comprises a complementary strand having a sequence that is a complement of that SEQ ID NO. As such, nucleic acid molecules can be either double-stranded or single-stranded and include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Included is a modified annexin nucleic acid molecule that includes a nucleic acid sequence having at least about 65 percent to about 99% homology, for example, at least about 70 percent, at least about 75 percent, at least about 80 percent, at least about 85 percent, at least about 90 percent, or at least about 95 percent homology with the corresponding region(s) of the nucleic acid sequence encoding at least a portion of a modified annexin protein. Included is a modified annexin nucleic acid molecule capable of encoding a homodimer of an annexin protein or homologue thereof.

Annexin nucleic acid molecules include SEQ ID NO:4 and allelic variants of SEQ ID NO:4, SEQ ID NO:1 and an allelic variants of SEQ ID NO:1, SEQ ID NO:10 and an allelic variants of SEQ ID NO:10; SEQ ID NO:13 and an allelic variants of SEQ ID NO:13; SEQ ID NO:17 and an allelic variants of SEQ ID NO:17; and SEQ ID NO:21 and an allelic variants of SEQ ID NO:21.

Knowing a nucleic acid molecule of a modified annexin protein described herein allows one skilled in the art to make copies of that nucleic acid molecule as well as to obtain a nucleic acid molecule including additional portions of annexin protein-encoding genes (e.g., nucleic acid molecules that include the translation start site and/or transcription and/or translation control regions), and/or annexin nucleic acid molecule homologues. Knowing a portion of an amino acid sequence of an annexin protein allows one skilled in the art to clone nucleic acid sequences encoding such an annexin protein. In addition, a desired modified annexin nucleic acid molecule can be obtained in a variety of ways including screening appropriate expression libraries with antibodies that bind to annexin proteins; traditional cloning techniques using oligonucleotide probes to screen appropriate libraries or DNA; and PCR amplification of appropriate libraries, or RNA or DNA using oligonucleotide primers (genomic and/or cDNA libraries can be used).

Also included herein are nucleic acid molecules that are oligonucleotides capable of hybridizing, under stringent conditions, with complementary regions of other, typically longer, nucleic acid molecules that encode at least a portion of a modified annexin protein. Oligonucleotides can be RNA, DNA, or derivatives of either. The minimal size of such oligonucleotides is the size required to form a stable hybrid between a given oligonucleotide and the complementary sequence on another nucleic acid molecule. Minimal size characteristics are disclosed herein. The size of the oligonucleotide must also be sufficient for the use of the oligonucleotide in accordance with the methods provided herein. Oligonucleotides can be used in a variety of applications including, but not limited to, as probes to identify additional nucleic acid molecules, as primers to amplify or extend nucleic acid molecules or in therapeutic applications to modulate modified annexin production. Such therapeutic applications include the use of such oligonucleotides in, for example, antisense-, triplex formation-, ribozyme- and/or RNA drug-based technologies. Therefore, included herein are such oligonucleotides and methods to modulate the production of modified annexin proteins by use of one or more of such technologies.

Also provided herein is a recombinant vector, including a modified annexin nucleic acid molecule inserted into any vector capable of delivering the nucleic acid molecule into a host cell. Such a vector contains heterologous nucleic acid sequences, that is, nucleic acid sequences that are not naturally found adjacent to modified annexin nucleic acid molecules. The vector can be either RNA or DNA, either prokaryotic or eukaryotic, and typically is a virus or a plasmid. Recombinant vectors can be used in the cloning, sequencing, and/or otherwise manipulating of modified annexin nucleic acid molecules provided herein. One type of recombinant vector, herein referred to as a recombinant molecule and described in more detail below, can be used in the expression of nucleic acid molecules. Some recombinant vectors are capable of replicating in the transformed cell. Nucleic acid molecules to include in recombinant vectors are disclosed herein.

One embodiment provided herein is a method to produce a modified annexin protein by culturing a cell capable of expressing the protein under conditions effective to produce the protein, and recovering the protein. In an alternative embodiment, the method includes producing an annexin protein by culturing a cell capable of expressing the protein under conditions effective to produce the annexin protein, recovering the protein, and modifying the protein by coupling it to an agent that increases its effective size.

In another embodiment, the cell to culture is a natural bacterial cell, and modified annexin is isolated from these cells. In still another embodiment, a cell to culture is a recombinant cell that is capable of expressing the modified annexin protein, the recombinant cell being produced by transforming a host cell with one or more nucleic acid molecules. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules can remain extrachromosomal or can integrate into one or more sites within a chromosome of the transformed (i.e., recombinant) cell in such a manner that their ability to be expressed is retained. Nucleic acid molecules with which to transform a host cell are disclosed herein.

Suitable host cells to transform include any cell that can be transformed and that can express the introduced modified annexin protein. Such cells are, therefore, capable of producing modified annexin proteins after being transformed with at least one nucleic acid molecule. Host cells can be either untransformed cells or cells that are already transformed with at least one nucleic acid molecule. Suitable host cells can include bacterial, fungal (including yeast), insect, animal, and plant cells. Host cells include bacterial cells, with *E. Coli* cells being particularly useful. Alternative host cells are untransformed (wild-type) bacterial cells producing cognate modified annexin proteins, including attenuated strains with reduced pathogenicity, as appropriate.

A recombinant cell can be produced by transforming a host cell with one or more recombinant molecules, each comprising one or more nucleic acid molecules operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. The expression vector is also capable of replicating within the host cell. Expression vectors can be either prokaryotic or eukaryotic, and are typically viruses or plasmids. Expression vectors include any vectors that function (i.e., direct gene expression) in recombinant cells, including in bacterial, fungal, insect, animal, and/or plant cells. As such, nucleic acid molecules can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules. As used herein, a transcription control sequence includes a sequence that is capable of controlling the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells. A variety of such transcription control sequences are known to the art. Transcription control sequences include those which function in bacterial, yeast, insect and mammalian cells, such as, but not limited to, tac, lac, tzp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, Heliothis zea insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences can also include naturally occurring transcription control sequences naturally associated with a DNA sequence encoding an annexin protein. One transcription control sequence is the Kozak strong promotor and initiation sequence.

Expression vectors may also contain secretory signals (i.e., signal segment nucleic acid sequences) to enable an expressed annexin protein to be secreted from the cell that produces the protein. Suitable signal segments include an annexin protein signal segment or any heterologous signal segment capable of directing the secretion of an annexin protein, including fusion proteins. Signal segments include, but are not limited to, tissue plasminogen activator (t-PA), interferon, interleukin, growth hormone, histocompatibility and viral envelope glycoprotein signal segments.

Expression vectors can also contain fusion sequences which lead to the expression of inserted nucleic acid molecules as fusion proteins. Inclusion of a fusion sequence as part of a modified annexin nucleic acid molecule can enhance the stability during production, storage and/or use of the protein encoded by the nucleic acid molecule. Furthermore, a fusion segment can function as a tool to simplify purification of a modified annexin protein, such as to enable purification of the resultant fusion protein using affinity chromatography.

One fusion segment that can be used for protein purification is the 8-amino acid peptide sequence asp-tyr-lys-asp-asp-asp-asp-lys (SEQ ID NO:9).

A suitable fusion segment can be a domain of any size that has the desired function (e.g., increased stability and/or purification tool). One or more fusion segments can be used to join annexin proteins. Fusion segments can be joined to amino and/or carboxyl termini of an annexin protein. Another type of fusion protein is a fusion protein wherein the fusion segment connects two or more annexin proteins or modified annexin proteins. Linkages between fusion segments and annexin proteins can be constructed to be susceptible to cleavage to enable straightforward recovery of the annexin or modified annexin proteins. Fusion proteins can be produced by culturing a recombinant cell transformed with a fusion nucleic acid sequence that encodes a protein including the fusion segment attached to either the carboxyl and/or amino terminal end of an annexin protein.

A recombinant molecule can include at least one of any nucleic acid molecule heretofore described operatively linked to at least one of any transcription control sequence capable of effectively regulating expression of the nucleic acid molecules in the cell to be transformed. A recombinant molecule includes one or more nucleic acid molecules including those that encode one or more modified annexin proteins. Recombinant molecules and their production are described in the Examples section. Similarly, a recombinant cell includes one or more nucleic acid molecules encoding one or more annexin proteins. Recombinant cells include those disclosed in the Examples section.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, deletion of sequences that destabilize transcripts, and use of control signals that temporally separate recombinant cell growth from recombinant protein production during fermentation. The activity of an expressed recombinant protein may be improved by fragmenting, modifying, or derivatizing the resultant protein.

Recombinant cells can be used to produce annexin or modified annexin proteins by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell, when cultured, is capable of producing an annexin or modified annexin protein. Such a medium is typically an aqueous medium comprising assimilable carbohydrate, nitrogen and phosphate sources, as well as appropriate salts, minerals, metals and other nutrients, such as vitamins. The medium may comprise complex, nutrients or may be a defined minimal medium.

Cells can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant annexin proteins may either remain within the recombinant cell; be secreted into the fermentation medium; be secreted into a space between two cellular membranes, such as the periplasmic space in E. coli; or be retained on the outer surface of a cell or viral membrane. Methods to purify such proteins are disclosed in the Examples section.

It is contemplated herein that in areas of reduced blood flow around the initial infarct, the administration of a neuroprotective agent together with a modified annexin protein will improve the preservation of brain function. An example of a small molecule with neuroprotective activity, possibly related to its antioxidant activity, is the antibiotic mircocycline. An example of a protein with neuroprotective activity is erythropoietin (Ehrenreich et al Molec Med 2002; 8:495-505). Derivatives and peptides of erythropoietin also have neuroprotective activity.

Antibodies as Agents Binding PS on Cell Surfaces

In some aspects, the PS binding agent is an antibody capable of recognizing PS on a cell surface. Isolated antibodies are antibodies that have been removed from their natural environment, but the term "isolated" does not refer to the state of purity of such antibodies. The phrase "recognizing" refers to the ability of such antibodies to preferentially bind PS. Binding affinities, commonly expressed as equilibrium association constants, typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays, immunofluorescent antibody assays, immunoelectron microscopy and binding to cells or liposomes with PS on their surfaces.

The term "antibody" refers to a Y-shaped molecule having a pair of antigen binding sites, a hinge region, and a constant region. PS antibodies used according to the methods described herein include polyclonal and monoclonal antibodies. Functional equivalents are also contemplated, including, for example, antibody fragments, genetically-engineered antibodies, single chain antibodies, and chimeric antibodies. Useful antibodies include those generated in an animal to which PS has been administered, then serum or plasma recovered using techniques known to those skilled in the art. Other useful antibodies include those produced by recombinant methods. Antibodies produced against defined antigens can be especially useful as they are not substantially contaminated with antibodies against other substances.

An illustrative monoclonal antibody that can be useful according to the method described herein was generated by Ran et al. to detect cell surface phospholipids on tumor vasculature (Cancer Research, 2002; 62:6132). The 9D2 antibody bound with specificity to PS, as well as to other anionic phospholipids, without requiring the presence of $Ca^{2+}$. Similarly, Ran et al. developed a murine monoclonal antibody, 3G4, to target PS on tumor vasculature which also may be useful according to the method herein (Clin. Cancer Res.

2005; 11:1551). Thus, the 9D2 antibody and the 3G4 antibody are exemplary PS-binding agents.

Other Agents Binding PS on Cell Surfaces

In some embodiments, the binding agent is a ligand having an affinity for PS that is at least about 10% of the affinity of annexin V for PS. Such ligands include, for example, proteins, polypeptides, receptors, and peptides which interact with PS. The ligand can, in some embodiments, be a construct where one or more proteins, polypeptides, receptors, or peptides are coupled to an Fc portion of an antibody. The Fc regions used herein are derived from an antibody or immunoglobulin. It is necessary that the ligand retains the PS-binding property when attached to the Fc portion of an antibody. Exemplary ligands include those described in U.S. Publication No. 2006/0228299 (Thorpe et al.), for example, Beta 2-glycoportein I, Mer, $\alpha_5\beta_3$ integrin and other integrins, CD3, CD4, CD14, CD93, SRB (CD36), SRC, PSOC and PSr, as well as the proteins, polypeptides, and peptides thereof.

The Fc portion and the ligand can be operatively attached such that each functions sufficiently as intended. In some embodiments, two ligands are coupled to an Fc portion such that they form a dimer. As used herein, "Fc" refers to both native and mutant forms of the Fc region of an antibody that contain one or more of the Fc region's CH domains, including truncated forms of Fc polypeptides containing the dimerization-promoting hinge region.

Therapeutic Applications

The PS binding agents of the invention can be administered in the form of a pharmaceutical composition comprising the agent and a pharmaceutically acceptable carrier. Such a composition is sometimes referred to as a "therapeutic composition". Aspects of potential therapeutic compositions useful are as described herein.

PS binding agents effectively prevent interaction of other molecules with PS on cell surfaces. In the methods provided herein, PS-binding agents are used to attenuate or prevent IRI.

Provided herein are therapeutic compositions comprising PS binding agent on cell surfaces, in any form adapted to the chosen route of administration. Such compositions can also include other components such as a pharmaceutically acceptable excipient, an adjuvant, and/or a carrier. For example, a composition can be formulated in an excipient that the patient can tolerate. Illustrative excipients include water, saline, Ringer's solution, dextrose solution, mannitol, Hanks' solution, the University of Wisconsin Belzer solution and other aqueous physiologically balanced salt solutions. Nonaqueous vehicles, such as triglycerides may also be used. Excipients can contain minor amounts of additives, including substances that enhance isotonicity and chemical stability. Examples of buffers include phosphate buffer, bicarbonate buffer, Tris buffer, histidine, citrate, and glycine, or mixtures thereof, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration. The agent can be further combined with or conjugated to specific delivery agents, including targeting antibodies and/or cytokines.

A therapeutically effective amount includes an amount sufficient to prevent, attenuate, or partially reverse IRI. A therapeutically effective amount also includes an amount sufficient to increase the life of the organ transplant or tissue graft. A therapeutically effective amount further includes an amount sufficient to attenuate IRI from stroke or myocardial infarction. A therapeutically effective amount still further includes an amount sufficient to increase the life expectancy of the patient. A therapeutically effective amount should not substantially increase the risk of hemorrhage compared to the risk in the same patient to whom the PS-binding agent has not been given. A therapeutically effective amount can be any amount or dose sufficient to bring about the desired amount of protection from IRI, or the desired attenuation of IRI. This amount can depend, in part, on the agent used in treatment, the frequency and duration of administration, the condition of the organ or tissue, the length of time of ischemia, and whether the tissue or organ was treated before or after grafting or transplantation with the PS-binding agent. Other factors such as the size and health of the patient are known to those skilled in the art and taken into account at the time of administration. It will be understood that recitation herein of a "therapeutically effective" amount herein does not necessarily require that the drug be therapeutically effective if only a single such dose is administered; in some situations repeated administration may be needed to provide effective treatment.

The PS-binding agent can be administered by any method known in the art. The agent can be administered in a single dose, or as several doses, for example, twice a day or in a dosing regimen that covers two or three days or one or more weeks.

Administration of an agent or therapeutic composition can be by any suitable route, including without limitation parenteral (e.g., intravenous, subcutaneous, intrasternal, intramuscular, or infusion techniques), oral, sublingual, buccal, intranasal, pulmonary, topical, transdermal, intradermal, mucosal, ocular, otic, rectal, vaginal, intragastric, intrasynovial, and intra-articular routes. A route such as parenteral that provides systemic delivery is generally desirable. In some aspects, the method comprises intravenous administration of the agent or composition. In other aspects, the method comprises administration by bolus injection. In still other aspects, the method comprises administration by injection or introduction into an intravenous drip.

Pharmaceutical compositions can be in the form of sterile injectable preparations or aerosol sprays allowing absorption through the nasal mucosa or lungs.

For administration by inhalation or aerosol, the compositions can be prepared according to techniques well-known in the art of pharmaceutical formulations. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides and fatty acids (including oleic acid). Solutions or suspensions of the inhibiting agents can be prepared in water or isotonic saline (for example, phosphate buffered saline), optionally mixed with a nontoxic surfactant. Dispersions can also be prepared in glycerol, liquid polyethylene, glycols, DNA, vegetable oils, triacetin, and mixtures thereof. Under ordinary conditions of storage and use, these preparations can contain a preservative to prevent the growth of microorganisms.

The pharmaceutical dosage for injection or infusion can include sterile aqueous solutions, sterile dispersions, or sterile powders, comprising an active ingredient adapted for the extemporaneous preparation of sterile injectable solutions, sterile infusible solutions, or sterile dispersions. In all cases, the ultimate dosage form should be sterile, fluid, and stable under the conditions of manufacture and storage. The liquid carrier or vehicle can be a solvent or liquid dispersion medium comprising, for example, water, ethanol, polyol (including, for example, but not limited to, glycerol, propylene glycol, or liquid polyethylene glycol), vegetable oil, nontoxic glyceryl ester, or suitable mixture thereof. Desired fluidity can be maintained, for example, by the formation of liposomes, by the maintenance of the required particle size (in the case of dispersion), or by the use of nontoxic surfactants. Prevention of microbial action can be achieved by using various antibacterial and antifungal agents. Illustrative antimicrobial or antifungal agents include parabens, chlorobutanol, phenol, sorbic acid, thimerosal, etc. In some aspects, isotonic agents are desirable, and include sugar, buffer, or sodium chloride.

One embodiment is a controlled release formulation that is capable of slowly releasing a composition into a patient. As used herein, a controlled release formulation comprises a composition as described herein in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations include liquids that, upon administration to a patient, form a solid or a gel in situ. In some embodiments, the controlled release formulations are biodegradable (i.e., bioerodible). Prolonged absorption of injectable compositions can be brought about by the inclusion in the composition of agents delaying absorption, for example, aluminum monostearate hydrogels and gelatin.

Sterile injectable solutions are prepared by incorporating the compounds in the required amount in the appropriate solvent with various other ingredients as enumerated above. Such solutions are subsequently sterilized, typically using a filter. Sterile powders used in the preparation of sterile injectable solutions are vacuum dried or freeze dried, yielding a powder of the active ingredient plus any additional desired ingredient present in the previously sterile-filtered solutions.

In some embodiments the PS-binding agent is a modified annexin protein which can be administered in a range of about 50 to about 500 µg/kg, for example, about 200, or about 300, or about 400 µg/kg. (µg PS-binding agent/kg of patients weight). Modified annexin proteins are shown herein to attenuate IRI in organ transplantation, even in the case of a donor with a fatty liver. The ability to attenuate IRI in the case of a steatotic liver transplant will increase the number of livers considered suitable for use.

A patient can be non-human or human. In some instances the patient is a human patient who has been selected for an organ transplant or tissue graft. In other instances, the patient is a human patient undergoing surgery in which the blood supply to a tissue or organ is cut off or restricted. In still other instances, the patient is a human patient at risk for or suffering from a stroke or myocardial infarction. The phrase "a patient in need" refers to a patient at risk of IRI or having an IRI event. The therapeutic composition that comprises PS binding agent can be administered to a patient before, during, and/or after transplantation, grafting, surgery, myocardial infarction, or stroke.

Thus, further provided is a method of preventing IRI comprising administering to an organ transplant recipient a therapeutic composition that comprises a PS binding agent.

Also provided is a method of preventing reperfusion injury to an isolated cell or group of cells, the method comprising adding a PS-binding agent to a therapeutic composition. As described above, ischemia is the result of anoxic conditions and can be brought about, for example, by removal of an organ or tissue from a donor or donor site, or by stroke, myocardial infarction, or surgery. Thus, an ischemic cell is one that has had its blood supply cut off or restricted. In some aspects of this embodiment, addition of a PS-binding agent to a therapeutic composition inhibits interaction with PS on an ischemic cell or isolated cell or group of cells, such as an isolated pancreatic islet. In other aspects of this embodiment, addition of a PS-binding agent to a therapeutic composition inhibits monocyte recognition of PS on the surface of ECs.

In one embodiment, IRI is caused by organ transplantation. Here, the therapeutic composition containing the PS-binding agent is contacted with a donor organ, for example, up to about 3 hours prior to reperfusion, or up to about 1 hour after the onset of reperfusion. The therapeutic composition can also be contacted with a donor organ prior to removal of the organ from the donor.

In another embodiment, IRI is caused by tissue grafting. In this case, the therapeutic composition containing the PS-binding agent is contacted with a donor tissue up to about 6 hours prior to reperfusion, for example, up to about 3 hours prior to reperfusion, or up to about 1 hour after the onset of reperfusion. Because donor tissues are often removed from one area and grafted in another on the same patient, the therapeutic composition can be contacted with the donor tissue by administering the composition directly to the patient. Alternatively or additionally, the donor tissue can be contacted by the therapeutic composition after excision or by administration to both the recipient prior to removal of the donor tissue and to the excised tissue prior to tissue grafting.

In yet another embodiment, IRI is caused by surgery, for example, gastrointestinal surgery. Here the therapeutic composition containing the PS-binding agent is administered to a patient before, during, and/or after surgery.

In some aspects, the therapeutic composition is a preservation fluid, a perfusion fluid, a rinse solution, or an intravenous drip solution. In other aspects, the therapeutic composition is formulated for bolus injection.

Accordingly, in one embodiment, to protect ischemic or isolated cells, or groups of cells, from IRI a PS-binding agent is added to the preservation fluid used for in situ organ perfusion and cooling (before the organ is removed from a donor) and for cold storage or perfusion after the organ is harvested. The organ or tissue transplant can be perfused or flushed with a solution containing a PS-binding agent. Typically, the organ or tissue is perfused with a solution containing, in addition to the PS-binding agent, components such as electrolytes and cell-protecting agents.

Illustratively, the present inventors added Diannexin (an exemplary PS-binding agent) to the University of Wisconsin solution mentioned above. This solution was then used to perfuse rat livers at two time points: (1) before overnight storage at 4° C., and (2) just after transplantation. These experiments demonstrated that Diannexin protected organs from IRI after transplantation. Though shown to be effective in liver, adding a PS-binding agent to therapeutic compositions can also benefit other transplanted organs including kidneys, hearts, lungs, pancreases, intestines, etc.

A PS binding agent can be added to different types of preservation solutions typically containing electrolytes (such as $Na^+$, $K^+$, $Mg^{++}$, $Cl^-$, $SO_4^2$, $HPO_4^{2-}$, $Ca^{2+}$, and $HCO_3^-$) and may contain additional agents to protect cells during cold storage.

Suitable intracellular preservation solutions include the University of Wisconsin Belzer solution. This solution contains 50 g/l hydroxyethyl starch, 35.83 g/l lactobionic acid, 3.4 μl potassium phosphate monobasic, 1.23 g/l magnesium sulfate heptahydrate, 17.83 g/l raffinose pentahydrate, 1.34 g/l adenosine, 0.136 g/l allopurinol, 0.922 g/l glutathionine, 5.61 g/l potassium hydroxide, and sodium hydroxide (to adjust solution to pH 7.4). The Euro-Collins solution is also suitable for use with the methods and compositions described herein, and contain 2.05 g/l mono-potassium phosphate, 7.4 g/l dipotassium phosphate, 1.12 g/l potassium chloride, 0.84 g/l sodium bicarbonate, and 35 g/l glucose. Other intracellular preservation solutions are envisioned to be within the scope of the present disclosure.

Similarly, a PS binding agent can be added to extracellular type preservation solutions. An illustrative extracellular type preservation solution is PEFADEX (Vitrolife, Sweden), which contains 50 g/l dextran, 8 g/l sodium chloride, 400 mg/l potassium chloride, 98 mg/l magnesium sulfate, 46 mg/l disodium phosphate, 63 mg/l potassium phosphate and 910 mg/l glucose.

Before completion of transplantation into the recipient, the preservation solutions are rinsed away from the donor organ with a physiological infusion solution, for example, Ringer's Solution. In still another embodiment, a PS-binding agent can be added to the infusion solution.

The novel preservation and rinsing solutions may have a composition essentially corresponding to any of the three commercial solutions described above. However, the actual concentrations of the conventional components may vary somewhat, typically within a range of about ±50%, or about ±30%, of the mean values given above.

In one embodiment, a PS-binding agent is added to a ready-made preservation or rinse solution just before use to ensure maximum activity. Alternatively, a suitable preservation solution containing a PS-binding agent can be prepared beforehand.

EXAMPLES

Example 1

Modified Annexin Preparation

A. PEGylated Annexins

Annexins can be purified from human tissues or produced by recombinant technology. For instance, annexin V can be purified from human placentas as described by Funakoshi et al. (1987). Examples of recombinant products include expression of annexin II and annexin V in *Escherichia coli* (Kang, H.-M., Trends Cardiovasc. Med. 9:92-102 (1999); Thiagarajan and Benedict, 1997, 2000). A rapid and efficient purification method for recombinant annexin V, based on $Ca^{2+}$-enhanced binding to phosphatidylserine-containing liposomes and subsequent elution by EDTA, has been described by Berger, FEBS Lett. 329:25-28 (1993). This procedure can be improved by the use of phosphatidylserine coupled to a solid phase support.

Annexins can be coupled to polyethylene glycol (PEG) by any of several well-established procedures (reviewed by Hermanson, 1996) in a process referred to as pegylation. Contemplated pegylated annexins include chemically-derivatized annexin molecules having mono- or poly- (e.g., 2-4) PEG moieties. Methods for preparing a pegylated annexin generally include the steps of (a) reacting the annexin with polyethylene glycol (such as a reactive ester or aldehyde derivative of PEG) under conditions whereby the annexin becomes attached to one or more PEG groups and (b) obtaining the reaction product or products. In general, the optimal reaction conditions for the reactions must be determined case by case based on known parameters and the desired result. Furthermore, the reaction may produce different products having a different number of PEG chains, and further purification may be needed to obtain the desired product.

Conjugation of PEG to annexin V can be performed using the EDC plus sulfo-NHS procedure. EDC (1-ethyl-3-(3-dimethylaminopropyl)-carbodiimide hydrochloride) is used to form active ester groups with carboxylate groups using sulfo-NHS (N-hydroxysulfosuccinamide). This increases the stability of the active intermediate, which reacts with an amine to give a stable amide linkage. The conjugation can be carried out as described in Hermanson, 1996.

Bioconjugate methods can be used to produce homopolymers or heteropolymers of annexin; methods are reviewed by Hermanson, 1996. Recombinant methods can also be used to produce fusion proteins, e.g., annexin expressed with the Fc portion of immunoglobulin or another protein. The heterotetramer of annexin II with P11 has also been produced in *E. coli* (Kang et al., 1999). All of these procedures increase the molecular weight of annexin and have the potential to increase the half-life of annexin in the circulation and prolong its anticoagulant effect.

B. Homodimer of Annexin V

A homodimer of annexin V can be produced using a DNA construct shown schematically in FIG. 1C (5'-3' sense strand) (SEQ ID NO:4) and coding for an amino acid sequence represented by SEQ ID NO:6. In this example, the annexin V gene is cloned into the expression vector PCMV FLAG® 2 (available from Sigma-Aldrich) at EcoRI and BglII sites. The exact sequences prior to and after the annexin V sequence are unknown and denoted as "x". It is therefore necessary to sequence the construct prior to modification to assure proper codon alignment. The PCMV FLAG® 2 vector comes with a strong promotor and initiation sequence (Kozak) and start site (ATG) built in. The start codon before each annexin V gene must therefore be removed, and a strong stop for tight expression should be added at the terminus of the second annexin V gene. The vector also comes with an 8-amino acid peptide sequence that can be used for protein purification (asp-tyr-lys-asp-asp-asp-asp-lys) (SEQ ID NO:9). A 14-amino acid spacer with glycine-serine swivel ends allows optimal rotation between tandem gene-encoded proteins. Addition of restriction sites PvuII and ScaI allow removal of the linker if necessary. Addition of a protease site allows cleavage of tandem proteins following expression. PRESCISSION™ protease is available from Amersham Pharmacia Biotech and can be used to cleave tandem proteins. Two annexin V homodimers were generated. In the first, a "His tag" was placed at the amino terminal end of the dimer to facilitate purification (FIG. 1A). The linker sequence of 12 amino acids was flanked by a glycine and a senile residue at either end to serve as swivels. The structural scheme is shown in FIG. 1A. The amino acid sequence of the His-tagged annexin V homodimer is provided below:

(SEQ ID NO: 26)
MHHHHHHQAQVLRGTVTDFPGFDERADAETLRKAMKGLGTDEESILTLLT

SRSNAQRQEISAAFKTLFGRDLLDDLKSELTGKFEKLIVALMKPSRLYDA

YELKHALKGAGTNEKVLTEIIASRTPEELRAIKQVYEEEYGSSLEDDVVG

DTSGYYQRMLVVLLQANRDPDAGIDEAQVEQDAQALFQAGELKWGTDEEK

FITIFGTRSVSHLRKVFDKYMTISGFQIEETIDRETSGNLEQLLLAVVKS

-continued

IRSIPAYLAETLYYAMKGAGTDDHTLIRVMVSRSEIDLFNIRKEFRKNFA

TSLYSMIKGDTSGDYKKALLLLCGEDDGSLEVLFQGPSGKLAQVLRGTVT

DFPGFDERADAETLRKAMKGLGTDEESILTLLTSRSNAQRQEISAAFKTL

FGRDLLDDLKSELTGKFEKLIVALMKPSRLYDAYELKHALKGAGTNEKVL

TEIIASRTPEELRAIKQVYEEEYGSSLEDDVVGDTSGYYQRMLVVLLQAN

RDPDAGIDEAQVEQDAQALFQAGELKWGTDEEKFITIFGTRSVSHLRKVF

DKYMTISGFQIEETIDRETSGNLEQLLLAVVKSIRSIPAYLAETLYYAMK

GAGTDDHTLIRVMVSRSEIDLFNIRKEFRKNFATSLYSMIKGDTSGDYKK

ALLLLCGEDD

The "swivel" amino acids of the linker are bolded and underlined. This His-tagged annexin V homodimer was expressed at a high level in *Escherichia coli* and purified using a nickel column. The DNA in the construct was shown to have the correct sequence and the dimer had the predicted molecular weight (74 kDa). MALDI-TOF mass spectrometry was accomplished using a PERSEPTIVE BIOSYSTEMS™ VOYAGER-DE® PRO workstation operating in linear, positive ion mode with a static accelerating voltage of 25 kV and a delay time of 40 nsec.

A second human annexin V homodimer was synthesized without the His tag. The structural scheme is shown in FIG. 1B. The amino acid sequence of the (non-His-tagged) annexin V homodimer is provided below:

```
                                      (SEQ ID NO: 27)
MAQVLRGTVTDFPGFDERADAETLRKAMKGLGTDEESILTLLTSRSNAQR

QEISAAFKTLFGRDLLDDLKSELTGKFEKLIVALMKPSRLYDAYELKHAL

KGAGTNEKVLTEIIASRTPEELRAIKQVYEEEYGSSLEDDVVGDTSGYYQ

RMLVVLLQANRDPDAGIDEAQVEQDAQALFQAGELKWGTDEEKFITIFGT

RSVSHLRKVFDKYMTISGFQIEETIDRETSGNLEQLLLAVVKSIRSIPAY

LAETLYYAMKGAGTDDHTLIRVMVSRSEIDLFNIRKEFRKNFATSLYSMI

KGDTSGDYKKALLLLCGEDDGSLEVLFQGPSGKLAQVLRGTVTDFPGFDE
```
(where GS and SG are bolded and underlined)

```
RADAETLRKAMKGLGTDEESILTLLTSRSNAQRQEISAAFKTLFGRDLLD

DLKSELTGKFEKLIVALMKPSRLYDAYELKHALKGAGTNEKVLTEIIASR

TPEELRAIKQVYEEEYGSSLEDDVVGDTSGYYQRMLVVLLQANRDPDAGI

DEAQVEQDAQALFQAGELKWGTDEEKFITIFGTRSVSHLRKVFDKYMTIS

GFQIEETIDRETSGNLEQLLLAVVKSIRSIPAYLAETLYYAMKGAGTDDH

TLIRVMVSRSEIDLFNIRKEFRKNFATSLYSMIKGDTSGDYKKALLLLCG

EDD
```

Again, the "swivel" amino acids of the linker are bolded and underlined. This dimer was expressed at a high level in *E. coli* and purified by ion-exchange chromatography followed by heparin affinity chromatography. The ion-exchange column was from Bio-Rad (ECONO-PAK® HighQ Support) and the heparin affinity column was from Amersham Biosciences (HITRAP™ Heparin HP). Both were used according to manufacturers' instructions. Again, the DNA sequence of the annexin V homodimer was found to be correct. Mass spectrometry showed a protein of 73 kDa, as expected. The amino acid sequence of annexin and other proteins is routinely determined in this laboratory by mass spectrometry of peptide fragments. Expected sequences were obtained.

Human Annexin V has the following amino acid sequence:

```
                                       (SEQ ID NO: 3)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD
```

The nucleotide sequence of human annexin V, inserted as indicated in the DNA construct illustrated in FIG. 1C, is as follows:

```
                                           (SEQ ID NO: 1)
GCACAGGTTCTCAGAGGCACTGTGACTGACTTCCCTGGATTTGATGAGCG

GGCTGATGCAGAAACTCTTCGGAAGGCTATGAAAGGCTTGGGCACAGATG

AGGAGAGCATCCTGACTCTGTTGACATCCCGAAGTAATGCTCAGCGCCAG

GAAATCTCTGCAGCTTTTAAGACTCTGTTTGGCAGGGATCTTCTGGATGA

CCTGAAATCAGAACTAACTGGAAAATTTGAAAAATTAATTGTGGCTCTGA

TGAAACCCTCTCGGCTTTATGATGCTTATGAACTGAAACATGCCTTGAAG

GGAGCTGGAACAAATGAAAAAGTACTGACAGAAATTATTGCTTCAAGGAC

ACCTGAAGAACTGAGAGCCATCAAACAAGTTTATGAAGAAGAATATGGCT

CAAGCCTGGAAGATGACGTGGTGGGGGACACTTCAGGGTACTACCAGCGG

ATGTTGGTGGTTCTCCTTCAGGCTAACAGAGACCCTGATGCTGGAATTGA

TGAAGCTCAAGTTGAACAAGATGCTCAGGCTTTATTTCAGGCTGGAGAAC

TTAAATGGGGACAGATGAAGAAAAGTTTATCACCATCTTTGGAACACGA

AGTGTGTCTCATTTGAGAAAGGTGTTTGACAAGTACATGACTATATCAGG

ATTTCAAATTGAGGAAACCATTGACCGCGAGACTTCTGGCAATTTAGAGC

AACTACTCCTTGCTGTTGTGAAATCTATTCGAAGTATACCTGCCTACCTT

GCAGAGACCCTCTATTATGCTATGAAGGGAGCTGGGACAGATGATCATAC

CCTCATCAGAGTCATGGTTTCCAGGAGTGAGATTGATCTGTTTAACATCA

GGAAGGAGTTTAGGAAGAATTTTGCCACCTCTCTTTATTCCATGATTAAG

GGAGATACATCTGGGGACTATAAGAAAGCTCTTCTGCTGCTCTGTGGAGA

AGATGAC
```

C. Annexin IV Homodimer

A homodimer of annexin IV was prepared similarly to the annexin V homodimer described in Example 1B. The vector used was pET-29a(+), available from Novagen (Madison, Wis.). The plasmid sequence was denoted as pET-ANXA4-2X and was 7221 bp (SEQ ID NO:16). pET-ANXA4-2X contains an open reading frame from nucleotide number 5076 to 7049 (including 3 stop codons). The first copy of Annexin IV spans nucleotides 5076-6038 of SEQ ID NO: 16, a first swivel linker spans nucleotides 6039-6044 of SEQ ID NO: 16, the PRESCISSION™ protease recognition site spans nucleotides 6045-6068 of SEQ ID NO: 16, the second swivel linker spans nucleotides 6069-6074 of SEQ ID NO: 16, the second copy of annexin IV spans nucleotides 6081-7043 of SEQ ID NO: 16, and a kanamycin resistance gene spans nucleotides 1375-1560 of SEQ ID NO: 16. The sequence from nucleotide number 5076 to 7049 is further represented herein as SEQ ID NO: 17. Translation of SEQ ID NO:17 results in the annexin IV homodimer polypeptide having the following amino acid sequence:

```
                                           (SEQ ID NO: 19)
MAMATKGGTVKAASGFNAMEDAQTLRKAMKGLGTDEDAIISVLAYRNTAQ

RQEIRTAYKSTIGRDLIDDLKSELSGNFEQVIVGMMTPTVLYDVQELRRA

MKGAGTDEGCLIEILASRTPEEIRRISQTYQQQYGRRLEDDIRSDTSFMF

QRVLVSLSAGGRDEGNYLDDALVRQDAQDLYEAGEKKWGTDEVKFLTVLC

SRNRNHLLHVFDEYKRISQKDIEQSIKSETSGSFEDALLAIVKCMRNKSA

YFAEKLYKSMKGLGTDDNTLIRVMVSRAEIDMLDIRAHFKRLYGKSLYSF

IKGDTSGDYRKVLLVLCGGDDGSlevlfqgpSGKLAMATKGGTVKAASGF

NAMEDAQTLRKAMKGLGTDEDAIISVLAYRNTAQRQEIRTAYKSTIGRDL

IDDLKSELSGNFEQVIVGMMTPTVLYDVQELRRAMKGAGTDEGCLIEILA

SRTPEEIRRISQTYQQQYGRRLEDDIRSDTSFMFQRVLVSLSAGGRDEGN

YLDDALVRQDAQDLYEAGEKKWGTDEVKFLTVLCSRNRNHLLHVFDEYKR

ISQKDIEQSIKSETSGSFEDALLAIVKCMRNKSAYFAEKLYKSMKGLGTD

DNTLIRVMVSRAEIDMLDIRAHFKRLYGKSLYSFIKGDTSGDYRKVLLVL

CGGDD
```

In the sequence above, the swivel sites are denoted by bold and underline, the PRESCISSION™ protease site is in lower case, and an introduced restriction site is in italics. The annexin IV gene as cloned contained a single base substitution compared to the published sequence (GENBANK® accession number NM_001153) which changes the amino acid at position 137 from serine to arginine. This change is noted in bold and double underline in the amino acid sequence of the dimer above.

D. Annexin VIII Homodimer

A homodimer of annexin VIII was prepared similarly to the annexin V homodimer described in Example 1B. The vector used was pET-29a(+), available from Novagen (Madison, Wis.). The plasmid sequence was denoted as pET-ANXA8-2X and was 7257 bp (SEQ ID NO:20). pET-ANXA4-2X contains an open reading frame from nucleotide number 5076 to 7085 (including 3 stop codons). The first copy of Annexin VIII spans nucleotides 5076-6056 of SEQ ID NO:20, a first swivel linker spans nucleotides 6057-6062 of SEQ ID NO:20, the PRESCISSION™ recognition site spans nucleotides 6063-6086 of SEQ ID NO:20, the second swivel linker spans nucleotides 6087-6092 of SEQ ID NO:20, the second copy of annexin VIII spans nucleotides 6099-7079 of SEQ ID NO:20, and a kanamycin resistance gene spans nucleotides 1375-560 of SEQ ID NO:20. The sequence from nucleotide number 5076 to 7085 is further represented herein as SEQ ID NO:21. Translation of SEQ ID NO:21 results in the annexin VIII homodimer polypeptide having the following amino acid sequence:

```
                                           (SEQ ID NO: 23)
MAWWKAWIEQEGVTVKSSSHFNPDPDAETLYKAMKGIGTNEQAIIDVLTK

RSNTQRQQIAKSFKAQFGKDLTETLKSELSGKFERLIVALMYPPYRYEAK

ELHDAMKGLGTKEGVIIEILASRTKNQLREIMKAYEEDYGSSLEEDIQAD

TSGYLERILVCLLQGSRDDVSSFVDPALALQDAQDLYAAGEKIRGTDEMK

FITILCTRSATHLLRVFEEYEKIANKSIEDSIKSETHGSLEEAMLTVVKC

TQNLHSYFAERLYYAMKGAGTRDGTLIRNIVSRSEIDLNLIKCHFKKMYG

KTLSSMIMEDTSGDYKNALLSLVGSDPGSlevlfqgpSGKLAWWKAWIEQ

EGVTVKSSSHFNPDPDAETLYKAMKGIGTNEQAIIDVLTKRSNTQRQQIA

KSFKAQFGKDLTETLKSELSGKFERLIVALMYPPYRYEAKELHDAMKGLG

TKEGVIIEILASRTKNQLREIMKAYEEDYGSSLEEDIQADTSGYLERILV

CLLQGSRDDVSSFVDPALALQDAQDLYAAGEKIRGTDEMKFITILCTRSA

THLLRVFEEYEKIANKSIEDSIKSETHGSLEEAMLTVVKCTQNLHSYFAE

RLYYAMKGAGTRDGTLIRNIVSRSEIDLNLIKCHFKKMYGKTLSSMIMED

TSGDYKNALLSLVGSDP
```

In the sequence above, the swivel sites are denoted by bold and underline, the PRESCISSION™ protease site is in lower case, and an introduced restriction site is in italics. The annexin VIII gene as cloned contains a single base substitution compared to the published sequence (GENBANK® accession number NM$_{001630}$). The result is a codon change for tyrosine at position 92 from TAT to TAC.

Example 2

Affinity of Annexin V and Annexin V Homodimer for PS

Recombinant homodimers of annexin V (Diannexin, DAV) binds PS on cell surfaces with a higher affinity than monomeric annexin V (AV). The affinities of recombinant annexin V (AV) and recombinant annexin V homodimer (DAV, Diannexin) for PS on the surface of cells were compared. To produce cells with PS exposed on their surfaces, human peripheral red blood cells (RBCs) were treated with a $Ca^{2+}$ ionophore (A23187). The phospholipid translocase (flipase), which moves PS to the inner leaflet of the plasma membrane bilayer, was inactivated by treatment with N-ethyl maleimide (NEM), which binds covalently to free sulfhydryl groups. Raising intracellular $Ca^{2+}$ activates the scramblase enzyme, thus increasing the amount of PS in the outer leaflet of the plasma membrane bilayer.

Washed human RBCs were resuspended at 30% hematocrit in K-buffer (80 mM KCl, 7 mM NaCl, 10 mM HEPES, pH 7.4). They were incubated for 30 minutes at 37° C. in the presence of 10 mM NEM to inhibit the flipase. The NEM-treated cells were washed and suspended at 16% hematocrit in the same buffer with added 2 mM $CaCl_2$. The scramblase enzyme was activated by incubation for 30 minutes at 37° C. with A23187 (final concentration 4 µM). As a result of this procedure, more than 95% of the RBCs had PS demonstrable on their surface by flow cytometry.

Recombinant AV and DAV were biotinylated using the FluReporter protein-labeling kit (Molecular Probes, Eugene Oreg.). Biotin-AV and biotin-DAV conjugates were visualized with R-phycoerythrin-conjugated streptavidin (PE-SA) at a final concentration of 2 µg/ml. Flow cytometry was performed on a Becton Dickinson FACScaliber and data were analyzed with Cell Quest software (Becton Dickinson, San Jose Calif.).

No binding of AV or DAV was detectable when normal RBCs were used. However, both AV and DAV were bound to at least 95% of RBCs exposing PS. RBCs exposing PS were incubated with various amounts of AV and DAV, either (a) separately or (b) mixed in a 1:1 molar ratio, before addition of PE-SA and flow cytometry. In such mixtures, either AV or DAV was biotinylated and the amount of each protein bound was assayed as described above. The experiments were controlled for higher biotin labeling in DAV than AV.

Representative results are shown in FIG. 2. In this set of experiments, RBCs exposing PS were incubated with (a) 0.2 μg of biotinylated DAV (FIG. 2A); (b) 0.2 μg of nonbiotinylated DAV (FIG. 2B); (c) 0.2 μg of biotinylated AV and 0.2 μg nonbiotinylated DAV; and (d) 0.2 μg of biotinylated DAV and 0.2 μg nonbiotinylated AV (FIG. 2D). Comparing FIG. 2B and FIG. 2D shows that the presence of 0.2 μg of nonbiotinylated AV had no effect on the binding of biotinylated DAV. However, comparing FIG. 2A and FIG. 2C shows that the presence of 0.2 μg of nonbiotinylated DAV strongly reduced the amount of biotinylated AV bound to PS-exposing cells. These results indicate that DAV and AV compete for the same PS-binding sites on RBCs, but with different affinities; DAV binds to PS that is exposed on the surface of cells with a higher affinity than does AV. We have used this model to show that the Annexin VIII homodimer has a somewhat higher affinity for PS on cell surfaces than the Annexin V homodimer does, whereas the affinity of the Annexin IV homodimer is somewhat lower.

Example 3

Diannexin Clearance

Recombinant homodimer of human annexin V (Diannexin, DAV, 73 kDa) has a longer half-life in the circulation than monomeric annexin V (AV, 36 kDa). The molecular weight of Diannexin exceeds renal filtration threshold whereas that of annexin V does not. This was demonstrated by following the clearance of radioiodinated Diannexin from the peripheral blood of a rat. Observations in the rabbit (Thiagarajan and Benedict, Circulation 96: 2339, 1977), rat, cynomolgus monkey, (Romisch et al., Thrombosis Res. 61: 93, 1991) and humans (Kemerink et al., J. Nucl. Med. 44: 947, 2003) had shown that AV has a short half-life in the circulation (7 to 24 minutes, respectively), with a major loss into the kidneys.

Figure 3:
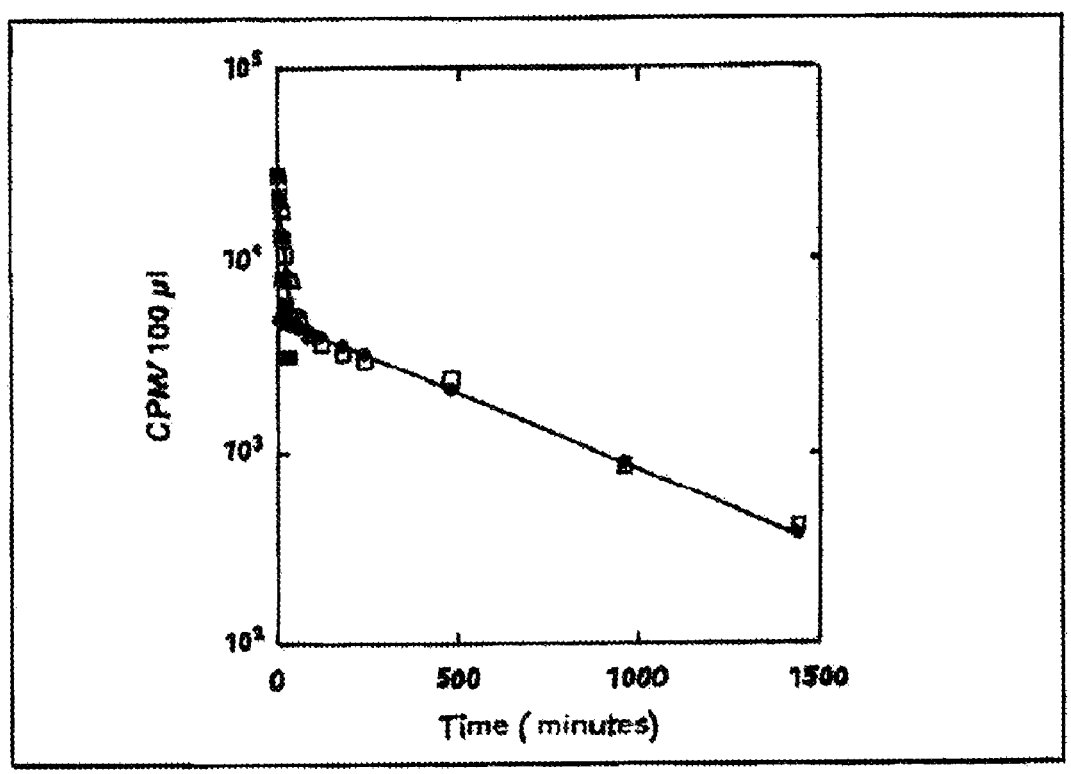
FIG. 3-B*lood* radioactivity in rats following injection of radio-labelled DAV. The decrease in blood radioactivity (open squares) is biphasic with an alpha-phase (closed squares) and beta-phase (closed circles) superimposed.

As shown herein, rats were injected with radiolabeled Diannexin, blood samples were obtained at 5, 10, 15, 20, 30, 45, and 60 min and 2, 3, 4, 8, 16 and 24 hrs, and blood radioactivity was determined to construct a blood disappearance curve. (FIG. 3) Disappearance of Diannexin from blood could be described by a two-compartment model, with about 75-80% disappearing in the α-phase (t/2 about 10 min), and 15-20% in the β-phase (t/2 about 400 min). Clearance could be described by a two-compartment model, with half-lives of 9-14 min and 6-7 hrs, respectively. Two experiments were performed, each with three male Wistar rats (300 gram). Diannexin was labeled with $^{125}I$ by the method of Macfarlane, and the labeled protein was separated from free Sephadex G-50. After injection of NaI (5 mg/kg) to prevent thyroid uptake of label, about $8\times10^6$ cpm (50 μL of protein solution diluted to 0.5 mL with saline) were injected via a femoral vein catheter (rats 1 and 2) or via the vein of the penis (rat 3). At specified times thereafter, blood samples (150 μL) were obtained from a tail vein and 100 μL counted.

The β-phase parameters were calculated from the data collected between 45 min and 24 hrs. The α-phase parameters were calculated from the data between 5 and 45 min by the subtraction method. The blood radioactivity curves were analyzed by a two-compartment model, using the subtraction method. The linear correlation coefficients for the α- and the β-phase were −0.99 and −0.99 in experiment 1, and −0.95 and −0.96 in experiment 2. The clearance parameters are shown in Table 1.

TABLE 1

Diannexin clearance parameters.

| | Experiment 1 | Experiment 2 |
|---|---|---|
| t/2 alpha phase | 9.2 min | 14.1 min |
| t/2 beta phase | 385 min | 433 min |
| % in alpha phase | 85% | 79% |
| % in beta phase | 15% | 21% |
| Isotope recovery in blood (%) | 89% | 52% |

These observations show that dimerization of annexin V has extended its survival in the circulation.

The pharmacokinetics of Diannexin were also studied following intravenous administration of several doses to adult male and female Sprague-Dawley rats. Mean Diannexin concentration-time data, determined by an ELISA assay, for males and females separately (9 rats per gender) were subjected to noncompartmental pharmacokinetic analysis using WinNonlin 1:5, with nominal times. The results are summarized in Table 2 below.

TABLE 2

Summary of Diannexin Plasma Pharmacokinetic Parameters.

| Group | Dosage mg/kg | Gender | t½ h |
|---|---|---|---|
| 4 | 0.5 | M | 2.4 |
| | | F | 2.2 |
| 2 | 1 | M | 2.0 |
| | | F | 1.8 |
| 3 | 5 | M | 3.1 |
| | | F | 1.8 |

Thus by two independent methods Diannexin has been shown to have a much longer half life in the circulation than reported for annexin V monomer. The prolonged survival of Diannexin in the circulation will augment its therapeutic efficacy.

Example 4

Diannexin is a Potent Inhibitor of Secretory Phospholipase $A_2$

The inhibitory effects of annexin V (AV) and the annexin V homodimer (DAV) on the activity of human $sPLA_2$ (Cayman, Ann Arbor Mich.) were compared. PS externalized on RBCs treated with NEM and A23187, as described above, was used as the substrate. In control cells, AV and DAV were found to bind to PS-exposing RBCs as demonstrable by flow cytometry. Incubation of the PS-exposing cells with $sPLA_2$ removes PS, so that the cells no longer bind annexin. If the PS-exposing cells are treated with AV or DAV before incubation with $PLA_2$, the PS is not removed. The cells can be exposed to a $Ca^{2+}$-chelating agent, which dissociates AV or DAV from PS, and subsequent binding of labeled AV reveals the residual PS on cell surfaces. Titration of AV and DAV in such assays shows that both are potent inhibitors of the activity of sPLA$_2$ on cell-surface PS.

The inhibition of phospholipase is also demonstrable by another method. Activity of sPLA$_2$ releases lysophosphatidylcholine, which is hemolytic. It is therefore possible to compare the inhibitory effects of AV and DAV on PLA$_2$ in a hemolytic assay. As shown in FIG. 4, both AV and DAV inhibit the action of PLA$_2$, with DAV being somewhat more efficacious. Hemolysis induced after 60 minutes incubation with pPLA$_2$ was strongly reduced in the presence of DAV or AV compared to hemolysis in their absence. From these results it can be concluded that a homodimer of annexin V is a potent inhibitor of secretory PLA$_2$. It should therefore decrease the formation of mediators such as thromboxane A$_2$, as well as lysophosphatidylcholine and lysophosphatidic acid, which are believed to contribute to the pathogenesis of IRI (Hashizume et al. Jpn. Heart J., 38: 11, 1997; Okuza et al., J. Physiol., 285: F565, 2003).

Example 5

Modified Annexin Protects Against IRI

Figure 5:
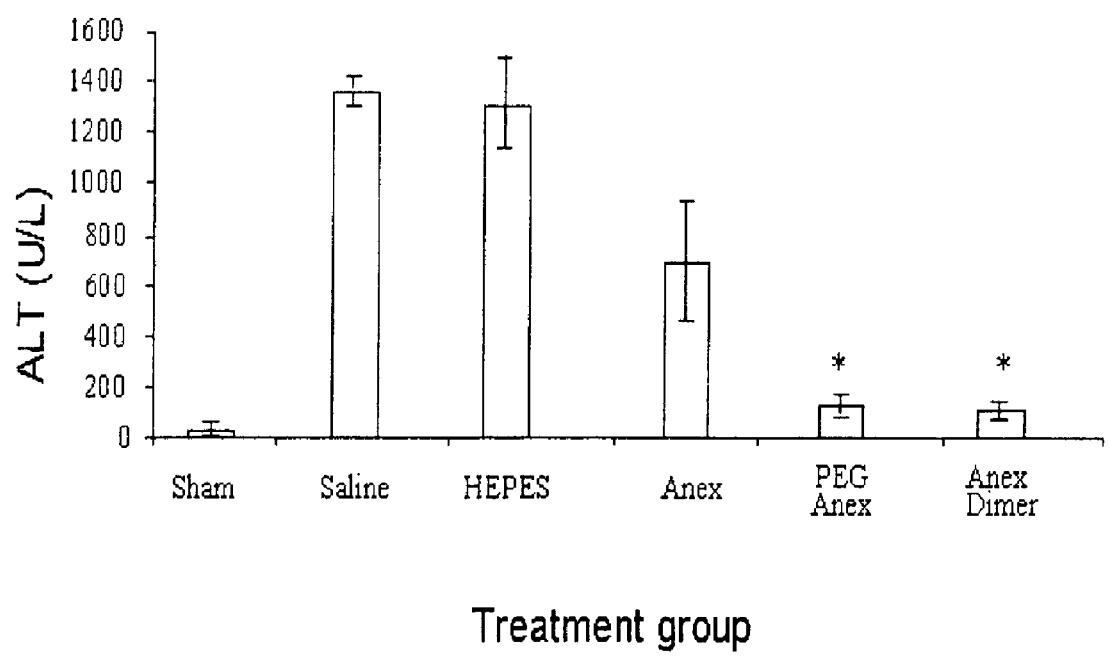
FIG. 5 shows serum alanine aminotransferase (ALT) levels in mice sham operated (Sham), mice given saline, mice given HEPES buffer 6 hours before clamping the hepatic artery, mice given pegylated annexin (PEG Anex) or annexin dimer 6 hours before clamping the artery, and mice given monomeric annexin (Anex). The asterisk above PEG ANNEX and ANNEX DIMER indicates p<0.001.

A mouse liver model of warm IRI was used to ascertain whether modified annexins protect against this type of injury, compare the activity of annexin V with modified annexins, and determine the duration of activity of modified annexins. The model has been described by Teoh et al. (Hepatology 36:94, 2002). Female C57BL6 mice weighing 18 to 25 g were used. Under ketamine/xylazine anesthesia, the blood supply to the left lateral and median lobes of the liver was occluded with an atraumatic microvascular clamp for 90 minutes. Reperfusion was then established by removal of the vascular clamp. The animals were allowed to recover, and 24 hours later they were killed by exsanguination. Liver damage was assessed by measurement of serum alanine aminotransferase (ALT) activity and histological examination. A control group was subjected to anesthesia and sham laparotomy. To assay the activity of annexin V and modified annexins, groups of 4 mice were used. Each of the mice in the first group was injected intravenously with 25 micrograms of annexin V (AV), each of the second group received 25 micrograms of annexin homodimer (DAV), and each of the third group received 2.5 micrograms of annexin V coupled to polyethylene glycol (PEG-AV, 57 kDa). Controls received saline or the HEPES buffer in which the annexins were stored. In the first set of experiments, the annexins were administered minutes before clamping branches of the hepatic artery. In the second set of experiments, annexins and HEPES were administered 6 hours before initiating ischemia. Representative experimental results are summarized in FIG. 5.

In animals receiving annexin V (AV) just before ischemia, slight protection was observed. By contrast, animals receiving the annexin dimer (DAV) or PEG-AV, either just before or 6 hours before ischemia, showed dramatic protection against IRI. Histological studies confirmed that there was little or no hepatocellular necrosis in these groups. The results show that the modified annexins (DAV and PEG-AV) are significantly more protective against ischemia reperfusion injury in the liver than is AV. Furthermore, the modified annexins (DAV and PEG-AV) retain their capacity to attenuate IRI for at least 6 hours.

In sham-operated animals, levels of ALT in the circulation were very low. In animals receiving saline just before ischemia, or HEPES 6 hours before ischemia, levels of ALT were very high, and histology confirmed that there was severe hepatocellular necrosis.

Example 6

IRI and Diannexin

Studies were undertaken to test embodiments of the invention for the pathogenesis of IRI and mode of action of Diannexin. During ischemia, PS becomes accessible on the luminal surface of endothelial cells (EC) in hepatic sinusoids. During reperfusion leukocytes and platelets become attached to PS on the surface of EC and reduce blood flow in the hepatic microcirculation. Diannexin binds to PS on the surface of EC and decreases the attachment of leukocytes and platelets to them. By this mechanism Diannexin maintains blood flow in the hepatic microcirculation and thereby attenuates IRI.

This Example provides observation of the microcirculation in the mouse liver in vivo using a published method (McCuskey et al., Hepatology 40: 386, 2004). As described in example 5, 90 minutes of ischemia was followed by various times of reperfusion. FIGS. 6A and 6B show that during reperfusion many leukocytes become attached to EC in both the periportal and centrilobular areas (IR). Diannexin (1 mg/kg, intravenous) reduces such attachment in a statistically significant manner (IR+D). FIGS. 7A and 7B show that this is also true of the adherence of platelets to EC during reperfusion. This Example shows that the mode of action of Diannexin in attenuating IRI is therefore confirmed. Diannexin does not influence the phagocytic activity of Kupffer cells in either location. Hence, Diannexin has no effect on this defense mechanism against pathogenic organisms. This finding supports other evidence that Diannexin does not have adverse effects.

Example 7

Diannexin and Liver IRI

This Example was undertaken to ascertain whether Diannexin can protect the liver from IRI when administration of the protein is delayed until after the commencement of reperfusion. Our standard protocol for the mouse liver warm IRI was used: adult female C57BL6 mice, 90 minutes ischemia and 24 hrs reperfusion. Endpoints were serum ALT levels and liver pathology at 24 hours. Diannexin (1 mg/kg) was administered 10 minutes and 60 minutes after commencement of reperfusion (Example 5). As shown in Table 3, both of these procedures significantly decreased ALT levels, and protective effects were confirmed by liver histology. These observations show that Diannexin administration can be delayed until at least 1 hour after the initiation of reperfusion, implying that EC changes during the first hour are reversible. The findings also show that administration of Diannexin up to one hour after re-establishing the circulation in recipients of transplanted organs should attenuate IRI.

TABLE 3

Effect of Diannexin (1 mg/kg) Administration during Reperfusion.
Administration during Reperfusion

| Time after commencement of reperfusion | Serum ALT mean ± s.d. | Probability |
|---|---|---|
| 0 (untreated control) | 840 ± 306 | |
| 10 minutes | 153 ± 83 | p < 0.05 |
| 60 minutes | 255 ± 27 | p < 0.05 |

Example 8

Timing of Diannexin Administration

The efficacy of Diannexin in protection of organs during cold ischemia-warm reperfusion injury was evaluated in well-defined rat liver transplantation model (Sawitzki, B. et al. Human Gene Therapy 13: 1495, 2002). Livers were recovered from adult male Sprague-Dawley rats, perfused with University of Wisconsin solution, kept at 4° C. for 24 hrs and transplanted orthotopically into syngeneic recipients. Under these conditions 60% of untreated recipients died within 48 hours of transplantation, as previously observed in similar experiments. Another 10 recipients of liver grafts were given Diannexin (0.2 mg/kg intravenously) 10 minutes and 24 hrs after transplantation. All these animals survived for more than 14 days, which on the basis of previous experience implies survival unlimited by the operation.

As shown in Table 4, levels of the liver enzyme alanine aminotransferase (ALT) in the circulation of untreated recipients at 6 hrs and 24 hrs post transplantation were significantly higher than in Diannexin-treated recipients. Diannexin-mediated cytoprotection was confirmed by histological examination of the livers in transplant recipients. By 7 days post transplantation ALT levels were back to the normal range in all recipients.

In a second group of 10 recipients Diannexin was used in a different way. Rat livers were obtained from Sprague-Dawley donors and perfused ex vivo with University of Wisconsin Solution containing Diannexin (0.2 mg/liter) twice, before 24 hr of 4° C. cold storage and just before orthotopic transplantation. No Diannexin was given post-transplant to these recipients, all of which survived >14 days. Again ALT levels at 6 and 24 hrs were significantly lower than in untreated animals and histological examination showed a substantial difference between the well preserved livers in Diannexin-treated and the partially necrotic livers in control graft recipients.

These observations show that Diannexin markedly attenuates IRI in a cold ischemia-warm reperfusion rat liver model which is similar to the situation in human liver transplantation. Diannexin is equally efficacious when included in the solution used to perfuse the liver ex vivo when administered to recipients of liver grafts shortly after transplantation.

TABLE 4

Serum ALT levels (IU/L) in rat liver graft recipients.

| | Untreated controls | Diannexin treated | Probability |
|---|---|---|---|
| 6 hrs | 1345 ± 530 | 267 ± 110 | <0.001 |
| 1 day | 4031 ± 383 | 620 ± 428 | <0.001 |
| 7 days | 99 ± 31 | 72 ± 8 | >0.5 |

Example 9

Diannexin Attenuates IRI in Steatotic Liver

When human livers contain more than 20% of fat they are termed steatotic. The risk of IRI following transplantation of such livers is increased, and it would be desirable to attenuate this complication. A recognized model of steatosis, of the type associated with the metabolic syndrome preceding type 2 diabetes, is provided by Zucker (leptin-deficient) rats (Amersi et al. Proc. Natl. Acad. Sci. U.S.A. 2002; 99: 8915). To determine whether Diannexin can protect steatotic rat livers following transplantation this model was used.

The experimental procedure was as described by Amersi et al. (loc cit). Fatty livers were recovered from Zucker rats and stored at 4° in University of Wisconsin solution for 4 hours. This results in IRI of severity is comparable to that observed following storage of lean livers for 24 h. Following storage the steatotic livers were transplanted orthotopically into syngeneic lean recipients. Diannexin (200 µg/kg) was administered to 10 recipients at the time of reperfusion and on the second day after transplantation. A control group of 10 fatty liver recipients and another group of sham-operated rats were included. The recipients of fatty livers not given Diannexin showed 50% mortality; those receiving Diannexin showed 100% survival (p<0.01). Fatty liver recipients treated with Diannexin showed significantly lower ALT levels than untreated, control fatty liver recipients (p<0.05). These functional data were well correlated with Suzuki's histological grading of hepatic injury. Unlike in untreated fatty liver transplant recipients, those in Diannexin-treated animals showed minimal sinusoidal congestion and necrosis, and good preservation of lobular architecture. These observations document the potential utility of Diannexin to increase the transplant donor pool through attenuation of IRI when marginal steatotic livers are transplanted.

Example 10

Diannexin Effects on Thrombosis, Hemostasis, and Stroke

The observations described in the preceding Examples show that Diannexin markedly attenuates IRI in the mouse liver, and raised the possibility that the same would be true of IRI in other organs, including the brain. The capacity of Diannexin to attenuate IRI injury, as described above, was an important part of the profile leading to exploration for treatment of stroke. The other important part of the profile is that Diannexin has potent antithrombotic activity with minimal effects on hemostasis.

Distinction Between Effects on Thrombosis and Hemostasis

It has been established that annexin V inhibits arterial and venous thrombosis with minimal effects on hemorrhage (Romisch et al. Thrombosis Res. 1991; 61: 93; Thiagarajan and Benedict Circulation 1977; 96: 2339), a remarkable and clinically desirable dissociation. These observations, together with the absence of increased bleeding when the Diannexin is used to prevent IRI in the major surgical operations of organ transplantation, described in Example 8, raise the question whether there is any distinction between the mechanisms mediating hemostasis and thrombosis. Obviously some events, such as fibrin deposition, are common to both pathways, but evidence is accumulating that there is partial separation of the pathways. Major events in hemostasis include: (1) recruitment of platelets to sites of vascular injury and their activation and aggregation; (2) activity of the tissue factor (TF)/factor VIIa complex. Annexin V does not bind to several adhesion molecules mediating the recruitment of platelets to damaged blood vessels. Platelets are initially attached to extracellular matrix (ECM) through the binding of von Willebrand factor to platelet factor Ib. Adhesion continues through the interaction of platelet integrin $\alpha_2\beta_3$ with the ECM (see Kleinschnitz et al. J. Exp. Med. 2006; 203: 513-518).

Annexin V does not inhibit platelet aggregation induced by thrombin or collagen (Sun et al. Thromb. Res. 1993; 62: 289-296), and the same is true of Diannexin (data not shown). TF/VIIa activity mediates the local deposition of fibrin at sites of injury. The importance of this pathway in hemostasis is demonstrated by two sets of observations. First, mice with targeted inactivation of either the TF or the factor VII gene exhibit severe bleeding during embryonic or early postnatal life (references in Kleinschnitz et al., loc cit.). These hemorrhagic tendencies are more pronounced than in mice deficient in other coagulant proteins. Second, recombinant factor VIIa is highly efficacious in the treatment of human patients with hemorrhage, not only in hemophilia but also in trauma and other clinical conditions (Hedner Semin. Hematol. 2004; 41: 35-39).

Annexin V does not inhibit the activity of the TF/VIIa complex when tested side-by-side in experiments where it strongly inhibits prothrombinase activity (Rao et al. Thrombosis Res. 1992; 67: 517-531). A TF-annexin V chimeric protein was generated to target TF to sites of vascular damage (Huang et al. Blood 2006; 107: 980-986). In therapeutic concentrations this construct decreased bleeding in experimental animals, demonstrating that the annexin V component was not impairing the hemostatic activity of TF in the complex. In contrast to these minimal effects on hemostasis, annexin V and Diannexin exert anti-thrombotic activity, notably inhibition of prothrombinase activity.

Diannexin Attenuates Reperfusion Injury in a Stroke Model

This experiment was undertaken to ascertain the effectiveness of Diannexin in treatment of stroke.

A well-characterized mouse model has been used. This was developed because the lesions following middle cerebral artery occlusion include edema and hemorrhage into the area of reperfusion, which complicate human stroke (Maier et al. Ann. Neurol. 2006; 59: 929-938). Knock-out (KO) mice with targeted disruption of the inducible mitochondrial manganese-containing superoxide dismutase are subjected to a mild stroke followed by early reperfusion and up to 3-day survival. These heterozygous (SOD2−/+) mice are more susceptible to IRI than their wild-type counterparts. During the period 1 to 3 days after commencing reperfusion there is edema, as shown by extravasation of the Evans blue dye. The area of brain damage increases significantly, and in many animals there is hemorrhage into the reperfused area (Maier et al. loc cit.). These animals allow evaluation of treatment strategies designed to decrease the complications of cerebral reperfusion.

To ascertain whether Diannexin can attenuate IRI in this model two groups of SOD2 (−/+) mice were subjected to transient (30 minutes) cerebral artery occlusion (MCAO). Ten minutes before commencing reperfusion in one group Diannexin (200 micrograms/kg) was injected intravenously. The other group served as an untreated control. In two different experiments Diannexin injection had no demonstrable effect on brain damage assessed by the size of the primary infarct 24 hours after commencing reperfusion. However, Diannexin treatment decreased edema measured 72 hours after commencing reperfusion and eliminated the extension of the area of brain damage between 24 and 72 hours. Particularly striking was the reduction in the rates of hemorrhage (12/15 in controls as compared with 3/13 in Diannexin-treated mice, p=0.003). Because Diannexin can inhibit thrombosis there was a theoretical possibility that it might also increase hemorrhage. However, the opposite was observed, showing that by preserving vascular integrity, and having minimal effects on mechanisms involved in hemostasis, Diannexin can attenuate IRI without increasing risk of hemorrhage. This is an important consideration for any treatment complementing mechanical thrombus removal or thrombolysis.

By exposing subendothelial connective tissues, the above-mentioned procedures allow attachment of platelets, leukocytes and microparticles. This has two important consequences: increasing the likelihood of rethrombosis and that of restenosis. Restenosis, which results from expansion of the area of smooth muscle and connective tissue in the arterial wall, is a major complication following coronary angioplasty. The release of growth factors and cytokines from platelets and leukocytes is thought to initiate restenosis. If the attachment of platelets, leukocytes, and microparticles to the subendothelium can be reduced the likelihood of rethrombosis and restenosis can be decreased. Annexin V binds to collagen X, a constituent of basement membrane (von der Mark and Mollenhauer Cell Mol. Life. Sci. 1997; 53: 539) and to heparan sulfate, a constituent of extracellular connective tissue matrix (Ishitzuka et al., J. Biol. Chem. 1998; 273: 9935). It is anticipated that Diannexin has similar effects and can decrease the attachment of platelets, leukocytes and microparticles to the subendothelium of cerebral arteries when the EC lining is damaged following surgical removal of thrombi or thrombolysis. It is further anticipated that the risks of rethrombosis and restenosis will be decreased by Diannexin therapy.

All references cited above are incorporated herein by reference in their entirety.

The words "comprise", "comprises," and "comprising" are to be interpreted inclusively rather than exclusively.

What is claimed is:

1. A method of attenuating ischemia-reperfusion injury (IRI), said method comprising administering to a patient in need thereof a phosphatidylserine (PS) binding agent wherein the PS binding agent binds with high affinity to PS on cell surfaces, and wherein the PS binding agent is an isolated annexin at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12,
wherein the linker is at least one glycine-serine sequence, and whereby said administering attenuates IRI.

2. The method of claim 1, wherein the PS-binding agent inhibits the attachment of monocytes or platelets that express receptors for PS to ischemic or activated cells, and wherein the ischemic or activated cells express PS on their cell surface.

3. The method of claim 1, wherein the PS-binding agent inhibits the attachment of enzymes that use PS as a docking site to ischemic or activated cells, wherein the ischemic or activated cells express PS on their cell surface and wherein the enzyme is secretory phospholipase A2 or a prothrombinase complex.

4. The method of claim 1, wherein the IRI is caused by organ transplantation.

5. The method of claim 1, wherein the IRI is caused by tissue grafting.

6. The method of claim 1, wherein the IRI is caused by surgery in which the blood supply to the organ is reduced or cut off.

7. The method of claim 4, wherein the PS-binding agent is administered to the patient up to about 6 hours prior to reperfusion.

8. The method of claim 4, wherein the PS-binding agent is administered to the patient up to about 1 hour after reperfusion commences.

9. The method of claim 4, wherein the IRI is caused by surgery cutting off and/or restricting blood flow and the PS-binding agent is administered to the patient within about 6 hours of the surgical procedure.

10. A method of attenuating ischemia reperfusion injury (IRI), said method comprising administering to an organ transplant recipient a composition comprising a phosphatidylserine (PS) binding agent, wherein the PS binding agent binds with high affinity to PS on cell surfaces, and wherein the PS binding agent is an isolated annexin at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12,
wherein the linker is at least one glycine-serine sequence, and whereby said administering attenuates IRI.

11. A method of attenuating ischemia reperfusion injury (IRI), said method comprising administering to a stroke patient a composition comprising a phosphatidylserine (PS) binding agent wherein the PS binding agent binds with high affinity to PS on cell surfaces, and wherein the PS binding agent is an isolated annexin at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12,
wherein the linker is at least one glycine-serine sequence, and whereby said administering attenuates IRI.

12. A method of attenuating ischemia reperfusion injury (IRI), said method comprising administering to a patient suffering from myocardial infarction a composition comprising a phosphatidylserine (PS) binding agent, wherein the PS binding agent binds with high affinity to PS on cell surfaces, and wherein the PS binding agent is an isolated annexin at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12,
wherein the linker is at least one glycine-serine sequence, and whereby said administering attenuates IRI.

13. The method of claim 1, wherein the isolated annexin is a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12.

14. The method of claim 10, wherein the isolated annexin is a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12.

* * * * *

UNITED STATES PATENT AND TRADEMARK OFFICE
CERTIFICATE OF CORRECTION

PATENT NO. : 7,635,680 B2  Page 1 of 1
APPLICATION NO. : 11/734471
DATED : December 22, 2009
INVENTOR(S) : Anthony Allison It is certified that error appears in the above-identified patent and that said Letters Patent is hereby corrected as shown below:

Column 111, line 16 should be corrected to read "wherein the linker has at least one glycine-serine sequence".

Column 112, line 1 should be corrected to read "wherein the linker has at least one glycine-serine sequence".

Column 112, line 18 should be corrected to read "wherein the linker has at least one glycine-serine sequence".

Column 112, line 36 should be corrected to read "wherein the linker has at least one glycine-serine sequence".

Signed and Sealed this

Fourth Day of May, 2010

David J. Kappos
*Director of the United States Patent and Trademark Office*

SEQUENCE LISTING

<160> NUMBER OF SEQ ID NOS: 28

<210> SEQ ID NO 1
<211> LENGTH: 957
<212> TYPE: DNA
<213> ORGANISM: Homo sapiens

<400> SEQUENCE: 1

```
gcacaggttc tcagaggcac tgtgactgac ttccctggat ttgatgagcg ggctgatgca        60
gaaactcttc ggaaggctat gaaaggcttg gcacagatg aggagagcat cctgactctg       120
ttgacatccc gaagtaatgc tcagcgccag gaaatctctg cagcttttaa gactctgttt       180
ggcagggatc ttctggatga cctgaaatca gaactaactg gaaaatttga aaaattaatt       240
gtggctctga tgaaaccctc tcggctttat gatgcttatg aactgaaaca tgccttgaag       300
ggagctggaa caaatgaaaa agtactgaca gaaattattg cttcaaggac acctgaagaa       360
ctgagagcca tcaaacaagt ttatgaagaa gaatatggct caagcctgga agatgacgtg       420
gtggggggaca cttcagggta ctaccagcgg atgttggtgg ttctccttca ggctaacaga       480
gacccctgatg ctggaattga tgaagctcaa gttgaacaag atgctcaggc tttatttcag       540
gctggagaac ttaaatgggg gacagatgaa gaaaagttta tcaccatctt tggaacacga       600
agtgtgtctc atttgagaaa ggtgtttgac aagtacatga ctatatcagg atttcaaatt       660
gaggaaacca ttgaccgcga gacttctggc aatttagagc aactactcct tgctgttgtg       720
aaatctattc gaagtatacc tgcctacctt gcagagaccc tctattatgc tatgaaggga       780
gctgggacag atgatcatac cctcatcaga gtcatggttt ccaggagtga gattgatctg       840
tttaacatca ggaaggagtt taggaagaat tttgccacct ctctttattc catgattaag       900
ggagatacat ctggggacta taagaaagct cttctgctgc tctgtggaga agatgac         957
```

<210> SEQ ID NO 2
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 2

```
gca cag gtt ctc aga ggc act gtg act gac ttc cct gga ttt gat gag         48
Ala Gln Val Leu Arg Gly Thr Val Thr Asp Phe Pro Gly Phe Asp Glu
1               5                   10                  15 cgg gct gat gca gaa act ctt cgg aag gct atg aaa ggc ttg ggc aca         96
Arg Ala Asp Ala Glu Thr Leu Arg Lys Ala Met Lys Gly Leu Gly Thr
            20                  25                  30 gat gag gag agc atc ctg act ctg ttg aca tcc cga agt aat gct cag        144
Asp Glu Glu Ser Ile Leu Thr Leu Leu Thr Ser Arg Ser Asn Ala Gln
        35                  40                  45 cgc cag gaa atc tct gca gct ttt aag act ctg ttt ggc agg gat ctt        192
Arg Gln Glu Ile Ser Ala Ala Phe Lys Thr Leu Phe Gly Arg Asp Leu
    50                  55                  60 ctg gat gac ctg aaa tca gaa cta act gga aaa ttt gaa aaa tta att        240
Leu Asp Asp Leu Lys Ser Glu Leu Thr Gly Lys Phe Glu Lys Leu Ile
65                  70                  75                  80 gtg gct ctg atg aaa ccc tct cgg ctt tat gat gct tat gaa ctg aaa        288
Val Ala Leu Met Lys Pro Ser Arg Leu Tyr Asp Ala Tyr Glu Leu Lys
                85                  90                  95 cat gcc ttg aag gga gct gga aca aat gaa aaa gta ctg aca gaa att        336
His Ala Leu Lys Gly Ala Gly Thr Asn Glu Lys Val Leu Thr Glu Ile
            100                 105                 110 att gct tca agg aca cct gaa gaa ctg aga gcc atc aaa caa gtt tat        384
Ile Ala Ser Arg Thr Pro Glu Glu Leu Arg Ala Ile Lys Gln Val Tyr
        115                 120                 125 gaa gaa gaa tat ggc tca agc ctg gaa gat gac gtg gtg ggg gac act        432
```

```
Glu Glu Glu Tyr Gly Ser Ser Leu Glu Asp Asp Val Val Gly Asp Thr
            130                 135                 140 tca ggg tac tac cag cgg atg ttg gtg gtt ctc ctt cag gct aac aga        480
Ser Gly Tyr Tyr Gln Arg Met Leu Val Val Leu Leu Gln Ala Asn Arg
145                 150                 155                 160 gac cct gat gct gga att gat gaa gct caa gtt gaa caa gat gct cag        528
Asp Pro Asp Ala Gly Ile Asp Glu Ala Gln Val Glu Gln Asp Ala Gln
                165                 170                 175 gct tta ttt cag gct gga gaa ctt aaa tgg ggg aca gat gaa gaa aag        576
Ala Leu Phe Gln Ala Gly Glu Leu Lys Trp Gly Thr Asp Glu Glu Lys
            180                 185                 190 ttt atc acc atc ttt gga aca cga agt gtg tct cat ttg aga aag gtg        624
Phe Ile Thr Ile Phe Gly Thr Arg Ser Val Ser His Leu Arg Lys Val
        195                 200                 205 ttt gac aag tac atg act ata tca gga ttt caa att gag gaa acc att        672
Phe Asp Lys Tyr Met Thr Ile Ser Gly Phe Gln Ile Glu Glu Thr Ile
    210                 215                 220 gac cgc gag act tct ggc aat tta gag caa cta ctc ctt gct gtt gtg        720
Asp Arg Glu Thr Ser Gly Asn Leu Glu Gln Leu Leu Leu Ala Val Val
225                 230                 235                 240 aaa tct att cga agt ata cct gcc tac ctt gca gag acc ctc tat tat        768
Lys Ser Ile Arg Ser Ile Pro Ala Tyr Leu Ala Glu Thr Leu Tyr Tyr
                245                 250                 255 gct atg aag gga gct ggg aca gat gat cat acc ctc atc aga gtc atg        816
Ala Met Lys Gly Ala Gly Thr Asp Asp His Thr Leu Ile Arg Val Met
            260                 265                 270 gtt tcc agg agt gag att gat ctg ttt aac atc agg aag gag ttt agg        864
Val Ser Arg Ser Glu Ile Asp Leu Phe Asn Ile Arg Lys Glu Phe Arg
        275                 280                 285 aag aat ttt gcc acc tct ctt tat tcc atg att aag gga gat aca tct        912
Lys Asn Phe Ala Thr Ser Leu Tyr Ser Met Ile Lys Gly Asp Thr Ser
    290                 295                 300 ggg gac tat aag aaa gct ctt ctg ctg ctc tgt gga gaa gat gac            957
Gly Asp Tyr Lys Lys Ala Leu Leu Leu Leu Cys Gly Glu Asp Asp
305                 310                 315
```

<210> SEQ ID NO 3
<211> LENGTH: 319
<212> TYPE: PRT
<213> ORGANISM: Homo sapiens

<400> SEQUENCE: 3

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125
```

```
Glu Glu Glu Tyr Gly Ser Ser Leu Glu Asp Asp Val Val Gly Asp Thr
    130                 135                 140
Ser Gly Tyr Tyr Gln Arg Met Leu Val Val Leu Leu Gln Ala Asn Arg
145                 150                 155                 160
Asp Pro Asp Ala Gly Ile Asp Glu Ala Gln Val Glu Gln Asp Ala Gln
                165                 170                 175
Ala Leu Phe Gln Ala Gly Glu Leu Lys Trp Gly Thr Asp Glu Glu Lys
            180                 185                 190
Phe Ile Thr Ile Phe Gly Thr Arg Ser Val Ser His Leu Arg Lys Val
        195                 200                 205
Phe Asp Lys Tyr Met Thr Ile Ser Gly Phe Gln Ile Glu Glu Thr Ile
    210                 215                 220
Asp Arg Glu Thr Ser Gly Asn Leu Glu Gln Leu Leu Leu Ala Val Val
225                 230                 235                 240
Lys Ser Ile Arg Ser Ile Pro Ala Tyr Leu Ala Glu Thr Leu Tyr Tyr
                245                 250                 255
Ala Met Lys Gly Ala Gly Thr Asp Asp His Thr Leu Ile Arg Val Met
            260                 265                 270
Val Ser Arg Ser Glu Ile Asp Leu Phe Asn Ile Arg Lys Glu Phe Arg
        275                 280                 285
Lys Asn Phe Ala Thr Ser Leu Tyr Ser Met Ile Lys Gly Asp Thr Ser
    290                 295                 300
Gly Asp Tyr Lys Lys Ala Leu Leu Leu Leu Cys Gly Glu Asp Asp
305                 310                 315

<210> SEQ ID NO 4
<211> LENGTH: 2022
<212> TYPE: DNA
<213> ORGANISM: Artificial sequence
<220> FEATURE:
<223> OTHER INFORMATION: modified annexin gene
<220> FEATURE:
<221> NAME/KEY: misc_feature
<222> LOCATION: (45)..(45)
<223> OTHER INFORMATION: n= a, c, t, or g
<220> FEATURE:
<221> NAME/KEY: misc_feature
<222> LOCATION: (1003)..(1005)
<223> OTHER INFORMATION: n= a, c, t, or g
<220> FEATURE:
<221> NAME/KEY: misc_feature
<222> LOCATION: (1054)..(1056)
<223> OTHER INFORMATION: n= a, c, t, or g

<400> SEQUENCE: 4
atggactaca aagacgatga cgacaagctt gcggccgcga attcngcaca ggttctcaga      60
ggcactgtga ctgacttccc tggatttgat gagcgggctg atgcagaaac tcttcggaag     120
gctatgaaag gcttgggcac agatgaggag agcatcctga ctctgttgac atcccgaagt     180
aatgctcagc gccaggaaat ctctgcagct tttaagactc tgtttggcag ggatcttctg     240
gatgacctga atcagaact  aactggaaaa tttgaaaaat taattgtggc tctgatgaaa     300
ccctctcggc tttatgatgc ttatgaactg aaacatgcct tgaagggagc tggaacaaat     360
gaaaaagtac tgacagaaat tattgcttca aggacacctg aagaactgag agccatcaaa     420
caagtttatg aagaagaata tggctcaagc ctggaagatg acgtggtggg ggacacttca     480
gggtactacc agcggatgtt ggtggttctc cttcaggcta acagagaccc tgatgctgga     540
attgatgaag ctcaagttga acaagatgct caggctttat ttcaggctgg agaacttaaa     600
tgggggacag atgaagaaaa gtttatcacc atctttggaa cacgaagtgt gtctcatttg     660
```

```
agaaaggtgt tgacaagta catgactata tcaggatttc aaattgagga aaccattgac      720
cgcgagactt ctggcaattt agagcaacta ctccttgctg ttgtgaaatc tattcgaagt      780
atacctgcct accttgcaga gaccctctat tatgctatga agggagctgg gacagatgat      840 catacccctca tcagagtcat ggtttccagg agtgagattg atctgtttaa catcaggaag      900
gagtttagga agaattttgc cacctctctt tattccatga ttaagggaga tacatctggg      960
gactataaga aagctcttct gctgctctgt ggagaagatg acnnnagatc tcgatcgggc     1020
ctggaggtgc tgttccaggg ccccggaagt actnnngcac aggttctcag aggcactgtg     1080
actgacttcc ctggatttga tgagcgggct gatgcagaaa ctcttcggaa ggctatgaaa     1140
ggcttgggca cagatgagga gagcatcctg actctgttga catcccgaag taatgctcag     1200
cgccaggaaa tctctgcagc ttttaagact ctgtttggca gggatcttct ggatgacctg     1260
aaatcagaac taactggaaa atttgaaaaa ttaattgtgg ctctgatgaa accctctcgg     1320
ctttatgatg cttatgaact gaaacatgcc ttgaagggag ctggaacaaa tgaaaaagta     1380
ctgacagaaa ttattgcttc aaggacacct gaagaactga gagccatcaa acaagtttat     1440
gaagaagaat atggctcaag cctggaagat gacgtggtgg gggacacttc agggtactac     1500
cagcggatgt tggtggttct ccttcaggct aacagagacc ctgatgctgg aattgatgaa     1560
gctcaagttg aacaagatgc tcaggctta tttcaggctg agaacttaa atgggggaca       1620 gatgaagaaa agtttatcac catctttgga acacgaagtg tgtctcattt gagaaaggtg     1680
tttgacaagt acatgactat atcaggattt caaattgagg aaaccattga ccgcgagact     1740
tctggcaatt tagagcaact actccttgct gttgtgaaat ctattcgaag tatacctgcc     1800
taccttgcag agaccctcta ttatgctatg aagggagctg gacagatga tcatacccctc     1860 atcagagtca tggtttccag gagtgagatt gatctgttta acatcaggaa ggagtttagg     1920
aagaattttg ccacctctct ttattccatg attaagggag atacatctgg ggactataag     1980
aaagctcttc tgctgctctg tggagaagat gactaataat aa                       2022
```

<210> SEQ ID NO 5
<211> LENGTH: 2022
<212> TYPE: DNA
<213> ORGANISM: Artificial sequence
<220> FEATURE:
<223> OTHER INFORMATION: modified annexin gene
<220> FEATURE:
<221> NAME/KEY: CDS
<222> LOCATION: (1)..(2022)
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: misc_feature
<222> LOCATION: (1054)..(1056)
<223> OTHER INFORMATION: n is a, c, g, or t

<400> SEQUENCE: 5

```
atg gac tac aaa gac gat gac gac aag ctt gcg gcc gcg aat tcn gca        48
Met Asp Tyr Lys Asp Asp Asp Asp Lys Leu Ala Ala Ala Asn Xaa Ala
1               5                   10                  15 cag gtt ctc aga ggc act gtg act gac ttc cct gga ttt gat gag cgg        96
Gln Val Leu Arg Gly Thr Val Thr Asp Phe Pro Gly Phe Asp Glu Arg
            20                  25                  30
```

| | | |
|---|---|---|
| gct gat gca gaa act ctt cgg aag gct atg aaa ggc ttg ggc aca gat<br>Ala Asp Ala Glu Thr Leu Arg Lys Ala Met Lys Gly Leu Gly Thr Asp<br>35                    40                    45 | | 144 |
| gag gag agc atc ctg act ctg ttg aca tcc cga agt aat gct cag cgc<br>Glu Glu Ser Ile Leu Thr Leu Leu Thr Ser Arg Ser Asn Ala Gln Arg<br>50                    55                    60 | | 192 |
| cag gaa atc tct gca gct ttt aag act ctg ttt ggc agg gat ctt ctg<br>Gln Glu Ile Ser Ala Ala Phe Lys Thr Leu Phe Gly Arg Asp Leu Leu<br>65                    70                    75                    80 | | 240 |
| gat gac ctg aaa tca gaa cta act gga aaa ttt gaa aaa tta att gtg<br>Asp Asp Leu Lys Ser Glu Leu Thr Gly Lys Phe Glu Lys Leu Ile Val<br>85                    90                    95 | | 288 |
| gct ctg atg aaa ccc tct cgg ctt tat gat gct tat gaa ctg aaa cat<br>Ala Leu Met Lys Pro Ser Arg Leu Tyr Asp Ala Tyr Glu Leu Lys His<br>          100                    105                    110 | | 336 |
| gcc ttg aag gga gct gga aca aat gaa aaa gta ctg aca gaa att att<br>Ala Leu Lys Gly Ala Gly Thr Asn Glu Lys Val Leu Thr Glu Ile Ile<br>          115                    120                    125 | | 384 |
| gct tca agg aca cct gaa gaa ctg aga gcc atc aaa caa gtt tat gaa<br>Ala Ser Arg Thr Pro Glu Glu Leu Arg Ala Ile Lys Gln Val Tyr Glu<br>130                    135                    140 | | 432 |
| gaa gaa tat ggc tca agc ctg gaa gat gac gtg gtg ggg gac act tca<br>Glu Glu Tyr Gly Ser Ser Leu Glu Asp Asp Val Val Gly Asp Thr Ser<br>145                    150                    155                    160 | | 480 |
| ggg tac tac cag cgg atg ttg gtg gtt ctc ctt cag gct aac aga gac<br>Gly Tyr Tyr Gln Arg Met Leu Val Val Leu Leu Gln Ala Asn Arg Asp<br>                    165                    170                    175 | | 528 |
| cct gat gct gga att gat gaa gct caa gtt gaa caa gat gct cag gct<br>Pro Asp Ala Gly Ile Asp Glu Ala Gln Val Glu Gln Asp Ala Gln Ala<br>                  180                    185                    190 | | 576 |
| tta ttt cag gct gga gaa ctt aaa tgg ggg aca gat gaa gaa aag ttt<br>Leu Phe Gln Ala Gly Glu Leu Lys Trp Gly Thr Asp Glu Glu Lys Phe<br>          195                    200                    205 | | 624 |
| atc acc atc ttt gga aca cga agt gtg tct cat ttg aga aag gtg ttt<br>Ile Thr Ile Phe Gly Thr Arg Ser Val Ser His Leu Arg Lys Val Phe<br>210                    215                    220 | | 672 |
| gac aag tac atg act ata tca gga ttt caa att gag gaa acc att gac<br>Asp Lys Tyr Met Thr Ile Ser Gly Phe Gln Ile Glu Glu Thr Ile Asp<br>225                    230                    235                    240 | | 720 |
| cgc gag act tct ggc aat tta gag caa cta ctc ctt gct gtt gtg aaa<br>Arg Glu Thr Ser Gly Asn Leu Glu Gln Leu Leu Leu Ala Val Val Lys<br>                    245                    250                    255 | | 768 |
| tct att cga agt ata cct gcc tac ctt gca gag acc ctc tat tat gct<br>Ser Ile Arg Ser Ile Pro Ala Tyr Leu Ala Glu Thr Leu Tyr Tyr Ala<br>                    260                    265                    270 | | 816 |
| atg aag gga gct ggg aca gat gat cat acc ctc atc aga gtc atg gtt<br>Met Lys Gly Ala Gly Thr Asp Asp His Thr Leu Ile Arg Val Met Val<br>          275                    280                    285 | | 864 |
| tcc agg agt gag att gat ctg ttt aac atc agg aag gag ttt agg aag<br>Ser Arg Ser Glu Ile Asp Leu Phe Asn Ile Arg Lys Glu Phe Arg Lys<br>290                    295                    300 | | 912 |
| aat ttt gcc acc tct ctt tat tcc atg att aag gga gat aca tct ggg<br>Asn Phe Ala Thr Ser Leu Tyr Ser Met Ile Lys Gly Asp Thr Ser Gly<br>305                    310                    315                    320 | | 960 |
| gac tat aag aaa gct ctt ctg ctc tgt gga gaa gat gac nnn aga<br>Asp Tyr Lys Lys Ala Leu Leu Leu Cys Gly Glu Asp Asp Xaa Arg<br>                    325                    330                    335 | | 1008 |
| tct cga tcg ggc ctg gag gtg ctg ttc cag ggc ccc gga agt act nnn<br>Ser Arg Ser Gly Leu Glu Val Leu Phe Gln Gly Pro Gly Ser Thr Xaa | | 1056 |

```
                340              345              350
gca cag gtt ctc aga ggc act gtg act gac ttc cct gga ttt gat gag      1104
Ala Gln Val Leu Arg Gly Thr Val Thr Asp Phe Pro Gly Phe Asp Glu
        355              360              365 cgg gct gat gca gaa act ctt cgg aag gct atg aaa ggc ttg ggc aca      1152
Arg Ala Asp Ala Glu Thr Leu Arg Lys Ala Met Lys Gly Leu Gly Thr
    370              375              380 gat gag gag agc atc ctg act ctg ttg aca tcc cga agt aat gct cag      1200
Asp Glu Glu Ser Ile Leu Thr Leu Leu Thr Ser Arg Ser Asn Ala Gln
385              390              395              400 cgc cag gaa atc tct gca gct ttt aag act ctg ttt ggc agg gat ctt      1248
Arg Gln Glu Ile Ser Ala Ala Phe Lys Thr Leu Phe Gly Arg Asp Leu
            405              410              415 ctg gat gac ctg aaa tca gaa cta act gga aaa ttt gaa aaa tta att      1296
Leu Asp Asp Leu Lys Ser Glu Leu Thr Gly Lys Phe Glu Lys Leu Ile
        420              425              430 gtg gct ctg atg aaa ccc tct cgg ctt tat gat gct tat gaa ctg aaa      1344
Val Ala Leu Met Lys Pro Ser Arg Leu Tyr Asp Ala Tyr Glu Leu Lys
    435              440              445 cat gcc ttg aag gga gct gga aca aat gaa aaa gta ctg aca gaa att      1392
His Ala Leu Lys Gly Ala Gly Thr Asn Glu Lys Val Leu Thr Glu Ile
450              455              460 att gct tca agg aca cct gaa gaa ctg aga gcc atc aaa caa gtt tat      1440
Ile Ala Ser Arg Thr Pro Glu Glu Leu Arg Ala Ile Lys Gln Val Tyr
465              470              475              480 gaa gaa gaa tat ggc tca agc ctg gaa gat gac gtg gtg ggg gac act      1488
Glu Glu Glu Tyr Gly Ser Ser Leu Glu Asp Asp Val Val Gly Asp Thr
            485              490              495 tca ggg tac tac cag cgg atg ttg gtg gtt ctc ctt cag gct aac aga      1536
Ser Gly Tyr Tyr Gln Arg Met Leu Val Val Leu Leu Gln Ala Asn Arg
        500              505              510 gac cct gat gct gga att gat gaa gct caa gtt gaa caa gat gct cag      1584
Asp Pro Asp Ala Gly Ile Asp Glu Ala Gln Val Glu Gln Asp Ala Gln
    515              520              525 gct tta ttt cag gct gga gaa ctt aaa tgg ggg aca gat gaa gaa aag      1632
Ala Leu Phe Gln Ala Gly Glu Leu Lys Trp Gly Thr Asp Glu Glu Lys
530              535              540 ttt atc acc atc ttt gga aca cga agt gtg tct cat ttg aga aag gtg      1680
Phe Ile Thr Ile Phe Gly Thr Arg Ser Val Ser His Leu Arg Lys Val
545              550              555              560 ttt gac aag tac atg act ata tca gga ttt caa att gag gaa acc att      1728
Phe Asp Lys Tyr Met Thr Ile Ser Gly Phe Gln Ile Glu Glu Thr Ile
            565              570              575 gac cgc gag act tct ggc aat tta gag caa cta ctc ctt gct gtt gtg      1776
Asp Arg Glu Thr Ser Gly Asn Leu Glu Gln Leu Leu Leu Ala Val Val
        580              585              590 aaa tct att cga agt ata cct gcc tac ctt gca gag acc ctc tat tat      1824
Lys Ser Ile Arg Ser Ile Pro Ala Tyr Leu Ala Glu Thr Leu Tyr Tyr
    595              600              605 gct atg aag gga gct ggg aca gat gat cat acc ctc atc aga gtc atg      1872
Ala Met Lys Gly Ala Gly Thr Asp Asp His Thr Leu Ile Arg Val Met
610              615              620 gtt tcc agg agt gag att gat ctg ttt aac atc agg aag gag ttt agg      1920
Val Ser Arg Ser Glu Ile Asp Leu Phe Asn Ile Arg Lys Glu Phe Arg
625              630              635              640 aag aat ttt gcc acc tct ctt tat tcc atg att aag gga gat aca tct      1968
Lys Asn Phe Ala Thr Ser Leu Tyr Ser Met Ile Lys Gly Asp Thr Ser
            645              650              655 ggg gac tat aag aaa gct ctt ctg ctg ctc tgt gga gaa gat gac taa      2016
Gly Asp Tyr Lys Lys Ala Leu Leu Leu Leu Cys Gly Glu Asp Asp
```

```
Gly Asp Tyr Lys Lys Ala Leu Leu Leu Cys Gly Glu Asp Asp
            660                 665                 670 taa taa                                                             2022

<210> SEQ ID NO 6
<211> LENGTH: 671
<212> TYPE: PRT
<213> ORGANISM: Artificial sequence
<220> FEATURE:
<221> NAME/KEY: misc_feature
<222> LOCATION: (15)..(15)
<223> OTHER INFORMATION: The 'Xaa' at location 15 stands for Ser.
<220> FEATURE:
<221> NAME/KEY: misc_feature
<222> LOCATION: (335)..(335)
<223> OTHER INFORMATION: The 'Xaa' at location 335 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (352)..(352)
<223> OTHER INFORMATION: The 'Xaa' at location 352 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 6

Met Asp Tyr Lys Asp Asp Asp Lys Leu Ala Ala Asn Xaa Ala
1               5                   10                  15

Gln Val Leu Arg Gly Thr Val Thr Asp Phe Pro Gly Phe Asp Glu Arg
                20                  25                  30

Ala Asp Ala Glu Thr Leu Arg Lys Ala Met Lys Gly Leu Gly Thr Asp
            35                  40                  45

Glu Glu Ser Ile Leu Thr Leu Leu Thr Ser Arg Ser Asn Ala Gln Arg
    50                  55                  60

Gln Glu Ile Ser Ala Ala Phe Lys Thr Leu Phe Gly Arg Asp Leu Leu
65                  70                  75                  80

Asp Asp Leu Lys Ser Glu Leu Thr Gly Lys Phe Glu Lys Leu Ile Val
                85                  90                  95

Ala Leu Met Lys Pro Ser Arg Leu Tyr Asp Ala Tyr Glu Leu Lys His
                100                 105                 110

Ala Leu Lys Gly Ala Gly Thr Asn Glu Lys Val Leu Thr Glu Ile Ile
            115                 120                 125

Ala Ser Arg Thr Pro Glu Glu Leu Arg Ala Ile Lys Gln Val Tyr Glu
    130                 135                 140

Glu Glu Tyr Gly Ser Ser Leu Glu Asp Asp Val Val Gly Asp Thr Ser
145                 150                 155                 160

Gly Tyr Tyr Gln Arg Met Leu Val Val Leu Leu Gln Ala Asn Arg Asp
                165                 170                 175

Pro Asp Ala Gly Ile Asp Glu Ala Gln Val Glu Gln Asp Ala Gln Ala
            180                 185                 190

Leu Phe Gln Ala Gly Glu Leu Lys Trp Gly Thr Asp Glu Glu Lys Phe
    195                 200                 205

Ile Thr Ile Phe Gly Thr Arg Ser Val Ser His Leu Arg Lys Val Phe
210                 215                 220

Asp Lys Tyr Met Thr Ile Ser Gly Phe Gln Ile Glu Glu Thr Ile Asp
225                 230                 235                 240

Arg Glu Thr Ser Gly Asn Leu Glu Gln Leu Leu Leu Ala Val Val Lys
                245                 250                 255
```

```
Ser Ile Arg Ser Ile Pro Ala Tyr Leu Ala Glu Thr Leu Tyr Tyr Ala
            260                 265                 270

Met Lys Gly Ala Gly Thr Asp His Thr Leu Ile Arg Val Met Val
    275                 280                 285

Ser Arg Ser Glu Ile Asp Leu Phe Asn Ile Arg Lys Glu Phe Arg Lys
    290                 295                 300

Asn Phe Ala Thr Ser Leu Tyr Ser Met Ile Lys Gly Asp Thr Ser Gly
305                 310                 315                 320

Asp Tyr Lys Lys Ala Leu Leu Leu Cys Gly Glu Asp Asp Xaa Arg
                325                 330                 335

Ser Arg Ser Gly Leu Glu Val Leu Phe Gln Gly Pro Gly Ser Thr Xaa
                340                 345                 350

Ala Gln Val Leu Arg Gly Thr Val Thr Asp Phe Pro Gly Phe Asp Glu
            355                 360                 365

Arg Ala Asp Ala Glu Thr Leu Arg Lys Ala Met Lys Gly Leu Gly Thr
    370                 375                 380

Asp Glu Glu Ser Ile Leu Thr Leu Leu Thr Ser Arg Ser Asn Ala Gln
385                 390                 395                 400

Arg Gln Glu Ile Ser Ala Ala Phe Lys Thr Leu Phe Gly Arg Asp Leu
                405                 410                 415

Leu Asp Asp Leu Lys Ser Glu Leu Thr Gly Lys Phe Glu Lys Leu Ile
            420                 425                 430

Val Ala Leu Met Lys Pro Ser Arg Leu Tyr Asp Ala Tyr Glu Leu Lys
            435                 440                 445

His Ala Leu Lys Gly Ala Gly Thr Asn Glu Lys Val Leu Thr Glu Ile
    450                 455                 460

Ile Ala Ser Arg Thr Pro Glu Glu Leu Arg Ala Ile Lys Gln Val Tyr
465                 470                 475                 480

Glu Glu Glu Tyr Gly Ser Ser Leu Glu Asp Asp Val Val Gly Asp Thr
                485                 490                 495

Ser Gly Tyr Tyr Gln Arg Met Leu Val Val Leu Leu Gln Ala Asn Arg
            500                 505                 510

Asp Pro Asp Ala Gly Ile Asp Glu Ala Gln Val Glu Gln Asp Ala Gln
            515                 520                 525

Ala Leu Phe Gln Ala Gly Glu Leu Lys Trp Gly Thr Asp Glu Glu Lys
    530                 535                 540

Phe Ile Thr Ile Phe Gly Thr Arg Ser Val Ser His Leu Arg Lys Val
545                 550                 555                 560

Phe Asp Lys Tyr Met Thr Ile Ser Gly Phe Gln Ile Glu Glu Thr Ile
                565                 570                 575

Asp Arg Glu Thr Ser Gly Asn Leu Glu Gln Leu Leu Leu Ala Val Val
            580                 585                 590

Lys Ser Ile Arg Ser Ile Pro Ala Tyr Leu Ala Glu Thr Leu Tyr Tyr
            595                 600                 605

Ala Met Lys Gly Ala Gly Thr Asp Asp His Thr Leu Ile Arg Val Met
    610                 615                 620

Val Ser Arg Ser Glu Ile Asp Leu Phe Asn Ile Arg Lys Glu Phe Arg
625                 630                 635                 640

Lys Asn Phe Ala Thr Ser Leu Tyr Ser Met Ile Lys Gly Asp Thr Ser
                645                 650                 655

Gly Asp Tyr Lys Lys Ala Leu Leu Leu Cys Gly Glu Asp Asp
            660                 665                 670
```

```
<210> SEQ ID NO 7
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(30)
<223> OTHER INFORMATION: primer

<400> SEQUENCE: 7
acctgagtag tcgccatggc acaggttctc                                        30

<210> SEQ ID NO 8
<211> LENGTH: 36
<212> TYPE: DNA
<213> ORGANISM: Artificial sequence
<220> FEATURE:
<223> OTHER INFORMATION: primer

<400> SEQUENCE: 8
cccgaattca cgttagtcat cttctccaca gagcag                                 36

<210> SEQ ID NO 9
<211> LENGTH: 8
<212> TYPE: PRT
<213> ORGANISM: Artificial sequence
<220> FEATURE:
<223> OTHER INFORMATION: purification tag
<220> FEATURE:
<221> NAME/KEY: PEPTIDE
<222> LOCATION: (1)..(5)
<223> OTHER INFORMATION: flexible linker

<400> SEQUENCE: 9

Asp Tyr Lys Asp Asp Asp Asp Lys
1               5

<210> SEQ ID NO 10
<211> LENGTH: 966
<212> TYPE: DNA
<213> ORGANISM: Homo sapiens

<400> SEQUENCE: 10
atggccatgg caaccaaagg aggtactgtc aaagctgctt caggattcaa tgccatggaa       60
gatgcccaga ccctgaggaa ggccatgaaa gggctcggca ccgatgaaga cgccattatt      120
agcgtccttg cctaccgcaa caccgcccag cgccaggaga tcaggacagc ctacaagagc      180
accatcggca gggacttgat agacgacctg aagtcagaac tgagtggcaa cttcgagcag      240
gtgattgtgg gatgatgac gcccacggtg ctgtatgacg tgcaagagct gcgaagggcc       300
atgaagggag ccggcactga tgagggctgc ctaattgaga tcctggcctc ccggacccct      360
gaggagatcc ggcgcataag ccaaacctac cagcagcaat atggacggag ccttgaagat      420
gacattcgct ctgacacatc gttcatgttc cagcgagtgc tggtgtctct gtcagctggt      480
gggagggatg aaggaaatta ctggacgat gctctcgtga caggatgc ccaggacctg         540 tatgaggctg agagaagaa atgggggaca gatgaggtga atttctaac tgttctctgt       600 tcccggaacc gaaatcacct gttgcatgtg tttgatgaat acaaaaggat atcacagaag      660
gatattgaac agagtattaa atctgaaaca tctggtagct ttgaagatgc tctgctggct      720
atagtaaagt gcatgaggaa caaatctgca tattttgctg aaaagctcta taaatcgatg      780
aagggcttgg gcaccgatga taacacccct catcagagtga tggtttctcg agcagaaatt      840
```

```
gacatgttgg atatccgggc acacttcaag agactctatg gaaagtctct gtactcgttc      900
atcaagggtg acacatctgg agactacagg aaagtactgc ttgttctctg tggaggagat      960
gattaa                                                                  966

<210> SEQ ID NO 11
<211> LENGTH: 966
<212> TYPE: DNA
<213> ORGANISM: Homo sapiens
<220> FEATURE:
<221> NAME/KEY: CDS
<222> LOCATION: (1)..(966)

<400> SEQUENCE: 11 atg gcc atg gca acc aaa gga ggt act gtc aaa gct gct tca gga ttc       48
Met Ala Met Ala Thr Lys Gly Gly Thr Val Lys Ala Ala Ser Gly Phe
1               5                  10                  15 aat gcc atg gaa gat gcc cag acc ctg agg aag gcc atg aaa ggg ctc       96
Asn Ala Met Glu Asp Ala Gln Thr Leu Arg Lys Ala Met Lys Gly Leu
            20                  25                  30 ggc acc gat gaa gac gcc att att agc gtc ctt gcc tac cgc aac acc      144
Gly Thr Asp Glu Asp Ala Ile Ile Ser Val Leu Ala Tyr Arg Asn Thr
        35                  40                  45 gcc cag cgc cag gag atc agg aca gcc tac aag agc acc atc ggc agg      192
Ala Gln Arg Gln Glu Ile Arg Thr Ala Tyr Lys Ser Thr Ile Gly Arg
    50                  55                  60 gac ttg ata gac gac ctg aag tca gaa ctg agt ggc aac ttc gag cag      240
Asp Leu Ile Asp Asp Leu Lys Ser Glu Leu Ser Gly Asn Phe Glu Gln
65                  70                  75                  80 gtg att gtg ggg atg atg acg ccc acg gtg ctg tat gac gtg caa gag      288
Val Ile Val Gly Met Met Thr Pro Thr Val Leu Tyr Asp Val Gln Glu
                85                  90                  95 ctg cga agg gcc atg aag gga gcc ggc act gat gag ggc tgc cta att      336
Leu Arg Arg Ala Met Lys Gly Ala Gly Thr Asp Glu Gly Cys Leu Ile
            100                 105                 110 gag atc ctg gcc tcc cgg acc cct gag gag atc cgg cgc ata agc caa      384
Glu Ile Leu Ala Ser Arg Thr Pro Glu Glu Ile Arg Arg Ile Ser Gln
        115                 120                 125 acc tac cag cag caa tat gga cgg agc ctt gaa gat gac att cgc tct      432
Thr Tyr Gln Gln Gln Tyr Gly Arg Ser Leu Glu Asp Asp Ile Arg Ser
    130                 135                 140 gac aca tcg ttc atg ttc cag cga gtg ctg gtg tct ctg tca gct ggt      480
Asp Thr Ser Phe Met Phe Gln Arg Val Leu Val Ser Leu Ser Ala Gly
145                 150                 155                 160 ggg agg gat gaa gga aat tat ctg gac gat gct ctc gtg aga cag gat      528
Gly Arg Asp Glu Gly Asn Tyr Leu Asp Asp Ala Leu Val Arg Gln Asp
                165                 170                 175 gcc cag gac ctg tat gag gct gga gag aag aaa tgg ggg aca gat gag      576
Ala Gln Asp Leu Tyr Glu Ala Gly Glu Lys Lys Trp Gly Thr Asp Glu
            180                 185                 190 gtg aaa ttt cta act gtt ctc tgt tcc cgg aac cga aat cac ctg ttg      624
Val Lys Phe Leu Thr Val Leu Cys Ser Arg Asn Arg Asn His Leu Leu
        195                 200                 205 cat gtg ttt gat gaa tac aaa agg ata tca cag aag gat att gaa cag      672
His Val Phe Asp Glu Tyr Lys Arg Ile Ser Gln Lys Asp Ile Glu Gln
    210                 215                 220 agt att aaa tct gaa aca tct ggt agc ttt gaa gat gct ctg ctg gct      720
Ser Ile Lys Ser Glu Thr Ser Gly Ser Phe Glu Asp Ala Leu Leu Ala
225                 230                 235                 240 ata gta aag tgc atg agg aac aaa tct gca tat ttt gct gaa aag ctc      768
Ile Val Lys Cys Met Arg Asn Lys Ser Ala Tyr Phe Ala Glu Lys Leu
```

```
Ile Val Lys Cys Met Arg Asn Lys Ser Ala Tyr Phe Ala Glu Lys Leu
                245                 250                 255 tat aaa tcg atg aag ggc ttg ggc acc gat gat aac acc ctc atc aga         816
Tyr Lys Ser Met Lys Gly Leu Gly Thr Asp Asp Asn Thr Leu Ile Arg
        260                 265                 270 gtg atg gtt tct cga gca gaa att gac atg ttg gat atc cgg gca cac         864
Val Met Val Ser Arg Ala Glu Ile Asp Met Leu Asp Ile Arg Ala His
    275                 280                 285 ttc aag aga ctc tat gga aag tct ctg tac tcg ttc atc aag ggt gac         912
Phe Lys Arg Leu Tyr Gly Lys Ser Leu Tyr Ser Phe Ile Lys Gly Asp
290                 295                 300 aca tct gga gac tac agg aaa gta ctg ctt gtt ctc tgt gga gga gat         960
Thr Ser Gly Asp Tyr Arg Lys Val Leu Leu Val Leu Cys Gly Gly Asp
305                 310                 315                 320 gat taa                                                                 966
Asp
```

<210> SEQ ID NO 12
<211> LENGTH: 321
<212> TYPE: PRT
<213> ORGANISM: Homo sapiens

<400> SEQUENCE: 12

```
Met Ala Met Ala Thr Lys Gly Gly Thr Val Lys Ala Ala Ser Gly Phe
1               5                   10                  15

Asn Ala Met Glu Asp Ala Gln Thr Leu Arg Lys Ala Met Lys Gly Leu
                20                  25                  30

Gly Thr Asp Glu Asp Ala Ile Ile Ser Val Leu Ala Tyr Arg Asn Thr
            35                  40                  45

Ala Gln Arg Gln Glu Ile Arg Thr Ala Tyr Lys Ser Thr Ile Gly Arg
        50                  55                  60

Asp Leu Ile Asp Asp Leu Lys Ser Glu Leu Ser Gly Asn Phe Glu Gln
65                  70                  75                  80

Val Ile Val Gly Met Met Thr Pro Thr Val Leu Tyr Asp Val Gln Glu
                85                  90                  95

Leu Arg Arg Ala Met Lys Gly Ala Gly Thr Asp Glu Gly Cys Leu Ile
            100                 105                 110

Glu Ile Leu Ala Ser Arg Thr Pro Glu Glu Ile Arg Arg Ile Ser Gln
        115                 120                 125

Thr Tyr Gln Gln Gln Tyr Gly Arg Ser Leu Glu Asp Asp Ile Arg Ser
    130                 135                 140

Asp Thr Ser Phe Met Phe Gln Arg Val Leu Val Ser Leu Ser Ala Gly
145                 150                 155                 160

Gly Arg Asp Glu Gly Asn Tyr Leu Asp Asp Ala Leu Val Arg Gln Asp
                165                 170                 175

Ala Gln Asp Leu Tyr Glu Ala Gly Glu Lys Lys Trp Gly Thr Asp Glu
            180                 185                 190

Val Lys Phe Leu Thr Val Leu Cys Ser Arg Asn Arg Asn His Leu Leu
        195                 200                 205

His Val Phe Asp Glu Tyr Lys Arg Ile Ser Gln Lys Asp Ile Glu Gln
    210                 215                 220

Ser Ile Lys Ser Glu Thr Ser Gly Ser Phe Glu Asp Ala Leu Leu Ala
225                 230                 235                 240

Ile Val Lys Cys Met Arg Asn Lys Ser Ala Tyr Phe Ala Glu Lys Leu
                245                 250                 255

Tyr Lys Ser Met Lys Gly Leu Gly Thr Asp Asp Asn Thr Leu Ile Arg
```

-continued

```
                260                 265                 270
Val Met Val Ser Arg Ala Glu Ile Asp Met Leu Asp Ile Arg Ala His
            275                 280                 285

Phe Lys Arg Leu Tyr Gly Lys Ser Leu Tyr Ser Phe Ile Lys Gly Asp
        290                 295                 300

Thr Ser Gly Asp Tyr Arg Lys Val Leu Leu Val Leu Cys Gly Gly Asp
305                 310                 315                 320

Asp
```

<210> SEQ ID NO 13
<211> LENGTH: 984
<212> TYPE: DNA
<213> ORGANISM: Homo sapiens

<400> SEQUENCE: 13

```
atggcctggt ggaaagcctg gattgaacag gagggtgtca cagtgaagag cagctcccac      60
ttcaacccag accctgatgc agagaccctc tacaaagcca tgaaggggat cgggaccaac     120
gagcaggcta tcatcgatgt gctcaccaag agaagcaaca cgcagcggca gcagatcgcc     180
aagtccttca ggctcagtt cggcaaggac ctcactgaga ccttgaagtc tgagctcagt     240
ggcaagtttg agaggctcat tgtggcccct atgtatccgc catacagata cgaagccaag     300
gagctgcatg acgccatgaa gggcttagga accaaggagg tgtcatcat tgagatcctg     360
gcctctcgga ccaagaacca gctgcgggag ataatgaagg cgtatgagga agactatggg     420
tccagcctgg aggaggacat ccaagcagac acaagtggct acctggagag gatcctggtg     480
tgcctcctgc agggcagcag ggatgatgtg agcagctttg tggacccggc actggccctc     540
caagacgcac aggatctgta tgcggcaggc gagaagattc gtgggactga tgagatgaaa     600
ttcatcacca tcctgtgcac gcgcagtgcc actcacctgc tgagagtgtt tgaagagtat     660
gagaaaattg ccaacaagag cattgaggac agcatcaaga gtgagaccca tggctcactg     720
gaggaggcca tgctcactgt ggtgaaatgc acccaaaaacc tccacagcta ctttgcagag     780
agactctact atgccatgaa gggagcaggg acgcgtgatg ggaccctgat aagaaacatc     840
gtttcaagga gcgagattga cttaaatctt atcaaatgtc acttcaagaa gatgtacggc     900
aagaccctca gcagcatgat catggaagac caccagcggcg actacaagaa cgccctgctg     960
agcctggtgg gcagcgaccc ctga                                               984
```

<210> SEQ ID NO 14
<211> LENGTH: 984
<212> TYPE: DNA
<213> ORGANISM: Homo sapiens
<220> FEATURE:
<221> NAME/KEY: CDS
<222> LOCATION: (1)..(984)

<400> SEQUENCE: 14

```
atg gcc tgg tgg aaa gcc tgg att gaa cag gag ggt gtc aca gtg aag       48
Met Ala Trp Trp Lys Ala Trp Ile Glu Gln Glu Gly Val Thr Val Lys
1               5                   10                  15 agc agc tcc cac ttc aac cca gac cct gat gca gag acc ctc tac aaa       96
Ser Ser Ser His Phe Asn Pro Asp Pro Asp Ala Glu Thr Leu Tyr Lys
            20                  25                  30 gcc atg aag ggg atc ggg acc aac gag cag gct atc atc gat gtg ctc      144
Ala Met Lys Gly Ile Gly Thr Asn Glu Gln Ala Ile Ile Asp Val Leu
        35                  40                  45 acc aag aga agc aac acg cag cgg cag cag atc gcc aag tcc ttc aag      192
```

|  |  |  |  |  |  |  |  |  |  |  |  |  |  |  |
|---|---|---|---|---|---|---|---|---|---|---|---|---|---|---|
| Thr | Lys | Arg | Ser | Asn | Thr | Gln | Arg | Gln | Gln | Ile | Ala | Lys | Ser | Phe | Lys |
|  | 50 |  |  |  | 55 |  |  |  | 60 |  |  |  |  |  |  |

```
gct cag ttc ggc aag gac ctc act gag acc ttg aag tct gag ctc agt       240
Ala Gln Phe Gly Lys Asp Leu Thr Glu Thr Leu Lys Ser Glu Leu Ser
 65          70                  75                  80 ggc aag ttt gag agg ctc att gtg gcc ctt atg tat ccg cca tac aga       288
Gly Lys Phe Glu Arg Leu Ile Val Ala Leu Met Tyr Pro Pro Tyr Arg
             85                  90                  95 tac gaa gcc aag gag ctg cat gac gcc atg aag ggc tta gga acc aag       336
Tyr Glu Ala Lys Glu Leu His Asp Ala Met Lys Gly Leu Gly Thr Lys
                100                 105                 110 gag ggt gtc atc att gag atc ctg gcc tct cgg acc aag aac cag ctg       384
Glu Gly Val Ile Ile Glu Ile Leu Ala Ser Arg Thr Lys Asn Gln Leu
            115                 120                 125 cgg gag ata atg aag gcg tat gag gaa gac tat ggg tcc agc ctg gag       432
Arg Glu Ile Met Lys Ala Tyr Glu Glu Asp Tyr Gly Ser Ser Leu Glu
        130                 135                 140 gag gac atc caa gca gac aca agt ggc tac ctg gag agg atc ctg gtg       480
Glu Asp Ile Gln Ala Asp Thr Ser Gly Tyr Leu Glu Arg Ile Leu Val
145                 150                 155                 160 tgc ctc ctg cag ggc agc agg gat gat gtg agc agc ttt gtg gac ccg       528
Cys Leu Leu Gln Gly Ser Arg Asp Asp Val Ser Ser Phe Val Asp Pro
                165                 170                 175 gca ctg gcc ctc caa gac gca cag gat ctg tat gcg gca ggc gag aag       576
Ala Leu Ala Leu Gln Asp Ala Gln Asp Leu Tyr Ala Ala Gly Glu Lys
            180                 185                 190 att cgt ggg act gat gag atg aaa ttc atc acc atc ctg tgc acg cgc       624
Ile Arg Gly Thr Asp Glu Met Lys Phe Ile Thr Ile Leu Cys Thr Arg
        195                 200                 205 agt gcc act cac ctg ctg aga gtg ttt gaa gag tat gag aaa att gcc       672
Ser Ala Thr His Leu Leu Arg Val Phe Glu Glu Tyr Glu Lys Ile Ala
210                 215                 220 aac aag agc att gag gac agc atc aag agt gag acc cat ggc tca ctg       720
Asn Lys Ser Ile Glu Asp Ser Ile Lys Ser Glu Thr His Gly Ser Leu
225                 230                 235                 240 gag gag gcc atg ctc act gtg gtg aaa tgc acc caa aac ctc cac agc       768
Glu Glu Ala Met Leu Thr Val Val Lys Cys Thr Gln Asn Leu His Ser
                245                 250                 255 tac ttt gca gag aga ctc tac tat gcc atg aag gga gca ggg acg cgt       816
Tyr Phe Ala Glu Arg Leu Tyr Tyr Ala Met Lys Gly Ala Gly Thr Arg
            260                 265                 270 gat ggg acc ctg ata aga aac atc gtt tca agg agc gag att gac tta       864
Asp Gly Thr Leu Ile Arg Asn Ile Val Ser Arg Ser Glu Ile Asp Leu
        275                 280                 285 aat ctt atc aaa tgt cac ttc aag aag atg tac ggc aag acc ctc agc       912
Asn Leu Ile Lys Cys His Phe Lys Lys Met Tyr Gly Lys Thr Leu Ser
    290                 295                 300 agc atg atc atg gaa gac acc agc ggc gac tac aag aac gcc ctg ctg       960
Ser Met Ile Met Glu Asp Thr Ser Gly Asp Tyr Lys Asn Ala Leu Leu
305                 310                 315                 320 agc ctg gtg ggc agc gac ccc tga                                       984
Ser Leu Val Gly Ser Asp Pro
                325
```

<210> SEQ ID NO 15
<211> LENGTH: 327
<212> TYPE: PRT
<213> ORGANISM: Homo sapiens

<400> SEQUENCE: 15

Met Ala Trp Trp Lys Ala Trp Ile Glu Gln Glu Gly Val Thr Val Lys
1               5                   10                  15

Ser Ser Ser His Phe Asn Pro Asp Pro Asp Ala Glu Thr Leu Tyr Lys
            20                  25                  30

Ala Met Lys Gly Ile Gly Thr Asn Glu Gln Ala Ile Ile Asp Val Leu
        35                  40                  45

Thr Lys Arg Ser Asn Thr Gln Arg Gln Gln Ile Ala Lys Ser Phe Lys
50                  55                  60

Ala Gln Phe Gly Lys Asp Leu Thr Glu Thr Leu Lys Ser Glu Leu Ser
65                  70                  75                  80

Gly Lys Phe Glu Arg Leu Ile Val Ala Leu Met Tyr Pro Pro Tyr Arg
            85                  90                  95

Tyr Glu Ala Lys Glu Leu His Asp Ala Met Lys Gly Leu Gly Thr Lys
            100                 105                 110

Glu Gly Val Ile Ile Glu Ile Leu Ala Ser Arg Thr Lys Asn Gln Leu
        115                 120                 125

Arg Glu Ile Met Lys Ala Tyr Glu Glu Asp Tyr Gly Ser Ser Leu Glu
130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
            165                 170                 175

Ala Leu Ala Leu Gln Asp Ala Gln Asp Leu Tyr Ala Ala Gly Glu Lys
            180                 185                 190

Ile Arg Gly Thr Asp Glu Met Lys Phe Ile Thr Ile Leu Cys Thr Arg
        195                 200                 205

Ser Ala Thr His Leu Leu Arg Val Phe Glu Glu Tyr Glu Lys Ile Ala
210                 215                 220

Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
            245                 250                 255

Tyr Phe Ala Glu Arg Leu Tyr Tyr Ala Met Lys Gly Ala Gly Thr Arg
            260                 265                 270

Asp Gly Thr Leu Ile Arg Asn Ile Val Ser Arg Ser Glu Ile Asp Leu
        275                 280                 285

Asn Leu Ile Lys Cys His Phe Lys Lys Met Tyr Gly Lys Thr Leu Ser
290                 295                 300

Ser Met Ile Met Glu Asp Thr Ser Gly Asp Tyr Lys Asn Ala Leu Leu
305                 310                 315                 320

Ser Leu Val Gly Ser Asp Pro
            325

<210> SEQ ID NO 16
<211> LENGTH: 7221
<212> TYPE: DNA
<213> ORGANISM: Artificial sequence
<220> FEATURE:
<223> OTHER INFORMATION: plasmid

<400> SEQUENCE: 16
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tccctttagg    180

```
gttccgattt agtgctttac ggcacctcga ccccaaaaaa cttgattagg gtgatggttc    240
acgtagtggg ccatcgccct gatagacggt ttttcgccct tgacgttgg agtccacgtt    300 ctttaatagt ggactcttgt tccaaactgg aacaacactc aaccctatct cggtctattc    360
ttttgattta aagggatttt gccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatatttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg cttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
```

```
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga ctgtcttcg gtatcgtcgt   3780 atcccactac cgagatgtcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttcccccatc ggtgatgtcg gcgatatagg cgccagcaac cgcacctgtg   4920
```

-continued

```
gcgccggtga tgccggccac gatgcgtccg gcgtagagga tcgagatcga tctcgatccc    4980
gcgaaattaa tacgactcac tatagggaa ttgtgagcgg ataacaattc ccctctagaa      5040
ataattttgt ttaactttaa gaaggagata tacatatggc catggcaacc aaaggaggta    5100
ctgtcaaagc tgcttcagga ttcaatgcca tggaagatgc ccagaccctg aggaaggcca    5160
tgaaagggct cggcaccgat gaagacgcca ttattagcgt ccttgcctac cgcaacaccg    5220
cccagcgcca ggagatcagg acagcctaca agagcaccat cggcagggac ttgatagacg    5280
acctgaagtc agaactgagt ggcaacttcg agcaggtgat tgtggggatg atgacgccca    5340
cggtgctgta tgacgtgcaa gagctgcgaa gggccatgaa gggagccggc actgatgagg    5400
gctgcctaat tgagatcctg gcctcccgga cccctgagga gatccggcgc ataagccaaa    5460
cctaccagca gcaatatgga cggaggcttg aagatgacat tcgctctgac acatcgttca    5520
tgttccagcg agtgctggtg tctctgtcag ctggtgggag ggatgaagga aattatctgg    5580
acgatgctct cgtgagacag gatgcccagg acctgtatga ggctgagag aagaaatggg    5640
ggacagatga ggtgaaattt ctaactgttc tctgttcccg gaaccgaaat cacctgttgc    5700
atgtgtttga tgaatacaaa aggatatcac agaaggatat tgaacagagt attaaatctg    5760
aaacatctgg tagctttgaa gatgctctgc tggctatagt aaagtgcatg aggaacaaat    5820
ctgcatattt tgctgaaaag ctctataaat cgatgaaggg cttgggcacc gatgataaca    5880
ccctcatcag agtgatggtt tctcgagcag aaattgacat gttggatatc cgggcacact    5940
tcaagagact ctatggaaag tctctgtact cgttcatcaa gggtgacaca tctggagact    6000
acaggaaagt actgcttgtt ctctgtggag gagatgatgg atccctggag gtgctgttcc    6060
agggcccctc cggaagctt gccatggcaa ccaaaggagg tactgtcaaa gctgcttcag    6120
gattcaatgc catggaagat gcccagaccc tgaggaaggc catgaaaggg ctcggcaccg    6180
atgaagacgc cattattagc gtccttgcct accgcaacac cgcccagcgc caggagatca    6240
ggacagccta caagagcacc atcggcaggg acttgataga cgacctgaag tcagaactga    6300
gtggcaactt cgagcaggtg attgtgggga tgatgacgcc cacggtgctg tatgacgtgc    6360
aagagctgcg aagggccatg aagggagccg gcactgatga gggctgccta attgagatcc    6420
tggcctcccg gacccctgag gagatccggc gcataagcca aacctaccag cagcaatatg    6480
gacggaggct tgaagatgac attcgctctg acacatcgtt catgttccag cgagtgctgg    6540
tgtctctgtc agctggtggg agggatgaag gaaattatct ggacgatgct ctcgtgagac    6600
aggatgccca ggacctgtat gaggctgagag aagaaatg ggggacagat gaggtgaaat    6660
ttctaactgt tctctgttcc cggaaccgaa atcacctgtt gcatgtgttt gatgaataca    6720
aaaggatatc acagaaggat attgaacaga gtattaaatc tgaaacatct ggtagctttg    6780
aagatgctct gctggctata gtaaagtgca tgaggaacaa atctgcatat tttgctgaaa    6840
agctctataa atcgatgaag gcttgggca ccgatgataa caccctcatc agagtgatgg    6900
tttctcgagc agaaattgac atgttggata tccgggcaca cttcaagaga ctctatggaa    6960
agtctctgta ctcgttcatc aagggtgaca catctggaga ctacaggaaa gtactgcttg    7020
ttctctgtgg aggagatgat aatagtaag cggccgcact cgagcaccac caccaccacc    7080
actgagatcc ggctgctaac aaagcccgaa aggaagctga gttggctgct gccaccgctg    7140
agcaataact agcataaccc cttggggcct ctaaacgggt cttgaggggt tttttgctga    7200
aaggaggaac tatatccgga t                                              7221
```

<210> SEQ ID NO 17
<211> LENGTH: 1974
<212> TYPE: DNA
<213> ORGANISM: Artificial sequence
<220> FEATURE:
<223> OTHER INFORMATION: plasmid

<400> SEQUENCE: 17

| | | | | | |
|---|---|---|---|---|---|
| atggccatgg | caaccaaagg | aggtactgtc | aaagctgctt | caggattcaa | tgccatggaa | 60 |
| gatgcccaga | ccctgaggaa | ggccatgaaa | gggctcggca | ccgatgaaga | cgccattatt | 120 |
| agcgtccttg | cctaccgcaa | caccgcccag | cgccaggaga | tcaggacagc | ctacaagagc | 180 |
| accatcggca | gggacttgat | agacgacctg | aagtcagaac | tgagtggcaa | cttcgagcag | 240 |
| gtgattgtgg | ggatgatgac | gcccacggtg | ctgtatgacg | tgcaagagct | gcgaagggcc | 300 |
| atgaagggag | ccggcactga | tgagggctgc | ctaattgaga | tcctggcctc | ccggacccct | 360 |
| gaggagatcc | ggcgcataag | ccaaacctac | cagcagcaat | atggacggag | gcttgaagat | 420 |
| gacattcgct | ctgacacatc | gttcatgttc | agcgagtgc | tggtgtctct | gtcagctggt | 480 |
| gggaggatg | aaggaaatta | tctggacgat | gctctcgtga | acaggatgc | ccaggacctg | 540 |
| tatgaggctg | gagagaagaa | atgggggaca | gatgaggtga | aatttctaac | tgttctctgt | 600 |
| tcccggaacc | gaaatcacct | gttgcatgtg | tttgatgaat | acaaaaggat | atcacagaag | 660 |
| gatattgaac | agagtattaa | atctgaaaca | tctggtagct | ttgaagatgc | tctgctggct | 720 |
| atagtaaagt | gcatgaggaa | caaatctgca | tattttgctg | aaaagctcta | taaatcgatg | 780 |
| aagggcttgg | gcaccgatga | taacaccctc | atcagagtga | tggtttctcg | agcagaaatt | 840 |
| gacatgttgg | atatccgggc | acacttcaag | agactctatg | aaagtctct | gtactcgttc | 900 |
| atcaagggtg | acacatctgg | agactacagg | aagtactgc | ttgttctctg | tggaggagat | 960 |
| gatggatccc | tggaggtgct | gttccagggc | ccctccggga | agcttgccat | ggcaaccaaa | 1020 |
| ggaggtactg | tcaaagctgc | ttcaggattc | aatgccatgg | aagatgccca | gaccctgagg | 1080 |
| aaggccatga | aagggctcgg | caccgatgaa | gacgccatta | ttagcgtcct | tgcctaccgc | 1140 |
| aacaccgccc | agcgccagga | gatcaggaca | gcctacaaga | gcaccatcgg | cagggacttg | 1200 |
| atagacgacc | tgaagtcaga | actgagtggc | aacttcgagc | aggtgattgt | ggggatgatg | 1260 |
| acgcccacgg | tgctgtatga | cgtgcaagag | ctgcgaaggg | ccatgaaggg | agccggcact | 1320 |
| gatgagggct | gcctaattga | gatcctggcc | tcccggaccc | ctgaggagat | ccggcgcata | 1380 |
| agccaaacct | accagcagca | atatggacgg | aggcttgaag | atgacattcg | ctctgacaca | 1440 |
| tcgttcatgt | tccagcgagt | gctggtgtct | ctgtcagctg | gtgggaggga | tgaaggaaat | 1500 |
| tatctggacg | atgctctcgt | gagacaggat | gcccaggacc | tgtatgaggc | tggagagaag | 1560 |
| aaatgggga | cagatgaggt | gaaatttcta | actgttctct | gttcccggaa | ccgaaatcac | 1620 |
| ctgttgcatg | tgtttgatga | atacaaaagg | atatcacaga | aggatattga | acagagtatt | 1680 |
| aaatctgaaa | catctggtag | cttttgaagat | gctctgctgg | ctatagtaaa | gtgcatgagg | 1740 |
| aacaaatctg | catattttgc | tgaaaagctc | tataaatcga | tgaagggctt | gggcaccgat | 1800 |
| gataacaccc | tcatcagagt | gatggtttct | cgagcagaaa | ttgacatgtt | ggatatccgg | 1860 |
| gcacacttca | agagactcta | tgaaagtct | ctgtactcgt | tcatcaaggg | tgacacatct | 1920 |
| ggagactaca | ggaaagtact | gcttgttctc | tgtggaggag | atgattaata | gtaa | 1974 |

<210> SEQ ID NO 18
<211> LENGTH: 1974
<212> TYPE: DNA

<213> ORGANISM: Artificial sequence
<220> FEATURE:
<223> OTHER INFORMATION: plasmid
<220> FEATURE:
<221> NAME/KEY: CDS
<222> LOCATION: (1)..(1974)

<400> SEQUENCE: 18

| | | | | | | | | | | | | | | | | |
|---|---|---|---|---|---|---|---|---|---|---|---|---|---|---|---|---|
| atg | gcc | atg | gca | acc | aaa | gga | ggt | act | gtc | aaa | gct | gct | tca | gga | ttc | 48 |
| Met | Ala | Met | Ala | Thr | Lys | Gly | Gly | Thr | Val | Lys | Ala | Ala | Ser | Gly | Phe | |
| 1 | | | | 5 | | | | | 10 | | | | | 15 | | |
| aat | gcc | atg | gaa | gat | gcc | cag | acc | ctg | agg | aag | gcc | atg | aaa | ggg | ctc | 96 |
| Asn | Ala | Met | Glu | Asp | Ala | Gln | Thr | Leu | Arg | Lys | Ala | Met | Lys | Gly | Leu | |
| | | | 20 | | | | | 25 | | | | | 30 | | | |
| ggc | acc | gat | gaa | gac | gcc | att | att | agc | gtc | ctt | gcc | tac | cgc | aac | acc | 144 |
| Gly | Thr | Asp | Glu | Asp | Ala | Ile | Ile | Ser | Val | Leu | Ala | Tyr | Arg | Asn | Thr | |
| | 35 | | | | | 40 | | | | | 45 | | | | | |
| gcc | cag | cgc | cag | gag | atc | agg | aca | gcc | tac | aag | agc | acc | atc | ggc | agg | 192 |
| Ala | Gln | Arg | Gln | Glu | Ile | Arg | Thr | Ala | Tyr | Lys | Ser | Thr | Ile | Gly | Arg | |
| 50 | | | | | 55 | | | | | 60 | | | | | | |
| gac | ttg | ata | gac | gac | ctg | aag | tca | gaa | ctg | agt | ggc | aac | ttc | gag | cag | 240 |
| Asp | Leu | Ile | Asp | Asp | Leu | Lys | Ser | Glu | Leu | Ser | Gly | Asn | Phe | Glu | Gln | |
| 65 | | | | | 70 | | | | | 75 | | | | | 80 | |
| gtg | att | gtg | ggg | atg | atg | acg | ccc | acg | gtg | ctg | tat | gac | gtg | caa | gag | 288 |
| Val | Ile | Val | Gly | Met | Met | Thr | Pro | Thr | Val | Leu | Tyr | Asp | Val | Gln | Glu | |
| | | | | 85 | | | | | 90 | | | | | 95 | | |
| ctg | cga | agg | gcc | atg | aag | gga | gcc | ggc | act | gat | gag | ggc | tgc | cta | att | 336 |
| Leu | Arg | Arg | Ala | Met | Lys | Gly | Ala | Gly | Thr | Asp | Glu | Gly | Cys | Leu | Ile | |
| | | | 100 | | | | | 105 | | | | | 110 | | | |
| gag | atc | ctg | gcc | tcc | cgg | acc | cct | gag | gag | atc | cgg | cgc | ata | agc | caa | 384 |
| Glu | Ile | Leu | Ala | Ser | Arg | Thr | Pro | Glu | Glu | Ile | Arg | Arg | Ile | Ser | Gln | |
| | 115 | | | | | 120 | | | | | 125 | | | | | |
| acc | tac | cag | cag | caa | tat | gga | cgg | agg | ctt | gaa | gat | gac | att | cgc | tct | 432 |
| Thr | Tyr | Gln | Gln | Gln | Tyr | Gly | Arg | Arg | Leu | Glu | Asp | Asp | Ile | Arg | Ser | |
| 130 | | | | | 135 | | | | | 140 | | | | | | |
| gac | aca | tcg | ttc | atg | ttc | cag | cga | gtg | ctg | gtg | tct | ctg | tca | gct | ggt | 480 |
| Asp | Thr | Ser | Phe | Met | Phe | Gln | Arg | Val | Leu | Val | Ser | Leu | Ser | Ala | Gly | |
| 145 | | | | | 150 | | | | | 155 | | | | | 160 | |
| ggg | agg | gat | gaa | gga | aat | tat | ctg | gac | gat | gct | ctc | gtg | aga | cag | gat | 528 |
| Gly | Arg | Asp | Glu | Gly | Asn | Tyr | Leu | Asp | Asp | Ala | Leu | Val | Arg | Gln | Asp | |
| | | | | 165 | | | | | 170 | | | | | 175 | | |
| gcc | cag | gac | ctg | tat | gag | gct | gga | gag | aag | aaa | tgg | ggg | aca | gat | gag | 576 |
| Ala | Gln | Asp | Leu | Tyr | Glu | Ala | Gly | Glu | Lys | Lys | Trp | Gly | Thr | Asp | Glu | |
| | | | 180 | | | | | 185 | | | | | 190 | | | |
| gtg | aaa | ttt | cta | act | gtt | ctc | tgt | tcc | cgg | aac | cga | aat | cac | ctg | ttg | 624 |
| Val | Lys | Phe | Leu | Thr | Val | Leu | Cys | Ser | Arg | Asn | Arg | Asn | His | Leu | Leu | |
| | 195 | | | | | 200 | | | | | 205 | | | | | |
| cat | gtg | ttt | gat | gaa | tac | aaa | agg | ata | tca | cag | aag | gat | att | gaa | cag | 672 |
| His | Val | Phe | Asp | Glu | Tyr | Lys | Arg | Ile | Ser | Gln | Lys | Asp | Ile | Glu | Gln | |
| 210 | | | | | 215 | | | | | 220 | | | | | | |
| agt | att | aaa | tct | gaa | aca | tct | ggt | agc | ttt | gaa | gat | gct | ctg | ctg | gct | 720 |
| Ser | Ile | Lys | Ser | Glu | Thr | Ser | Gly | Ser | Phe | Glu | Asp | Ala | Leu | Leu | Ala | |
| 225 | | | | | 230 | | | | | 235 | | | | | 240 | |
| ata | gta | aag | tgc | atg | agg | aac | aaa | tct | gca | tat | ttt | gct | gaa | aag | ctc | 768 |
| Ile | Val | Lys | Cys | Met | Arg | Asn | Lys | Ser | Ala | Tyr | Phe | Ala | Glu | Lys | Leu | |
| | | | | 245 | | | | | 250 | | | | | 255 | | |
| tat | aaa | tcg | atg | aag | ggc | ttg | ggc | acc | gat | gat | aac | acc | ctc | atc | aga | 816 |
| Tyr | Lys | Ser | Met | Lys | Gly | Leu | Gly | Thr | Asp | Asp | Asn | Thr | Leu | Ile | Arg | |
| | | | 260 | | | | | 265 | | | | | 270 | | | |
| gtg | atg | gtt | tct | cga | gca | gaa | att | gac | atg | ttg | gat | atc | cgg | gca | cac | 864 |
| Val | Met | Val | Ser | Arg | Ala | Glu | Ile | Asp | Met | Leu | Asp | Ile | Arg | Ala | His | |

-continued

```
                275                 280                 285
ttc aag aga ctc tat gga aag tct ctg tac tcg ttc atc aag ggt gac    912
Phe Lys Arg Leu Tyr Gly Lys Ser Leu Tyr Ser Phe Ile Lys Gly Asp
        290                 295                 300 aca tct gga gac tac agg aaa gta ctg ctt gtt ctc tgt gga gga gat    960
Thr Ser Gly Asp Tyr Arg Lys Val Leu Leu Val Leu Cys Gly Gly Asp
305                 310                 315                 320 gat gga tcc ctg gag gtg ctg ttc cag ggc ccc tcc ggg aag ctt gcc   1008
Asp Gly Ser Leu Glu Val Leu Phe Gln Gly Pro Ser Gly Lys Leu Ala
                325                 330                 335 atg gca acc aaa gga ggt act gtc aaa gct gct tca gga ttc aat gcc   1056
Met Ala Thr Lys Gly Gly Thr Val Lys Ala Ala Ser Gly Phe Asn Ala
            340                 345                 350 atg gaa gat gcc cag acc ctg agg aag gcc atg aaa ggg ctc ggc acc   1104
Met Glu Asp Ala Gln Thr Leu Arg Lys Ala Met Lys Gly Leu Gly Thr
                355                 360                 365 gat gaa gac gcc att att agc gtc ctt gcc tac cgc aac acc gcc cag   1152
Asp Glu Asp Ala Ile Ile Ser Val Leu Ala Tyr Arg Asn Thr Ala Gln
        370                 375                 380 cgc cag gag atc agg aca gcc tac aag agc acc atc ggc agg gac ttg   1200
Arg Gln Glu Ile Arg Thr Ala Tyr Lys Ser Thr Ile Gly Arg Asp Leu
385                 390                 395                 400 ata gac gac ctg aag tca gaa ctg agt ggc aac ttc gag cag gtg att   1248
Ile Asp Asp Leu Lys Ser Glu Leu Ser Gly Asn Phe Glu Gln Val Ile
                405                 410                 415 gtg ggg atg atg acg ccc acg gtg ctg tat gac gtg caa gag ctg cga   1296
Val Gly Met Met Thr Pro Thr Val Leu Tyr Asp Val Gln Glu Leu Arg
            420                 425                 430 agg gcc atg aag gga gcc ggc act gat gag ggc tgc cta att gag atc   1344
Arg Ala Met Lys Gly Ala Gly Thr Asp Glu Gly Cys Leu Ile Glu Ile
                435                 440                 445 ctg gcc tcc cgg acc cct gag gag atc cgg cgc ata agc caa acc tac   1392
Leu Ala Ser Arg Thr Pro Glu Glu Ile Arg Arg Ile Ser Gln Thr Tyr
        450                 455                 460 cag cag caa tat gga cgg agg ctt gaa gat gac att cgc tct gac aca   1440
Gln Gln Gln Tyr Gly Arg Arg Leu Glu Asp Asp Ile Arg Ser Asp Thr
465                 470                 475                 480 tcg ttc atg ttc cag cga gtg ctg gtg tct ctg tca gct ggt ggg agg   1488
Ser Phe Met Phe Gln Arg Val Leu Val Ser Leu Ser Ala Gly Gly Arg
                485                 490                 495 gat gaa gga aat tat ctg gac gat gct ctc gtg aga cag gat gcc cag   1536
Asp Glu Gly Asn Tyr Leu Asp Asp Ala Leu Val Arg Gln Asp Ala Gln
            500                 505                 510 gac ctg tat gag gct gga gag aag aaa tgg ggg aca gat gag gtg aaa   1584
Asp Leu Tyr Glu Ala Gly Glu Lys Lys Trp Gly Thr Asp Glu Val Lys
                515                 520                 525 ttt cta act gtt ctc tgt tcc cgg aac cga aat cac ctg ttg cat gtg   1632
Phe Leu Thr Val Leu Cys Ser Arg Asn Arg Asn His Leu Leu His Val
        530                 535                 540 ttt gat gaa tac aaa agg ata tca cag aag gat att gaa cag agt att   1680
Phe Asp Glu Tyr Lys Arg Ile Ser Gln Lys Asp Ile Glu Gln Ser Ile
545                 550                 555                 560 aaa tct gaa aca tct ggt agc ttt gaa gat gct ctg ctg gct ata gta   1728
Lys Ser Glu Thr Ser Gly Ser Phe Glu Asp Ala Leu Leu Ala Ile Val
                565                 570                 575 aag tgc atg agg aac aaa tct gca tat ttt gct gaa aag ctc tat aaa   1776
Lys Cys Met Arg Asn Lys Ser Ala Tyr Phe Ala Glu Lys Leu Tyr Lys
            580                 585                 590 tcg atg aag ggc ttg ggc acc gat gat aac acc ctc atc aga gtg atg   1824
```

```
Ser Met Lys Gly Leu Gly Thr Asp Asp Asn Thr Leu Ile Arg Val Met
        595                 600                 605 gtt tct cga gca gaa att gac atg ttg gat atc cgg gca cac ttc aag    1872
Val Ser Arg Ala Glu Ile Asp Met Leu Asp Ile Arg Ala His Phe Lys
610                 615                 620 aga ctc tat gga aag tct ctg tac tcg ttc atc aag ggt gac aca tct    1920
Arg Leu Tyr Gly Lys Ser Leu Tyr Ser Phe Ile Lys Gly Asp Thr Ser
625                 630                 635                 640 gga gac tac agg aaa gta ctg ctt gtt ctc tgt gga gga gat gat taa    1968
Gly Asp Tyr Arg Lys Val Leu Leu Val Leu Cys Gly Gly Asp Asp
                    645                 650                 655 tag taa                                                            1974

<210> SEQ ID NO 19
<211> LENGTH: 655
<212> TYPE: PRT
<213> ORGANISM: Artificial sequence
<220> FEATURE:
<223> OTHER INFORMATION: Synthetic Construct

<400> SEQUENCE: 19

Met Ala Met Ala Thr Lys Gly Gly Thr Val Lys Ala Ala Ser Gly Phe
1               5                   10                  15

Asn Ala Met Glu Asp Ala Gln Thr Leu Arg Lys Ala Met Lys Gly Leu
            20                  25                  30

Gly Thr Asp Glu Asp Ala Ile Ile Ser Val Leu Ala Tyr Arg Asn Thr
        35                  40                  45

Ala Gln Arg Gln Glu Ile Arg Thr Ala Tyr Lys Ser Thr Ile Gly Arg
    50                  55                  60

Asp Leu Ile Asp Asp Leu Lys Ser Glu Leu Ser Gly Asn Phe Glu Gln
65                  70                  75                  80

Val Ile Val Gly Met Met Thr Pro Thr Val Leu Tyr Asp Val Gln Glu
                85                  90                  95

Leu Arg Arg Ala Met Lys Gly Ala Gly Thr Asp Glu Gly Cys Leu Ile
            100                 105                 110

Glu Ile Leu Ala Ser Arg Thr Pro Glu Glu Ile Arg Arg Ile Ser Gln
        115                 120                 125

Thr Tyr Gln Gln Gln Tyr Gly Arg Arg Leu Glu Asp Asp Ile Arg Ser
    130                 135                 140

Asp Thr Ser Phe Met Phe Gln Arg Val Leu Val Ser Leu Ser Ala Gly
145                 150                 155                 160

Gly Arg Asp Glu Gly Asn Tyr Leu Asp Asp Ala Leu Val Arg Gln Asp
                165                 170                 175

Ala Gln Asp Leu Tyr Glu Ala Gly Glu Lys Lys Trp Gly Thr Asp Glu
            180                 185                 190

Val Lys Phe Leu Thr Val Leu Cys Ser Arg Asn Arg Asn His Leu Leu
        195                 200                 205

His Val Phe Asp Glu Tyr Lys Arg Ile Ser Gln Lys Asp Ile Glu Gln
    210                 215                 220

Ser Ile Lys Ser Glu Thr Ser Gly Ser Phe Glu Asp Ala Leu Leu Ala
225                 230                 235                 240

Ile Val Lys Cys Met Arg Asn Lys Ser Ala Tyr Phe Ala Glu Lys Leu
                245                 250                 255

Tyr Lys Ser Met Lys Gly Leu Gly Thr Asp Asp Asn Thr Leu Ile Arg
            260                 265                 270

Val Met Val Ser Arg Ala Glu Ile Asp Met Leu Asp Ile Arg Ala His
```

```
                275                 280                 285
Phe Lys Arg Leu Tyr Gly Lys Ser Leu Tyr Ser Phe Ile Lys Gly Asp
290                 295                 300

Thr Ser Gly Asp Tyr Arg Lys Val Leu Val Leu Cys Gly Gly Asp
305                 310                 315                 320

Asp Gly Ser Leu Glu Val Leu Phe Gln Gly Pro Ser Gly Lys Leu Ala
                325                 330                 335

Met Ala Thr Lys Gly Gly Thr Val Lys Ala Ala Ser Gly Phe Asn Ala
                340                 345                 350

Met Glu Asp Ala Gln Thr Leu Arg Lys Ala Met Lys Gly Leu Gly Thr
                355                 360                 365

Asp Glu Asp Ala Ile Ile Ser Val Leu Ala Tyr Arg Asn Thr Ala Gln
                370                 375                 380

Arg Gln Glu Ile Arg Thr Ala Tyr Lys Ser Thr Ile Gly Arg Asp Leu
385                 390                 395                 400

Ile Asp Asp Leu Lys Ser Glu Leu Ser Gly Asn Phe Glu Gln Val Ile
                405                 410                 415

Val Gly Met Met Thr Pro Thr Val Leu Tyr Asp Val Gln Glu Leu Arg
                420                 425                 430

Arg Ala Met Lys Gly Ala Gly Thr Asp Glu Gly Cys Leu Ile Glu Ile
                435                 440                 445

Leu Ala Ser Arg Thr Pro Glu Glu Ile Arg Arg Ile Ser Gln Thr Tyr
                450                 455                 460

Gln Gln Gln Tyr Gly Arg Arg Leu Glu Asp Asp Ile Arg Ser Asp Thr
465                 470                 475                 480

Ser Phe Met Phe Gln Arg Val Leu Val Ser Leu Ser Ala Gly Gly Arg
                485                 490                 495

Asp Glu Gly Asn Tyr Leu Asp Asp Ala Leu Val Arg Gln Asp Ala Gln
                500                 505                 510

Asp Leu Tyr Glu Ala Gly Glu Lys Lys Trp Gly Thr Asp Glu Val Lys
                515                 520                 525

Phe Leu Thr Val Leu Cys Ser Arg Asn Arg Asn His Leu Leu His Val
530                 535                 540

Phe Asp Glu Tyr Lys Arg Ile Ser Gln Lys Asp Ile Glu Gln Ser Ile
545                 550                 555                 560

Lys Ser Glu Thr Ser Gly Ser Phe Glu Asp Ala Leu Leu Ala Ile Val
                565                 570                 575

Lys Cys Met Arg Asn Lys Ser Ala Tyr Phe Ala Glu Lys Leu Tyr Lys
                580                 585                 590

Ser Met Lys Gly Leu Gly Thr Asp Asp Asn Thr Leu Ile Arg Val Met
                595                 600                 605

Val Ser Arg Ala Glu Ile Asp Met Leu Asp Ile Arg Ala His Phe Lys
                610                 615                 620

Arg Leu Tyr Gly Lys Ser Leu Tyr Ser Phe Ile Lys Gly Asp Thr Ser
625                 630                 635                 640

Gly Asp Tyr Arg Lys Val Leu Leu Val Leu Cys Gly Gly Asp
                645                 650                 655

<210> SEQ ID NO 20
<211> LENGTH: 7257
<212> TYPE: DNA
<213> ORGANISM: Artificial sequence
<220> FEATURE:
<223> OTHER INFORMATION: plasmid
```

<400> SEQUENCE: 20

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta taagggattt tgccgatttc ggcctattgg ttaaaaatg agctgattta      420
acaaaatttt aacgcgaatt ttaacaaaat attaacgttt acaatttcag gtggcacttt     480
tcggggaaat gtgcgcggaa ccctatttg tttattttc taaatacatt caaatatgta      540
tccgctcatg aattaattct tagaaaaact catcgagcat caaatgaaac tgcaattat      600
tcatatcagg attatcaata ccatatttt gaaaagccg tttctgtaat gaaggagaaa      660
actcaccgag gcagttccat aggatggcaa gatcctggta tcggtctgcg attccgactc    720
gtccaacatc aatacaacct attaatttcc cctcgtcaaa ataaggtta tcaagtgaga     780
aatcaccatg agtgacgact gaatccggtg agaatggcaa agtttatgc atttctttcc    840
agacttgttc aacaggccag ccattacgct cgtcatcaaa atcactcgca tcaaccaaac    900
cgttattcat tcgtgattgc gcctgagcga acgaaatac gcgatcgctg ttaaaaggac    960
aattacaaac aggaatcgaa tgcaaccggc gcaggaacac tgccagcgca tcaacaatat  1020
tttcacctga atcaggatat tcttctaata cctggaatgc tgttttccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttattgt tcatgaccaa atcccttaa    1440
cgtgagtttt cgttccactg agcgtcagac cccgtagaaa agatcaaagg atcttcttga   1500
gatcctttt ttctgcgcgt aatctgctgc ttgcaaacaa aaaaccacc gctaccagcg     1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tatttctcc ttacgcatct gtgcggtatt tcacaccgca tatatggtgc actctcagta   2340
```

-continued

```
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
```

```
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcga tctcgatccc    4980
gcgaaattaa tacgactcac tatagggaa ttgtgagcgg ataacaattc ccctctagaa     5040
ataattttgt ttaactttaa gaaggagata tacatatggc ctggtggaaa gcctggattg    5100
aacaggaggg tgtcacagtg aagagcagct cccacttcaa cccagaccct gatgcagaga    5160
ccctctacaa agccatgaag gggatcggga ccaacgagca ggctatcatc gatgtgctca    5220
ccaagagaag caacacgcag cggcagcaga tcgccaagtc cttcaaggct cagttcggca    5280
aggacctcac tgagaccttg aagtctgagc tcagtggcaa gtttgagagg ctcattgtgg    5340
cccttatgta cccgccatac agatacgaag ccaaggagct gcatgacgcc atgaagggct    5400
taggaaccaa ggagggtgtc atcattgaga tcctggcctc tcggaccaag aaccagctgc    5460
gggagataat gaaggcgtat gaggaagact atgggtccag cctggaggag gacatccaag    5520
cagacacaag tggctacctg gagaggatcc tggtgtgcct cctgcagggc agcagggatg    5580
atgtgagcag ctttgtggac ccggcactgg ccctccaaga cgcacaggat ctgtatgcgg    5640
caggcgagaa gattcgtggg actgatgaga tgaaattcat caccatcctg tgcacgcgca    5700
gtgccactca cctgctgaga gtgtttgaag agtatgagaa aattgccaac aagagcattg    5760
aggacagcat caagagtgag acccatggct cactggagga ggccatgctc actgtggtga    5820
aatgcaccca aaacctccac agctactttg cagagagact ctactatgcc atgaagggag    5880
cagggacgcg tgatgggacc ctgataagaa acatcgtttc aaggagcgag attgacttaa    5940
atcttatcaa atgtcacttc aagaagatgt acggcaagac cctcagcagc atgatcatgg    6000
aagacaccag cggcgactac aagaacgccc tgctgagcct ggtgggcagc gaccccggat    6060
ccctggaggt gctgttccag ggccccctcg ggaagcttgc ctggtggaaa gcctggattg    6120
aacaggaggg tgtcacagtg aagagcagct cccacttcaa cccagaccct gatgcagaga    6180
ccctctacaa agccatgaag gggatcggga ccaacgagca ggctatcatc gatgtgctca    6240
ccaagagaag caacacgcag cggcagcaga tcgccaagtc cttcaaggct cagttcggca    6300
aggacctcac tgagaccttg aagtctgagc tcagtggcaa gtttgagagg ctcattgtgg    6360
cccttatgta cccgccatac agatacgaag ccaaggagct gcatgacgcc atgaagggct    6420
taggaaccaa ggagggtgtc atcattgaga tcctggcctc tcggaccaag aaccagctgc    6480
gggagataat gaaggcgtat gaggaagact atgggtccag cctggaggag gacatccaag    6540
cagacacaag tggctacctg gagaggatcc tggtgtgcct cctgcagggc agcagggatg    6600
atgtgagcag ctttgtggac ccggcactgg ccctccaaga cgcacaggat ctgtatgcgg    6660
caggcgagaa gattcgtggg actgatgaga tgaaattcat caccatcctg tgcacgcgca    6720
gtgccactca cctgctgaga gtgtttgaag agtatgagaa aattgccaac aagagcattg    6780
aggacagcat caagagtgag acccatggct cactggagga ggccatgctc actgtggtga    6840
aatgcaccca aaacctccac agctactttg cagagagact ctactatgcc atgaagggag    6900
cagggacgcg tgatgggacc ctgataagaa acatcgtttc aaggagcgag attgacttaa    6960
atcttatcaa atgtcacttc aagaagatgt acggcaagac cctcagcagc atgatcatgg    7020
aagacaccag cggcgactac aagaacgccc tgctgagcct ggtgggcagc gaccccgat     7080
```

```
aataagcggc cgcactcgag caccaccacc accaccactg agatccggct gctaacaaag    7140
cccgaaagga agctgagttg gctgctgcca ccgctgagca ataactagca taaccccttg    7200
gggcctctaa acgggtcttg aggggttttt tgctgaaagg aggaactata tccggat       7257

<210> SEQ ID NO 21
<211> LENGTH: 2004
<212> TYPE: DNA
<213> ORGANISM: Artificial sequence
<220> FEATURE:
<223> OTHER INFORMATION: plasmid

<400> SEQUENCE: 21
atggcctggt ggaaagcctg gattgaacag gagggtgtca cagtgaagag cagctcccac      60
ttcaacccag accctgatgc agagaccctc tacaaagcca tgaaggggat cgggaccaac     120
gagcaggcta tcatcgatgt gctcaccaag agaagcaaca cgcagcggca gcagatcgcc     180
aagtccttca aggctcagtt cggcaaggac ctcactgaga ccttgaagtc tgagctcagt     240
ggcaagtttg agaggctcat tgtggccctt atgtacccgc atacagata cgaagccaag     300 gagctgcatg acgccatgaa gggcttagga accaaggagg gtgtcatcat tgagatcctg     360
gcctctcgga ccaagaacca gctgcgggag ataatgaagg cgtatgagga agactatggg     420
tccagcctgg aggaggacat ccaagcagac acaagtggct acctggagag gatcctggtg     480
tgcctcctgc agggcagcag ggatgatgtg agcagctttg tggacccggc actggccctc     540
caagacgcac aggatctgta tgcggcaggc gagaagattc gtgggactga tgagatgaaa     600
ttcatcacca tcctgtgcac gcgcagtgcc actcacctgc tgagagtgtt tgaagagtat     660
gagaaaattg ccaacaagag cattgaggac agcatcaaga gtgagaccca tggctcactg     720
gaggaggcca tgctcactgt ggtgaaatgc acccaaaacc tccacagcta ctttgcagag     780
agactctact atgccatgaa gggagcaggg acgcgtgatg ggaccctgat aagaaacatc     840
gtttcaagga gcgagattga cttaaatctt atcaaatgtc acttcaagaa gatgtacggc     900 aagacccctca gcagcatgat catggaagac accagcggcg actacaagaa cgccctgctg     960
agcctggtgg gcagcgaccc cggatccctg gaggtgctgt tccagggccc ctccgggaag    1020
cttgcctggt ggaaagcctg gattgaacag gagggtgtca cagtgaagag cagctcccac    1080
ttcaacccag accctgatgc agagaccctc tacaaagcca tgaaggggat cgggaccaac    1140
gagcaggcta tcatcgatgt gctcaccaag agaagcaaca cgcagcggca gcagatcgcc    1200
aagtccttca aggctcagtt cggcaaggac ctcactgaga ccttgaagtc tgagctcagt    1260
ggcaagtttg agaggctcat tgtggccctt atgtacccgc atacagata cgaagccaag    1320 gagctgcatg acgccatgaa gggcttagga accaaggagg gtgtcatcat tgagatcctg    1380
gcctctcgga ccaagaacca gctgcgggag ataatgaagg cgtatgagga agactatggg    1440
tccagcctgg aggaggacat ccaagcagac acaagtggct acctggagag gatcctggtg    1500
tgcctcctgc agggcagcag ggatgatgtg agcagctttg tggacccggc actggccctc    1560
caagacgcac aggatctgta tgcggcaggc gagaagattc gtgggactga tgagatgaaa    1620
ttcatcacca tcctgtgcac gcgcagtgcc actcacctgc tgagagtgtt tgaagagtat    1680
gagaaaattg ccaacaagag cattgaggac agcatcaaga gtgagaccca tggctcactg    1740
gaggaggcca tgctcactgt ggtgaaatgc acccaaaacc tccacagcta ctttgcagag    1800
agactctact atgccatgaa gggagcaggg acgcgtgatg ggaccctgat aagaaacatc    1860
```

```
gtttcaagga gcgagattga cttaaatctt atcaaatgtc acttcaagaa gatgtacggc    1920
aagaccctca gcagcatgat catggaagac accagcggcg actacaagaa cgccctgctg    1980
agcctggtgg gcagcgaccc ctga                                           2004
```

```
<210> SEQ ID NO 22
<211> LENGTH: 2004
<212> TYPE: DNA
<213> ORGANISM: Artificial sequence
<220> FEATURE:
<223> OTHER INFORMATION: plasmid
<220> FEATURE:
<221> NAME/KEY: CDS
<222> LOCATION: (1)..(2004)

<400> SEQUENCE: 22
```

```
atg gcc tgg tgg aaa gcc tgg att gaa cag gag ggt gtc aca gtg aag      48
Met Ala Trp Trp Lys Ala Trp Ile Glu Gln Glu Gly Val Thr Val Lys
1               5                  10                  15 agc agc tcc cac ttc aac cca gac cct gat gca gag acc ctc tac aaa      96
Ser Ser Ser His Phe Asn Pro Asp Pro Asp Ala Glu Thr Leu Tyr Lys
                20                  25                  30 gcc atg aag ggg atc ggg acc aac gag cag gct atc atc gat gtg ctc     144
Ala Met Lys Gly Ile Gly Thr Asn Glu Gln Ala Ile Ile Asp Val Leu
            35                  40                  45 acc aag aga agc aac acg cag cgg cag cag atc gcc aag tcc ttc aag     192
Thr Lys Arg Ser Asn Thr Gln Arg Gln Gln Ile Ala Lys Ser Phe Lys
        50                  55                  60 gct cag ttc ggc aag gac ctc act gag acc ttg aag tct gag ctc agt     240
Ala Gln Phe Gly Lys Asp Leu Thr Glu Thr Leu Lys Ser Glu Leu Ser
65                  70                  75                  80 ggc aag ttt gag agg ctc att gtg gcc ctt atg tac ccg cca tac aga     288
Gly Lys Phe Glu Arg Leu Ile Val Ala Leu Met Tyr Pro Pro Tyr Arg
                85                  90                  95 tac gaa gcc aag gag ctg cat gac gcc atg aag ggc tta gga acc aag     336
Tyr Glu Ala Lys Glu Leu His Asp Ala Met Lys Gly Leu Gly Thr Lys
            100                 105                 110 gag ggt gtc atc att gag atc ctg gcc tct cgg acc aag aac cag ctg     384
Glu Gly Val Ile Ile Glu Ile Leu Ala Ser Arg Thr Lys Asn Gln Leu
        115                 120                 125 cgg gag ata atg aag gcg tat gag gaa gac tat ggg tcc agc ctg gag     432
Arg Glu Ile Met Lys Ala Tyr Glu Glu Asp Tyr Gly Ser Ser Leu Glu
    130                 135                 140 gag gac atc caa gca gac aca agt ggc tac ctg gag agg atc ctg gtg     480
Glu Asp Ile Gln Ala Asp Thr Ser Gly Tyr Leu Glu Arg Ile Leu Val
145                 150                 155                 160 tgc ctc ctg cag ggc agc agg gat gat gtg agc agc ttt gtg gac ccg     528
Cys Leu Leu Gln Gly Ser Arg Asp Asp Val Ser Ser Phe Val Asp Pro
                165                 170                 175 gca ctg gcc ctc caa gac gca cag gat ctg tat gcg gca ggc gag aag     576
Ala Leu Ala Leu Gln Asp Ala Gln Asp Leu Tyr Ala Ala Gly Glu Lys
            180                 185                 190 att cgt ggg act gat gag atg aaa ttc atc acc atc ctg tgc acg cgc     624
Ile Arg Gly Thr Asp Glu Met Lys Phe Ile Thr Ile Leu Cys Thr Arg
        195                 200                 205 agt gcc act cac ctg ctg aga gtg ttt gaa gag tat gag aaa att gcc     672
Ser Ala Thr His Leu Leu Arg Val Phe Glu Glu Tyr Glu Lys Ile Ala
    210                 215                 220 aac aag agc att gag gac agc atc aag agt gag acc cat ggc tca ctg     720
Asn Lys Ser Ile Glu Asp Ser Ile Lys Ser Glu Thr His Gly Ser Leu
225                 230                 235                 240
```

```
                                          -continued gag gag gcc atg ctc act gtg gtg aaa tgc acc caa aac ctc cac agc       768
Glu Glu Ala Met Leu Thr Val Val Lys Cys Thr Gln Asn Leu His Ser
            245                 250                 255 tac ttt gca gag aga ctc tac tat gcc atg aag gga gca ggg acg cgt       816
Tyr Phe Ala Glu Arg Leu Tyr Tyr Ala Met Lys Gly Ala Gly Thr Arg
    260                 265                 270 gat ggg acc ctg ata aga aac atc gtt tca agg agc gag att gac tta       864
Asp Gly Thr Leu Ile Arg Asn Ile Val Ser Arg Ser Glu Ile Asp Leu
275                 280                 285 aat ctt atc aaa tgt cac ttc aag aag atg tac ggc aag acc ctc agc       912
Asn Leu Ile Lys Cys His Phe Lys Lys Met Tyr Gly Lys Thr Leu Ser
        290                 295                 300 agc atg atc atg gaa gac acc agc ggc gac tac aag aac gcc ctg ctg       960
Ser Met Ile Met Glu Asp Thr Ser Gly Asp Tyr Lys Asn Ala Leu Leu
305                 310                 315                 320 agc ctg gtg ggc agc gac ccc gga tcc ctg gag gtg ctg ttc cag ggc      1008
Ser Leu Val Gly Ser Asp Pro Gly Ser Leu Glu Val Leu Phe Gln Gly
                325                 330                 335 ccc tcc ggg aag ctt gcc tgg tgg aaa gcc tgg att gaa cag gag ggt      1056
Pro Ser Gly Lys Leu Ala Trp Trp Lys Ala Trp Ile Glu Gln Glu Gly
            340                 345                 350 gtc aca gtg aag agc agc tcc cac ttc aac cca gac cct gat gca gag      1104
Val Thr Val Lys Ser Ser Ser His Phe Asn Pro Asp Pro Asp Ala Glu
        355                 360                 365 acc ctc tac aaa gcc atg aag ggg atc ggg acc aac gag cag gct atc      1152
Thr Leu Tyr Lys Ala Met Lys Gly Ile Gly Thr Asn Glu Gln Ala Ile
370                 375                 380 atc gat gtg ctc acc aag aga agc aac acg cag cgg cag cag atc gcc      1200
Ile Asp Val Leu Thr Lys Arg Ser Asn Thr Gln Arg Gln Gln Ile Ala
385                 390                 395                 400 aag tcc ttc aag gct cag ttc ggc aag gac ctc act gag acc ttg aag      1248
Lys Ser Phe Lys Ala Gln Phe Gly Lys Asp Leu Thr Glu Thr Leu Lys
                405                 410                 415 tct gag ctc agt ggc aag ttt gag agg ctc att gtg gcc ctt atg tac      1296
Ser Glu Leu Ser Gly Lys Phe Glu Arg Leu Ile Val Ala Leu Met Tyr
            420                 425                 430 ccg cca tac aga tac gaa gcc aag gag ctg cat gac gcc atg aag ggc      1344
Pro Pro Tyr Arg Tyr Glu Ala Lys Glu Leu His Asp Ala Met Lys Gly
        435                 440                 445 tta gga acc aag gag ggt gtc atc att gag atc ctg gcc tct cgg acc      1392
Leu Gly Thr Lys Glu Gly Val Ile Ile Glu Ile Leu Ala Ser Arg Thr
    450                 455                 460 aag aac cag ctg cgg gag ata atg aag gcg tat gag gaa gac tat ggg      1440
Lys Asn Gln Leu Arg Glu Ile Met Lys Ala Tyr Glu Glu Asp Tyr Gly
465                 470                 475                 480 tcc agc ctg gag gag gac atc caa gca gac aca agt ggc tac ctg gag      1488
Ser Ser Leu Glu Glu Asp Ile Gln Ala Asp Thr Ser Gly Tyr Leu Glu
                485                 490                 495 agg atc ctg gtg tgc ctc ctg cag ggc agc agg gat gat gtg agc agc      1536
Arg Ile Leu Val Cys Leu Leu Gln Gly Ser Arg Asp Asp Val Ser Ser
            500                 505                 510 ttt gtg gac ccg gca ctg gcc ctc caa gac gca cag gat ctg tat gcg      1584
Phe Val Asp Pro Ala Leu Ala Leu Gln Asp Ala Gln Asp Leu Tyr Ala
        515                 520                 525 gca ggc gag aag att cgt ggg act gat gag atg aaa ttc atc acc atc      1632
Ala Gly Glu Lys Ile Arg Gly Thr Asp Glu Met Lys Phe Ile Thr Ile
    530                 535                 540 ctg tgc acg cgc agt gcc act cac ctg ctg aga gtg ttt gaa gag tat      1680
Leu Cys Thr Arg Ser Ala Thr His Leu Leu Arg Val Phe Glu Glu Tyr
545                 550                 555                 560
```

```
gag aaa att gcc aac aag agc att gag gac agc atc aag agt gag acc      1728
Glu Lys Ile Ala Asn Lys Ser Ile Glu Asp Ser Ile Lys Ser Glu Thr
            565                 570                 575 cat ggc tca ctg gag gag gcc atg ctc act gtg gtg aaa tgc acc caa      1776
His Gly Ser Leu Glu Glu Ala Met Leu Thr Val Val Lys Cys Thr Gln
        580                 585                 590 aac ctc cac agc tac ttt gca gag aga ctc tac tat gcc atg aag gga      1824
Asn Leu His Ser Tyr Phe Ala Glu Arg Leu Tyr Tyr Ala Met Lys Gly
    595                 600                 605 gca ggg acg cgt gat ggg acc ctg ata aga aac atc gtt tca agg agc      1872
Ala Gly Thr Arg Asp Gly Thr Leu Ile Arg Asn Ile Val Ser Arg Ser
610                 615                 620 gag att gac tta aat ctt atc aaa tgt cac ttc aag aag atg tac ggc      1920
Glu Ile Asp Leu Asn Leu Ile Lys Cys His Phe Lys Lys Met Tyr Gly
625                 630                 635                 640 aag acc ctc agc agc atg atc atg gaa gac acc agc ggc gac tac aag      1968
Lys Thr Leu Ser Ser Met Ile Met Glu Asp Thr Ser Gly Asp Tyr Lys
                645                 650                 655 aac gcc ctg ctg agc ctg gtg ggc agc gac ccc tga                      2004
Asn Ala Leu Leu Ser Leu Val Gly Ser Asp Pro
            660                 665
```

<210> SEQ ID NO 23
<211> LENGTH: 667
<212> TYPE: PRT
<213> ORGANISM: Artificial sequence
<220> FEATURE:
<223> OTHER INFORMATION: Synthetic Construct

<400> SEQUENCE: 23

```
Met Ala Trp Trp Lys Ala Trp Ile Glu Gln Glu Gly Val Thr Val Lys
1               5                   10                  15

Ser Ser His Phe Asn Pro Asp Pro Asp Ala Glu Thr Leu Tyr Lys
            20                  25                  30

Ala Met Lys Gly Ile Gly Thr Asn Glu Gln Ala Ile Ile Asp Val Leu
        35                  40                  45

Thr Lys Arg Ser Asn Thr Gln Arg Gln Gln Ile Ala Lys Ser Phe Lys
    50                  55                  60

Ala Gln Phe Gly Lys Asp Leu Thr Glu Thr Leu Lys Ser Glu Leu Ser
65                  70                  75                  80

Gly Lys Phe Glu Arg Leu Ile Val Ala Leu Met Tyr Pro Pro Tyr Arg
                85                  90                  95

Tyr Glu Ala Lys Glu Leu His Asp Ala Met Lys Gly Leu Gly Thr Lys
            100                 105                 110

Glu Gly Val Ile Ile Glu Ile Leu Ala Ser Arg Thr Lys Asn Gln Leu
        115                 120                 125

Arg Glu Ile Met Lys Ala Tyr Glu Glu Asp Tyr Gly Ser Ser Leu Glu
    130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
                165                 170                 175

Ala Leu Ala Leu Gln Asp Ala Gln Asp Leu Tyr Ala Ala Gly Glu Lys
            180                 185                 190

Ile Arg Gly Thr Asp Glu Met Lys Phe Ile Thr Ile Leu Cys Thr Arg
        195                 200                 205

Ser Ala Thr His Leu Leu Arg Val Phe Glu Glu Tyr Glu Lys Ile Ala
```

-continued

```
            210                 215                 220
Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
            245                 250                 255

Tyr Phe Ala Glu Arg Leu Tyr Tyr Ala Met Lys Gly Ala Gly Thr Arg
                260                 265                 270

Asp Gly Thr Leu Ile Arg Asn Ile Val Ser Arg Ser Glu Ile Asp Leu
            275                 280                 285

Asn Leu Ile Lys Cys His Phe Lys Lys Met Tyr Gly Lys Thr Leu Ser
290                 295                 300

Ser Met Ile Met Glu Asp Thr Ser Gly Asp Tyr Lys Asn Ala Leu Leu
305                 310                 315                 320

Ser Leu Val Gly Ser Asp Pro Gly Ser Leu Glu Val Leu Phe Gln Gly
                325                 330                 335

Pro Ser Gly Lys Leu Ala Trp Trp Lys Ala Trp Ile Glu Gln Glu Gly
                340                 345                 350

Val Thr Val Lys Ser Ser His Phe Asn Pro Asp Pro Asp Ala Glu
            355                 360                 365

Thr Leu Tyr Lys Ala Met Lys Gly Ile Gly Thr Asn Glu Gln Ala Ile
        370                 375                 380

Ile Asp Val Leu Thr Lys Arg Ser Asn Thr Gln Arg Gln Gln Ile Ala
385                 390                 395                 400

Lys Ser Phe Lys Ala Gln Phe Gly Lys Asp Leu Thr Glu Thr Leu Lys
                405                 410                 415

Ser Glu Leu Ser Gly Lys Phe Glu Arg Leu Ile Val Ala Leu Met Tyr
                420                 425                 430

Pro Pro Tyr Arg Tyr Glu Ala Lys Glu Leu His Asp Ala Met Lys Gly
            435                 440                 445

Leu Gly Thr Lys Glu Gly Val Ile Ile Glu Ile Leu Ala Ser Arg Thr
        450                 455                 460

Lys Asn Gln Leu Arg Glu Ile Met Lys Ala Tyr Glu Glu Asp Tyr Gly
465                 470                 475                 480

Ser Ser Leu Glu Glu Asp Ile Gln Ala Asp Thr Ser Gly Tyr Leu Glu
            485                 490                 495

Arg Ile Leu Val Cys Leu Leu Gln Gly Ser Arg Asp Asp Val Ser Ser
                500                 505                 510

Phe Val Asp Pro Ala Leu Ala Leu Gln Asp Ala Gln Asp Leu Tyr Ala
            515                 520                 525

Ala Gly Glu Lys Ile Arg Gly Thr Asp Glu Met Lys Phe Ile Thr Ile
        530                 535                 540

Leu Cys Thr Arg Ser Ala Thr His Leu Leu Arg Val Phe Glu Glu Tyr
545                 550                 555                 560

Glu Lys Ile Ala Asn Lys Ser Ile Glu Asp Ser Ile Lys Ser Glu Thr
                565                 570                 575

His Gly Ser Leu Glu Glu Ala Met Leu Thr Val Val Lys Cys Thr Gln
            580                 585                 590

Asn Leu His Ser Tyr Phe Ala Glu Arg Leu Tyr Tyr Ala Met Lys Gly
        595                 600                 605

Ala Gly Thr Arg Asp Gly Thr Leu Ile Arg Asn Ile Val Ser Arg Ser
        610                 615                 620

Glu Ile Asp Leu Asn Leu Ile Lys Cys His Phe Lys Lys Met Tyr Gly
625                 630                 635                 640
```

```
Lys Thr Leu Ser Ser Met Ile Met Glu Asp Thr Ser Gly Asp Tyr Lys
                645                 650                 655

Asn Ala Leu Leu Ser Leu Val Gly Ser Asp Pro
            660                 665
```

<210> SEQ ID NO 24
<211> LENGTH: 5
<212> TYPE: PRT
<213> ORGANISM: artificial sequence
<220> FEATURE:
<223> OTHER INFORMATION: flexible linker

<400> SEQUENCE: 24

```
Gly Gly Gly Gly Ser
1               5
```

<210> SEQ ID NO 25
<211> LENGTH: 5
<212> TYPE: PRT
<213> ORGANISM: artificial sequence
<220> FEATURE:
<223> OTHER INFORMATION: flexible linker

<400> SEQUENCE: 25

```
Glu Ala Ala Ala Lys
1               5
```

<210> SEQ ID NO 26
<211> LENGTH: 660
<212> TYPE: PRT
<213> ORGANISM: artificial sequence
<220> FEATURE:
<223> OTHER INFORMATION: His-tagged annexin V homodimer

<400> SEQUENCE: 26

```
Met His His His His His His Gln Ala Gln Val Leu Arg Gly Thr Val
1               5                   10                  15

Thr Asp Phe Pro Gly Phe Asp Glu Arg Ala Asp Ala Glu Thr Leu Arg
                20                  25                  30

Lys Ala Met Lys Gly Leu Gly Thr Asp Glu Glu Ser Ile Leu Thr Leu
            35                  40                  45

Leu Thr Ser Arg Ser Asn Ala Gln Arg Gln Glu Ile Ser Ala Ala Phe
    50                  55                  60

Lys Thr Leu Phe Gly Arg Asp Leu Leu Asp Asp Leu Lys Ser Glu Leu
65                  70                  75                  80

Thr Gly Lys Phe Glu Lys Leu Ile Val Ala Leu Met Lys Pro Ser Arg
                85                  90                  95

Leu Tyr Asp Ala Tyr Glu Leu Lys His Ala Leu Lys Gly Ala Gly Thr
                100                 105                 110

Asn Glu Lys Val Leu Thr Glu Ile Ile Ala Ser Arg Thr Pro Glu Glu
            115                 120                 125

Leu Arg Ala Ile Lys Gln Val Tyr Glu Glu Tyr Gly Ser Ser Leu
    130                 135                 140

Glu Asp Asp Val Val Gly Asp Thr Ser Gly Tyr Tyr Gln Arg Met Leu
145                 150                 155                 160

Val Val Leu Leu Gln Ala Asn Arg Asp Pro Asp Ala Gly Ile Asp Glu
                165                 170                 175

Ala Gln Val Glu Gln Asp Ala Gln Ala Leu Phe Gln Ala Gly Glu Leu
                180                 185                 190
```

```
Lys Trp Gly Thr Asp Glu Glu Lys Phe Ile Thr Ile Phe Gly Thr Arg
            195                 200                 205
Ser Val Ser His Leu Arg Lys Val Phe Asp Lys Tyr Met Thr Ile Ser
        210                 215                 220
Gly Phe Gln Ile Glu Glu Thr Ile Asp Arg Glu Thr Ser Gly Asn Leu
225                 230                 235                 240
Glu Gln Leu Leu Leu Ala Val Val Lys Ser Ile Arg Ser Ile Pro Ala
                245                 250                 255
Tyr Leu Ala Glu Thr Leu Tyr Tyr Ala Met Lys Gly Ala Gly Thr Asp
            260                 265                 270
Asp His Thr Leu Ile Arg Val Met Val Ser Arg Ser Glu Ile Asp Leu
        275                 280                 285
Phe Asn Ile Arg Lys Glu Phe Arg Lys Asn Phe Ala Thr Ser Leu Tyr
290                 295                 300
Ser Met Ile Lys Gly Asp Thr Ser Gly Asp Tyr Lys Lys Ala Leu Leu
305                 310                 315                 320
Leu Leu Cys Gly Glu Asp Asp Gly Ser Leu Glu Val Leu Phe Gln Gly
                325                 330                 335
Pro Ser Gly Lys Leu Ala Gln Val Leu Arg Gly Thr Val Thr Asp Phe
            340                 345                 350
Pro Gly Phe Asp Glu Arg Ala Asp Ala Glu Thr Leu Arg Lys Ala Met
        355                 360                 365
Lys Gly Leu Gly Thr Asp Glu Glu Ser Ile Leu Thr Leu Leu Thr Ser
370                 375                 380
Arg Ser Asn Ala Gln Arg Gln Glu Ile Ser Ala Ala Phe Lys Thr Leu
385                 390                 395                 400
Phe Gly Arg Asp Leu Leu Asp Asp Leu Lys Ser Glu Leu Thr Gly Lys
                405                 410                 415
Phe Glu Lys Leu Ile Val Ala Leu Met Lys Pro Ser Arg Leu Tyr Asp
            420                 425                 430
Ala Tyr Glu Leu Lys His Ala Leu Lys Gly Ala Gly Thr Asn Glu Lys
        435                 440                 445
Val Leu Thr Glu Ile Ile Ala Ser Arg Thr Pro Glu Glu Leu Arg Ala
450                 455                 460
Ile Lys Gln Val Tyr Glu Glu Glu Tyr Gly Ser Ser Leu Glu Asp Asp
465                 470                 475                 480
Val Val Gly Asp Thr Ser Gly Tyr Tyr Gln Arg Met Leu Val Val Leu
                485                 490                 495
Leu Gln Ala Asn Arg Asp Pro Asp Ala Gly Ile Asp Glu Ala Gln Val
            500                 505                 510
Glu Gln Asp Ala Gln Ala Leu Phe Gln Ala Gly Glu Leu Lys Trp Gly
        515                 520                 525
Thr Asp Glu Glu Lys Phe Ile Thr Ile Phe Gly Thr Arg Ser Val Ser
530                 535                 540
His Leu Arg Lys Val Phe Asp Lys Tyr Met Thr Ile Ser Gly Phe Gln
545                 550                 555                 560
Ile Glu Glu Thr Ile Asp Arg Glu Thr Ser Gly Asn Leu Glu Gln Leu
                565                 570                 575
Leu Leu Ala Val Val Lys Ser Ile Arg Ser Ile Pro Ala Tyr Leu Ala
            580                 585                 590
Glu Thr Leu Tyr Tyr Ala Met Lys Gly Ala Gly Thr Asp Asp His Thr
        595                 600                 605
Leu Ile Arg Val Met Val Ser Arg Ser Glu Ile Asp Leu Phe Asn Ile
```

```
                    610                 615                 620
Arg Lys Glu Phe Arg Lys Asn Phe Ala Thr Ser Leu Tyr Ser Met Ile
625                 630                 635                 640

Lys Gly Asp Thr Ser Gly Asp Tyr Lys Lys Ala Leu Leu Leu Leu Cys
                    645                 650                 655

Gly Glu Asp Asp
            660

<210> SEQ ID NO 27
<211> LENGTH: 653
<212> TYPE: PRT
<213> ORGANISM: artificial sequence
<220> FEATURE:
<223> OTHER INFORMATION: non-His-tagged annexin V homodimer

<400> SEQUENCE: 27

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
290                 295                 300

Ser Gly Asp Tyr Lys Lys Ala Leu Leu Leu Leu Cys Gly Glu Asp Asp
```

```
                305                 310                 315                 320

Gly Ser Leu Glu Val Leu Phe Gln Gly Pro Ser Gly Lys Leu Ala Gln
                325                 330                 335

Val Leu Arg Gly Thr Val Thr Asp Phe Pro Gly Phe Asp Glu Arg Ala
                340                 345                 350

Asp Ala Glu Thr Leu Arg Lys Ala Met Lys Gly Leu Gly Thr Asp Glu
                355                 360                 365

Glu Ser Ile Leu Thr Leu Leu Thr Ser Arg Ser Asn Ala Gln Arg Gln
                370                 375                 380

Glu Ile Ser Ala Ala Phe Lys Thr Leu Phe Gly Arg Asp Leu Leu Asp
385                 390                 395                 400

Asp Leu Lys Ser Glu Leu Thr Gly Lys Phe Glu Lys Leu Ile Val Ala
                405                 410                 415

Leu Met Lys Pro Ser Arg Leu Tyr Asp Ala Tyr Glu Leu Lys His Ala
                420                 425                 430

Leu Lys Gly Ala Gly Thr Asn Glu Lys Val Leu Thr Glu Ile Ile Ala
                435                 440                 445

Ser Arg Thr Pro Glu Glu Leu Arg Ala Ile Lys Gln Val Tyr Glu Glu
                450                 455                 460

Glu Tyr Gly Ser Ser Leu Glu Asp Asp Val Val Gly Asp Thr Ser Gly
465                 470                 475                 480

Tyr Tyr Gln Arg Met Leu Val Val Leu Leu Gln Ala Asn Arg Asp Pro
                485                 490                 495

Asp Ala Gly Ile Asp Glu Ala Gln Val Glu Gln Asp Ala Gln Ala Leu
                500                 505                 510

Phe Gln Ala Gly Glu Leu Lys Trp Gly Thr Asp Glu Glu Lys Phe Ile
                515                 520                 525

Thr Ile Phe Gly Thr Arg Ser Val Ser His Leu Arg Lys Val Phe Asp
                530                 535                 540

Lys Tyr Met Thr Ile Ser Gly Phe Gln Ile Glu Thr Ile Asp Arg
545                 550                 555                 560

Glu Thr Ser Gly Asn Leu Glu Gln Leu Leu Leu Ala Val Val Lys Ser
                565                 570                 575

Ile Arg Ser Ile Pro Ala Tyr Leu Ala Glu Thr Leu Tyr Tyr Ala Met
                580                 585                 590

Lys Gly Ala Gly Thr Asp Asp His Thr Leu Ile Arg Val Met Val Ser
                595                 600                 605

Arg Ser Glu Ile Asp Leu Phe Asn Ile Arg Lys Glu Phe Arg Lys Asn
                610                 615                 620

Phe Ala Thr Ser Leu Tyr Ser Met Ile Lys Gly Asp Thr Ser Gly Asp
625                 630                 635                 640

Tyr Lys Lys Ala Leu Leu Leu Cys Gly Glu Asp Asp
                645                 650

<210> SEQ ID NO 28
<211> LENGTH: 14
<212> TYPE: PRT
<213> ORGANISM: Artificial Sequence
<220> FEATURE:
<223> OTHER INFORMATION: linker

<400> SEQUENCE: 28

Gly Ser Leu Glu Val Leu Phe Gln Gly Pro Ser Gly Lys Leu
1               5                   10
```